US010242153B2

(12) United States Patent
Aneja et al.

(10) Patent No.: US 10,242,153 B2
(45) Date of Patent: *Mar. 26, 2019

(54) METHOD FOR DETERMINING THE RISK PROFILE OF NEOPLASTIC TISSUE

(71) Applicant: NOVAZOI THERANOSTICS, Rolling Hills Estates, CA (US)

(72) Inventors: Ritu Aneja, Lilburn, GA (US); Padmashree C. G. Rida, Plano, TX (US)

(73) Assignee: NOVAZOI THERANOSTICS, Rancho Palos Verdes, CA (US)

(*) Notice: Subject to any disclaimer, the term of this patent is extended or adjusted under 35 U.S.C. 154(b) by 84 days.

This patent is subject to a terminal disclaimer.

(21) Appl. No.: 15/419,693

(22) Filed: Jan. 30, 2017

(65) Prior Publication Data

US 2017/0140094 A1 May 18, 2017

Related U.S. Application Data

(63) Continuation of application No. 14/632,778, filed on Feb. 26, 2015, now Pat. No. 9,589,100.

(Continued)

(51) Int. Cl.
*G06K 9/00* (2006.01)
*G06F 19/20* (2011.01)
(Continued)

(52) U.S. Cl.
CPC .......... *G06F 19/20* (2013.01); *A61K 31/343* (2013.01); *A61K 31/365* (2013.01);
(Continued)

(58) Field of Classification Search
CPC ....... G01N 33/57407; G01N 33/57415; G01N 33/57438; G01N 33/57496; G06F 19/20; G06F 19/3431
See application file for complete search history.

(56) References Cited

U.S. PATENT DOCUMENTS 5,972,626 A   10/1999  Doxsey
6,368,818 B1 * 4/2002  Kong ............... A61K 31/41
                                                435/29
(Continued)

FOREIGN PATENT DOCUMENTS

WO      2011/008262      1/2011

OTHER PUBLICATIONS

International Search Report and the Written Opinion of the International Searching Authority of International Application No. PCT/US2015/017796 dated May 8, 2015.
(Continued)

*Primary Examiner* — Bhavesh M Mehta
*Assistant Examiner* — Ian L Lemieux
(74) *Attorney, Agent, or Firm* — Ping Wang; Morris, Manning & Martin, LLP

(57) ABSTRACT

A method of computing the risk profile of a neoplastic tissue in a patient is disclosed. The method includes the steps of (a) processing a sample of tumor tissue or cancer cells from the patient in a form suitable for visualization and demarcation of cell nuclei, individually distinguishable centrosomes (iCTRs) and megacentrosomes (mCTRs) in a region of interest (ROI) defined by a plurality of cell nuclei; (b) determining the numbers of iCTRs and mCTRs associated with each cell nucleus in the ROI; (c) determining the volume of each iCTR and mCTR in the ROI; and (d) calculating one or more centrosome amplification scores (CASs) values for the sample based on steps (b) and (c), wherein the one or more CASs indicate the severity of centrosome amplification, the frequency of centrosome amplification, or both, and wherein the one or more scores provide a measure of a level of risk and/or a prognosis associated with the neoplastic tissue.

18 Claims, 18 Drawing Sheets

Related U.S. Application Data

(60) Provisional application No. 61/946,462, filed on Feb. 28, 2014.

(51) Int. Cl.

| | |
|---|---|
| *G01N 33/574* | (2006.01) |
| *G16H 50/30* | (2018.01) |
| *A61K 31/343* | (2006.01) |
| *A61K 31/365* | (2006.01) |
| *A61K 31/473* | (2006.01) |
| *G01N 33/58* | (2006.01) |
| *G06F 19/18* | (2011.01) |
| *G06F 19/00* | (2018.01) |

(52) U.S. Cl.
CPC ..... *A61K 31/473* (2013.01); *G01N 33/57407* (2013.01); *G01N 33/57415* (2013.01); *G01N 33/57438* (2013.01); *G01N 33/57496* (2013.01); *G01N 33/582* (2013.01); *G06F 19/00* (2013.01); *G06F 19/18* (2013.01); *G16H 50/30* (2018.01)

(56) References Cited

U.S. PATENT DOCUMENTS

| | | |
|---|---|---|
| 8,077,958 B2 | 12/2011 | Qian et al. |
| 2004/0115697 A1 | 6/2004 | Doxsey et al. |
| 2008/0051463 A1 | 2/2008 | Gerlach et al. |
| 2011/0190374 A1* | 8/2011 | Pellman ............ A61K 31/7088 514/44 A |
| 2012/0177280 A1 | 7/2012 | Zhukov et al. |
| 2015/0346191 A1 | 12/2015 | Aneja |

OTHER PUBLICATIONS

Guo, H. Q. et al., "Analysis of the cellular centrosome in fine-needle aspirations of the breast," Breast Cancer Research, 2007, vol. 9(4), pp. 1-7.

Iemura, K. et al., "Assessment of the centrosome amplification by quantification of gamma-tubulin in Western blotting," Analytical Biochemistry, 2007, vol. 371(2), pp. 256-258.

Fleisch, M. C. et al., "Intensity-based signal separation algorithm for accurate quantification of clustered centrosomes in tissue sections," Microscopy Research and Technique, 2006, vol. 69(12), pp. 964-972.

Cox, "Regression Models and Life-Tables", Journal of the Royal Statistical Society. Series B (Methodological), vol. 34, No. 2, pp. 187-220, (1972).

Huck, et al., "MLN8054, an Inhibitor of Aurora A Kinase, Induces Senescence in Human Tumor Cells Both In vitro and In vivo", Molecular Cancer Research, vol. 8, No. 3, pp. 373-384, (Mar. 2, 2010).

Manfredi, et al., "Antitumor Activity of MLN8054, an Orally Active Small-Molecule Inhibitor of Aurora A Kinase", PNAS, vol. 104, No. 10, pp. 4106-4111, (Mar. 6, 2007).

Spruance, et. al., "Hazard Ratio in Clinical Trials", Antimicrobial Agents and Chemotherapy, vol. 48, No. 8, pp. 2787-2792, (Aug. 2004).

Song, et al., "Quantificational and Statistical Analysis of the Differences in Centrosomal Features of Untreated Lung Cancer Cells and Normal Cells", Anal Quant Cytol Histol., vol. 32, No. 5, pp. 280-290, (Oct. 2010).

File History of U.S. Appl. No. 14/632,778, filed Feb. 26, 2015.

* cited by examiner

A
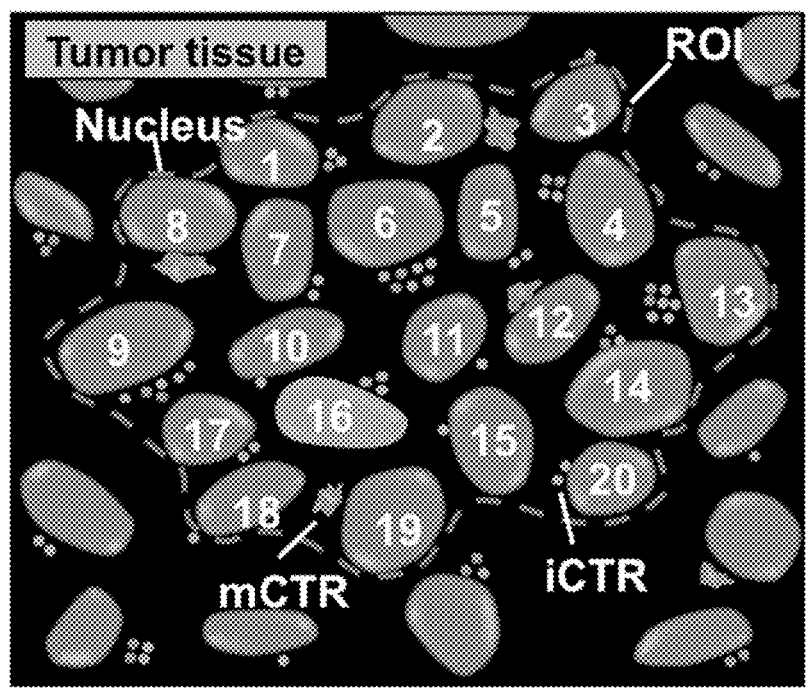
B
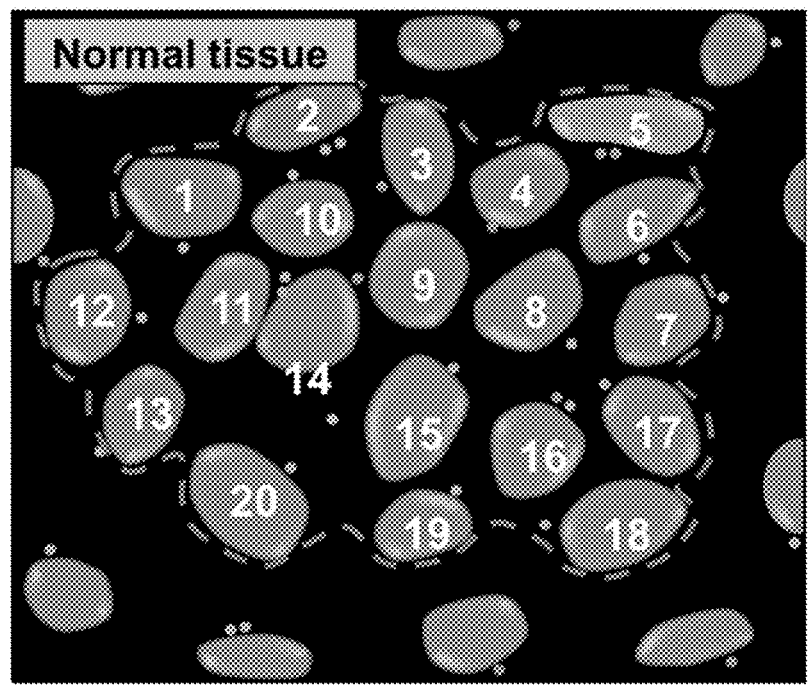
FIGURE 2

Sample CAS calculation for normal cells:
No. of iCTRs = 1-2 per nucleus
No. of mCTRs = 0
CAS value (per 100 nuclei) =

$$\frac{(\text{Between } 100\text{-}200)}{100} + 0 + 1 + 0$$

= value between 2 and 3.

Sample CAS calculation (per 100 nuclei) for a tumor where:
No. of iCTRs = 250,
No. of mCTRs = 30,
Avg. vol of iCTRs
    =1X Avg. vol. of normal CTR
Avg. vol. of mCTR
    = 4X Avg. vol. of normal CTR CAS value for this tumor sample =
$$\frac{250}{100} + \frac{30}{100} + 1 + 4 = \text{value} > 3.$$

FIGURE 3

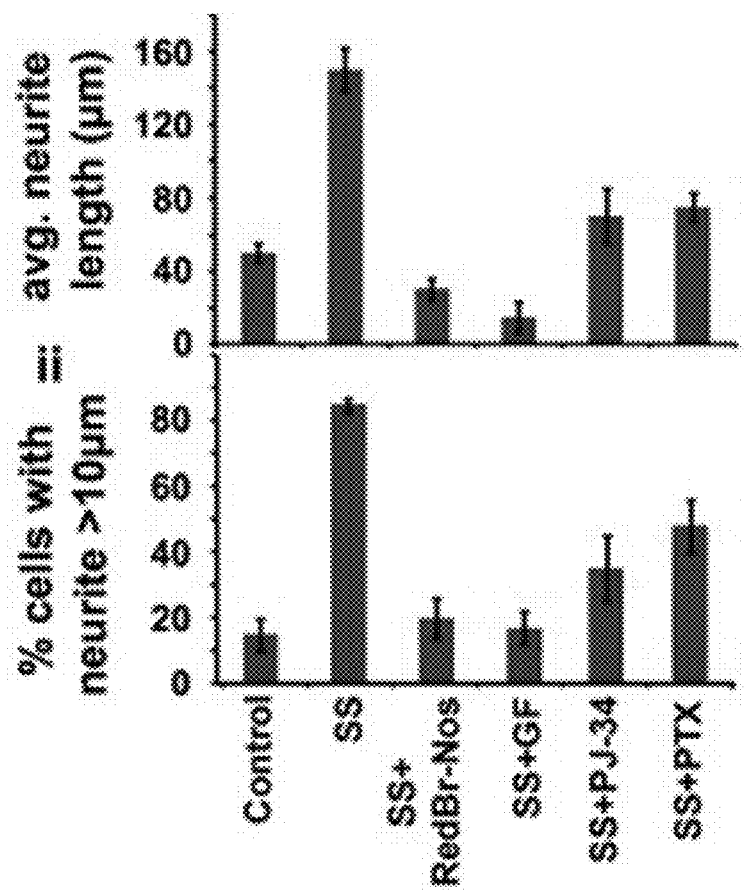
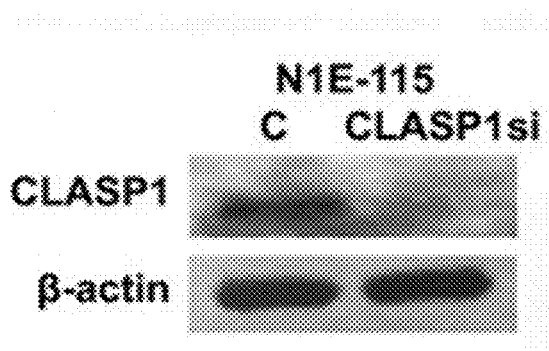
FIGURE 18

METHOD FOR DETERMINING THE RISK PROFILE OF NEOPLASTIC TISSUE

This application is a continuation application of U.S. patent application Ser. No. 14/632,778, filed Feb. 26, 2015, claims priority to U.S. patent application Ser. No. 61/946,462, filed Feb. 28, 2014. The entirety of the aforementioned applications are incorporated herein by reference.

This invention was made with government support under grant number NIH NCI 1 UO1 CA179671 awarded by the National Institutes of Health. The government has certain rights in the invention.

FIELD

The present invention relates generally to methods for determining the risk profile of neoplastic tissue. The methods can be at least partially automated and computer-aided, to predict cancer outcome and more particularly to methods of assessing features of centrosomes and generating from those features one or more centrosome amplification scores (CAS) for determining a patient's risk profile and formulating an effective treatment regimen.

BACKGROUND

Centrosomes are cellular organelles that include two centrioles enclosed in a proteinaceous mass called the pericentriolar matrix (PCM). Centrosomes, by nucleating and organizing the cell's microtubular cytoskeleton, play a key role in regulating cell structure, directional cell migration and tissue polarity. Centrosomal defects, termed centrosome amplification (CA), can arise from various aberrant processes, including cell-cell fusion, centrosome fragmentation, de novo centriole formation, dysregulation of the canonical centrosome duplication cycle, and possibly cytokinesis failure. In addition to exhibiting numerical abnormalities, amplified centrosomes are oftentimes abnormal in structure, function, or localization within the cell.

While the mechanisms underlying centrosome amplification (CA) and their consequences are not entirely understood, CA is largely considered a hallmark of cancer cells, but a rare phenomenon in normal or benign tissue. CA is thought to play a key role in the development of cancer, and it is causally linked to chromosomal instability during tumor development and the generation of the genetic diversity that underlies other malignant phenotypes. Notably, CA occurs in pre-cancerous and pre-invasive lesions, suggesting that it may play an early, causal role in driving tumor progression and contributing to metastatic risk. CA is postulated to translate into a greater risk for initiation of malignant transformation, tumor progression and poor patient prognosis. CA has been detected in both solid and haematological cancers. For instance, CA has been detected in malignant human cells in a variety of tissues including breast, prostrate, lung, brain, colon, bladder, kidney, cervix, testis, ovary, liver, pancreas, head and neck, and blood.

Several methods and prediction tools are readily available in the field of oncology. These prediction tools are used to assist physicians, oncologists and cancer patients in calculating various components of cancer risk. The present methods also concern risk but are more focused on the risk of a benign tumor progressing to malignancy or the risk associated with a tumor diagnosed to be malignant (e.g., the risk of rapid tumor progression into metastasis, the risk of recurrence and poor outcomes in general for an individual patient). In many cases, present methods require a myriad of information depending on the cancer type. Moreover, it is becoming increasingly recognized that every cancer patient's disease is unique and only personalized medicine can yield the most optimal outcomes.

Typically, CA is not included in any of the tools for assessment of risk associated with a tumor even though amplified centrosomes have long been associated with more aggressive tumor characteristics. Most CA studies focus only on the numeric alterations as the key marker for CA and neglect to consider both numeric aberrations along with structural defects. A facile method of quantifying CA (both numerical and structural aspects of CA) reliably and accurately in various tumors is urgently needed to provide a foundation for centrosome status-based risk assessment. The present application addresses a need for better tools in assessing risk associated with tumors and providing adequate treatment therefore.

SUMMARY

The present application is based, in part, on the development of a quantitative method that can be carried out in a range of tissue types in the field of oncology to predict the risk for malignant transformation, tumor progression, chemoresistance and individual patient prognosis. A method to quantitate the numeric and structural degree of CA within tumor samples of multiple types has been developed. The method includes a protocol for determining one or more CA scores (CAS) in normal and/or cancer cells using a standardized, quantitative method, which can be computer-aided. The method has clinical utility even where the tissue availability is limited and has broad application across a range of cell types and tissue sources, and can be used: (i) to better inform clinicians about the risk associated with a tumor and therefore, the best course of therapy; (ii) to improve treatment outcomes and ultimately patient survival; and (iii) provide a basis for improved treatment of cancer. Unlike prediction tools used to date, the method of quantifying CA in tumors described herein takes into account both structural and numerical aberrations in CA and can be applied to both solid and hematological cancers.

Based on studies to date, quantification of CAS in tumor samples has established CA as a quantifiable cellular property/trait that can provide a determination of the frequency and severity of numeric and structural centrosomal aberrations and the risk associated with a tumor (especially in the early stages of a tumor's development when therapeutic intervention is most successful).

The methods and systems described herein utilize a counting approach wherein each centrosome or centrosome cluster is assigned to a nearby nucleus. In addition, 3D imaging, volume rendering and detailed image analysis is employed to analyze the volume of each centrosome. The inventive method further involves a key transformative step of classifying centrosomes into individually distinguishable centrosomes (iCTRs) and megacentrosomes (mCTRs). Although these types of aberrations often occur together, their biological origin and clinical consequences may be different. These two different types of aberrations can make potentially different contributions to the development and progression of cancer, hence the classification scheme herein facilitates quantitation of these types of aberrations separately. For each cell, a measure of the severity of centrosome amplification (numerical or structural) with reference to a normal centrosome numbers and volumes may be determined. In addition, for each sample, the frequency of numerical and structural amplification may be quantitated through calculation of CA score for iCTRs ($CAS_i$) and CA score for mCTRs ($CAS_m$), respectively. Scaling factors may be included in algorithms described herein to ensure that $CAS_i$ and $CAS_m$ have the same weight in the cumulative CA score ($CAS_{total}$).

Accordingly, in a first aspect, the application provides a method of computing the risk profile of a neoplastic tissue in a patient. The method can include the steps of (a) processing a sample of tumor tissue or cancer cells from the patient in a form suitable for visualization and demarcation of cell nuclei, individually distinguishable centrosomes (iCTRs) and megacentrosomes (mCTRs) in a region of interest (ROI) defined by a plurality of cell nuclei; (b) determining the numbers of iCTRs and mCTRs associated with each cell nucleus in the ROI; (c) determining the volume of each mCTR in the ROI; and (d) calculating one or more centrosome amplification scores (CASs) values for the sample based on steps (b) and (c), wherein the one or more CASs indicate the severity of centrosome amplification, the frequency of centrosome amplification, or both, and wherein the one or more scores provide a measure of a level of risk and/or a prognosis associated with the neoplastic tissue.

In some embodiments, step (b) comprises the substep of determining an average number of iCTRs per cell nucleus among cell nuclei associated with more than two centrosomes and determining a percentage of cell nuclei associated with more than two centrosomes among all demarcated nuclei in ROI. In other embodiments, step (c) comprises the substep of determining an average volume deviation of mCTRs among cell nuclei associated with mCTRs and a percentage of cell nuclei associated with mCTRs among all demarcated nuclei in ROI.

In other aspects, the invention features computer software programs and computer-aided systems for determining one or more centrosome amplification scores based on the method described above.

BRIEF DESCRIPTION OF THE DRAWINGS

FIG. 2 illustrates exemplary ROIs demarking cell nuclei, iCTRs and mCTRs, in tumor tissue (panel A) and normal tissue (panel B).

FIG. 3 illustrates a sample calculation of $CAS_{total}$ scores according to formula I.

FIG. 5 depicts $CAS_{total}$ values from normal breast epithelial tissue (N) and Grade 1 breast tumor tissue (T) obtained from Caucasian (Cau) and AA samples. FIG. 6 depicts immunoblots of known centrosome amplification markers in MDA-MB-231 (Caucasian), MDA-MB-468 and HCC-70 (AA cell lines). FIG. 7 depicts Kaplan-Meir survival curves indicating poorer progression-free survival of "high CAS" patients (with more centrosomal aberrations) when compared to "low CAS" patients.

increases in average CA over controls. To calculate average CA, the sum of percentage of (interphase or mitotic) cells showing CA at the 6, 12, 18, and 24 h time points was divided by 4. Panel B depicts the sum of average CA (interphase plus mitotic) observed when 231 cells were treated with RBN, BN, and PJ, compared with the treatment of HeLa and PC3 cells with the same three drugs.

Figure 13:
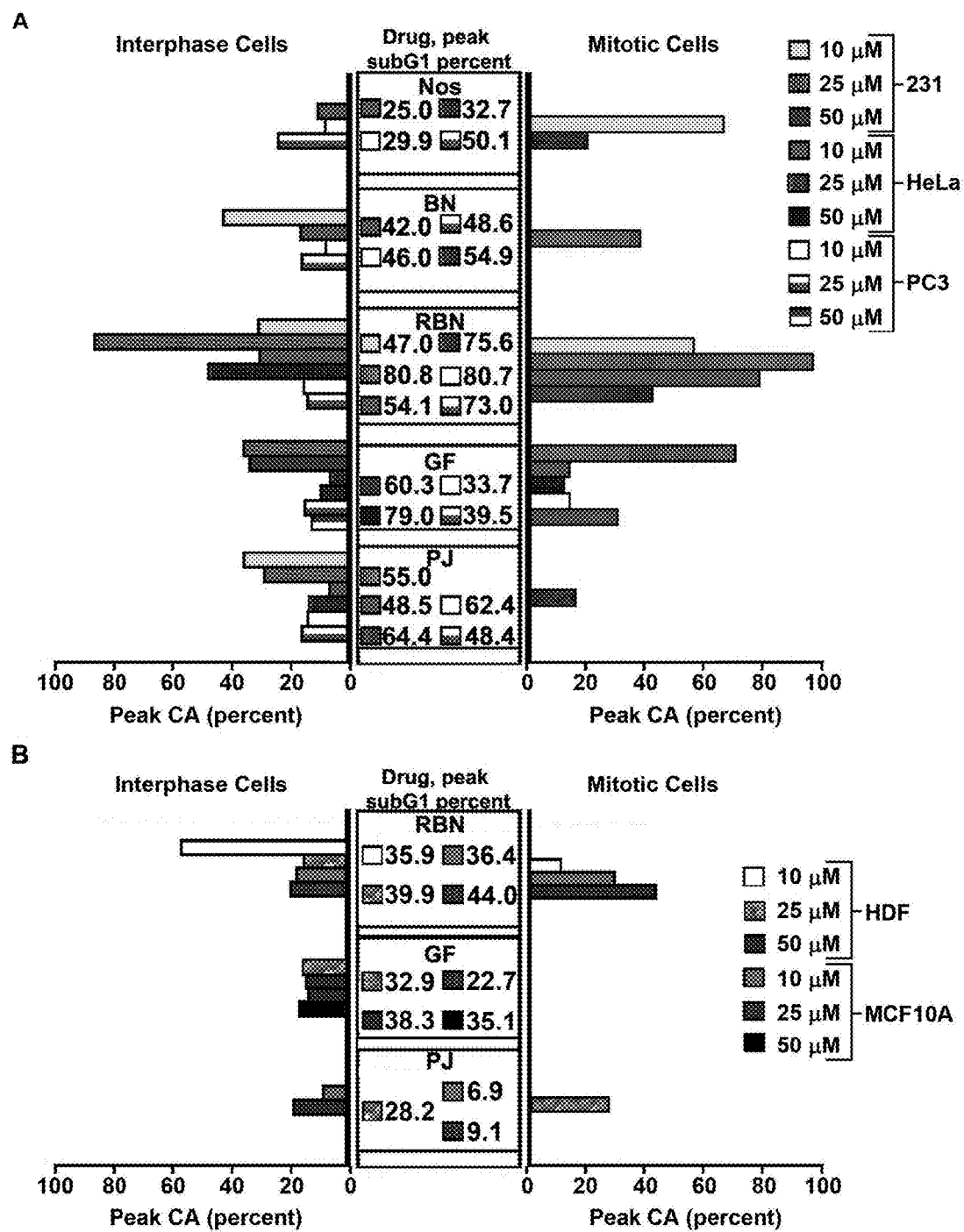

FIG. 13 shows peak induction of CA and subG1 in cancer cell (Panel A) and non-malignant (Panel B) cell lines. Only statistically significant changed values are depicted.

Figure 14:
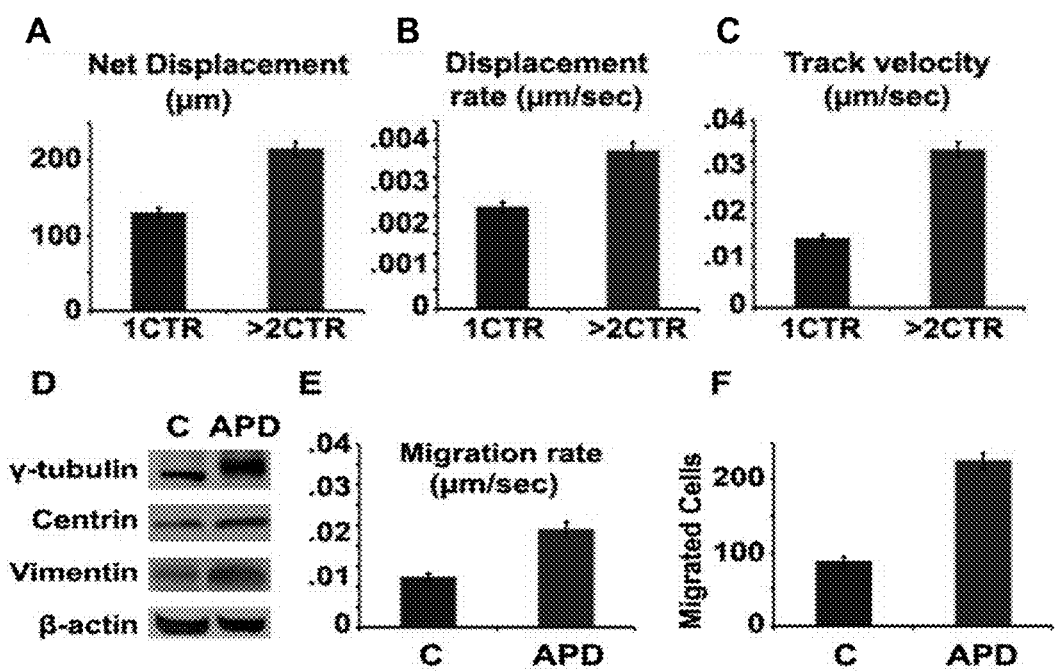

FIG. 14 shows a positive correlation between that chromosome amplification and cell migration. Trajectories of 10 cells each were captured over 18 h with 108 images per movie (6 frames/h). Data were analyzed using Volocity3.0 software (Improvision, Coventry, UK), whereby average net displacement, displacement rate and velocity measurements were generated for the identified cell tracks with respect to cell centroids. Quantitation of net displacement (Panel A), displacement rate (Panel B) and track velocity (Panel C) for cells with 1 and >2 centrosomes are shown as bar graphs. Panel D shows immunoblots probed for centrosomal markers ($\gamma$-tubulin and centrin) and a metastasis marker (vimentin) in ZR-75-30 cells treated with aphidicolin (APD), a reversible inhibitor of eukaryotic nuclear DNA replication. Panel E depicts a bar graph showing quantitation of migration rate of treated and untreated ZR-75-30 cells in a wound healing assay. Panel F depicts a bar graph showing the number of migrated cells in a Boyden chamber assay performed with aphidicolin-treated (APD) and untreated (C) ZR-75-30 cells.

Figure 15:
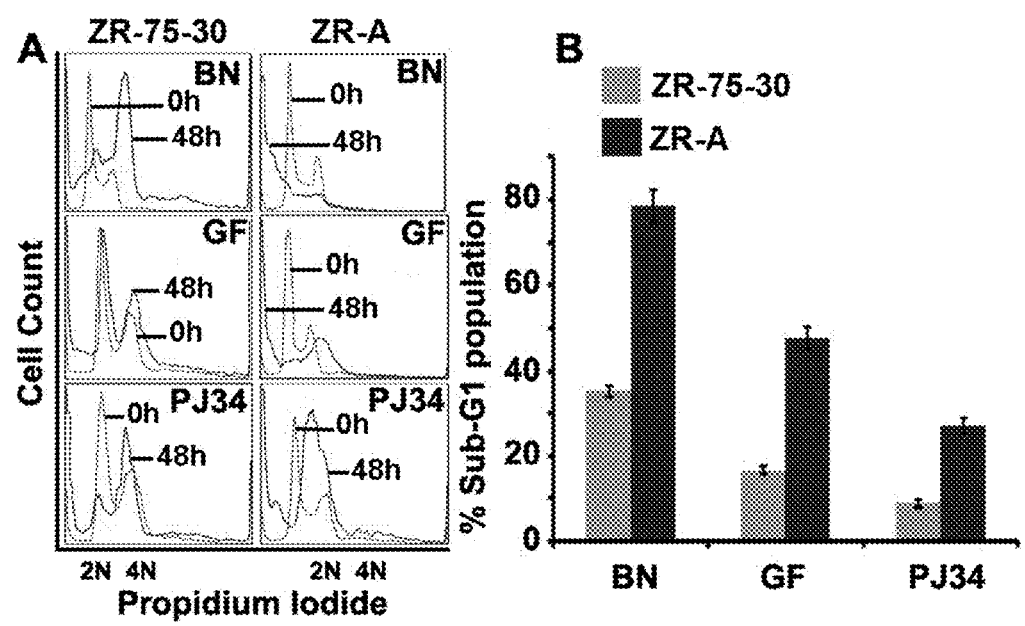

FIG. 15 shows ZR-75-30 breast cancer cells with amplified centrosomes (following aphidicolin treatment, i.e., ZR-A) have enhanced sensitivity to centrosome-disrupting drugs compared to parent ZR-75-30 cells (without aphidicolin treatment). Panel A depicts representative DNA histograms comparing cell-cycle kinetics of ZR-75-30 cells and ZR-A cells treated with bromonoscapine (BN, 25 µM), griseofulvin (GF, 25 µM) or PJ34 (25 µM), respectively for 48 h. X-axis shows DNA amounts showing different cell-cycle phases and Y-axis shows number of cells containing that amount of DNA. Panel B depicts a quantitative comparison of sub-G1 population in ZR-75-30 and ZR-A cells upon treatment with the three drugs with the same concentration (25 µM) for the same duration (48 h).

Figure 16:
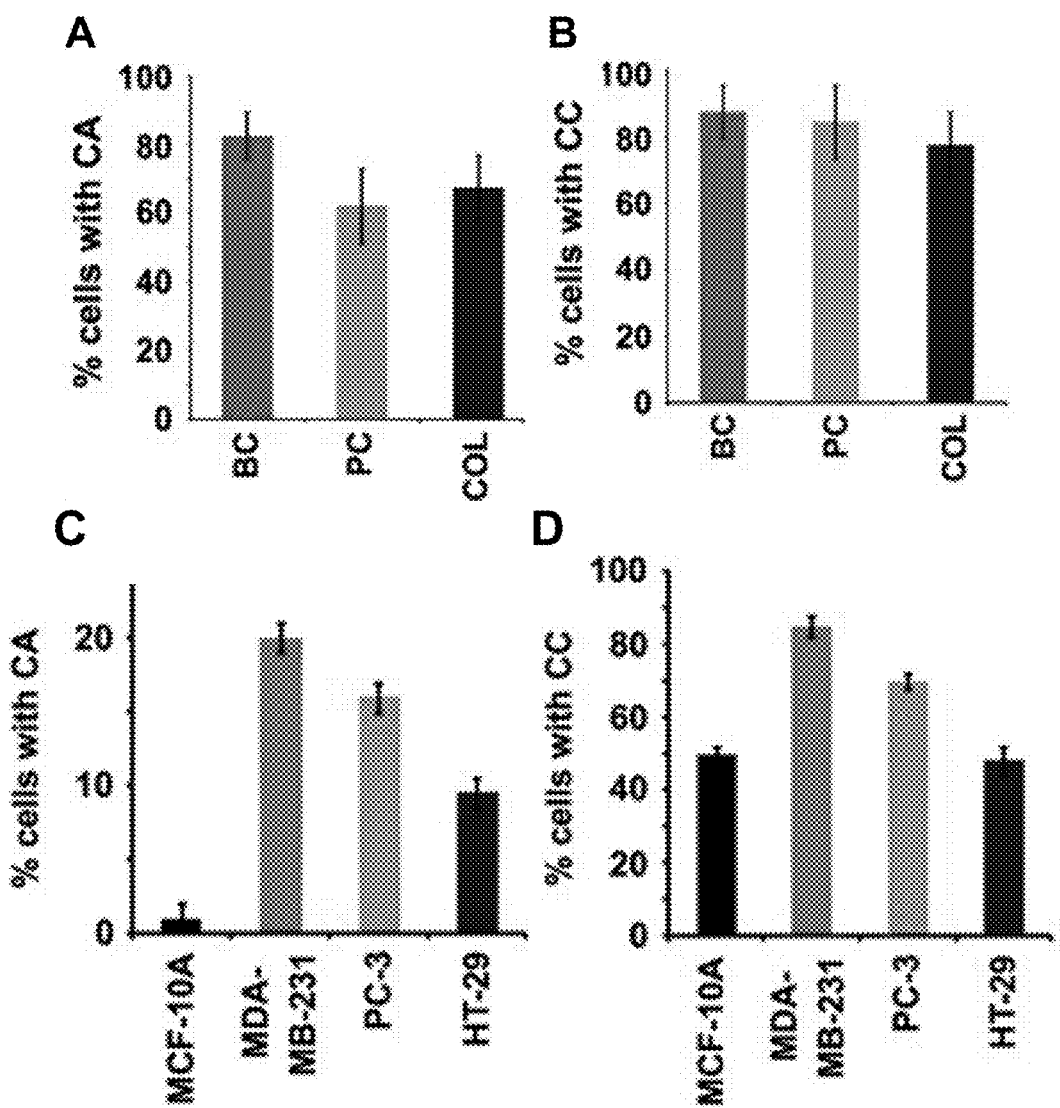

FIG. 16 depicts rampant centrosome amplification and clustering in the interphase cells of clinical tumors. Panels A and B depict quantitative bar graphs representing the percentage of CA and the percentage of interphase cells with amplified centrosomes that exhibit centrosome clustering (CC), respectively, in the corresponding patient tissue samples. Centrosomes were counted in interphase cells from randomly selected fields totaling at least 200 cells per sample. Panels C and D depict quantitative bar graphs representing the percentage of centrosome amplification and the percentage of cells with amplified centrosomes that exhibit centrosome clustering, respectively, in the corresponding cell lines. Centrosomes were counted in interphase cells from randomly selected fields totaling at least 200 cells per cell line. P<0.05. Scale bar, 5 µm. BC=breast cancer, PC=prostate cancer, COL=colon cancer.

Figure 17:
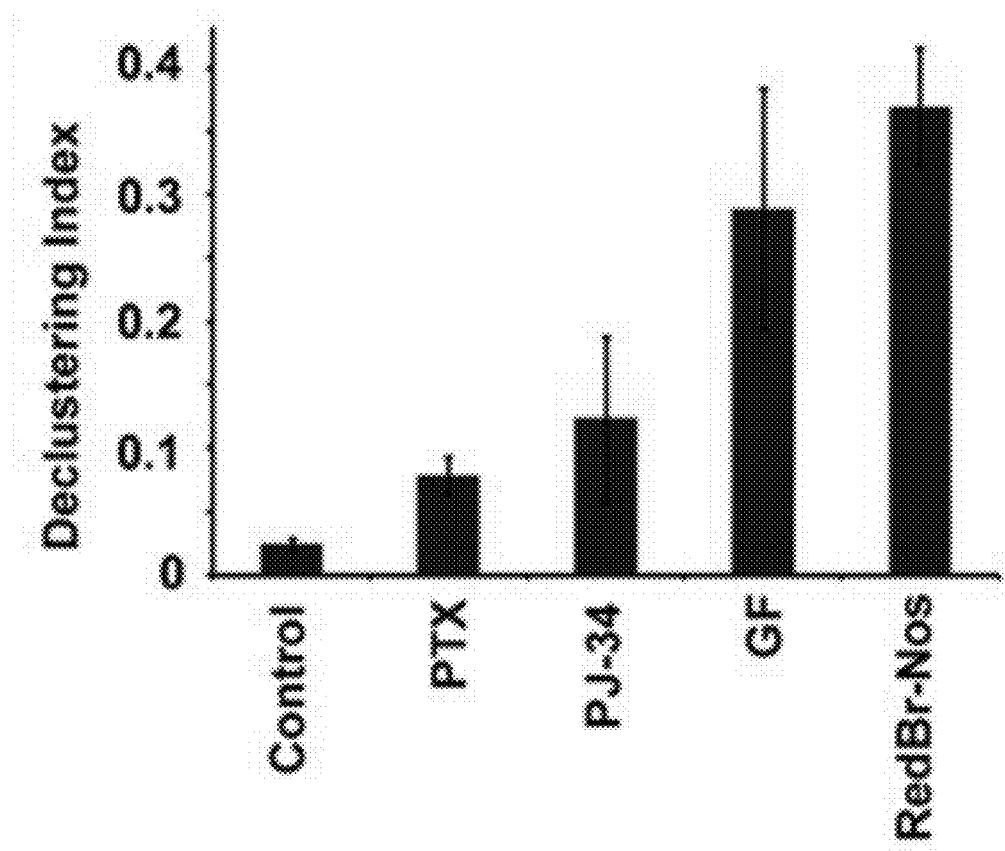

FIG. 17 shows a quantitative bar graph showing declustering indices for various centrosome-declustering agents (reduced-9-bromonoscapine (RedBr-Nos at 10 µM), griseofulvin (50 µM), PJ-34 (25 µM)) and the tubulin-polymerizing drug, paclitaxel (0.1 µM) following treatment of control and murine neuroblastoma N1E-115 cells.

FIG. 18 shows inhibition of neuritogenesis by centrosome-declustering agents. N1E-115 cells grown in serum-starved (SS) medium were evaluated to determine the extent of neurite formation after 48 h of treatment with RedBr-Nos (5 µM), Griseofulvin (10 µM), PJ-34 (10 µM), Paclitaxel (0.05 µM) treatment or untreated control cells (i.e., serum-starved medium (SS) alone). Panels Ai and Aii depict quantitative bar graphs representing the average length of neurites and percentage of population of cells showing neurite length >10 µm, respectively. A hundred cells were counted in each case. P<0.05. Panel B depicts an immunoblot showing CLASP1 expression levels in control (C) and CLASP1 siRNA-transfected N1E-115 cells.

Figure 19:
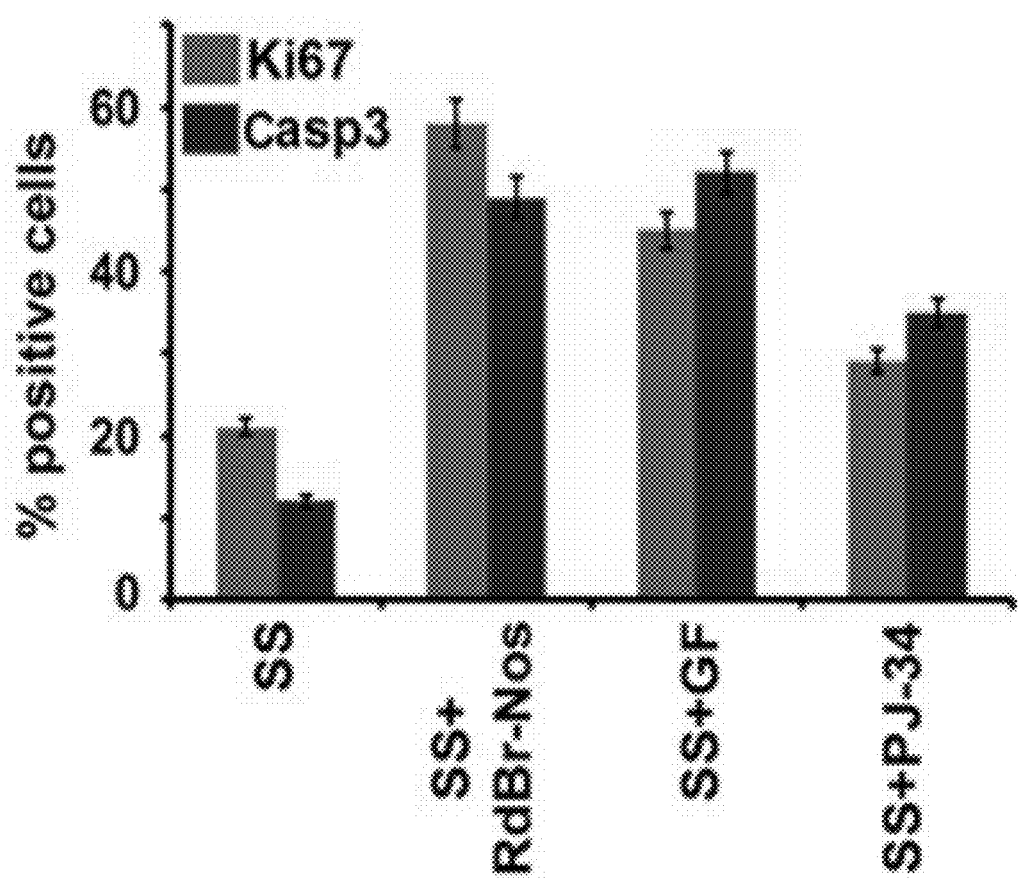

FIG. 19 shows quantitative bar graphs representing the percentage of Ki67- and caspase-3-positive N1E-115 cells in serum starved (SS) medium following treatment with RedBr-Nos (5 µM), Griseofulvin (10 µM), PJ-34 (10 µM) or untreated control cells (i.e., SS medium alone) to illustrate that inhibition of migration induces interphase cell death or pushes cells into a proliferative cell state. Two hundred cells were counted in each case. P<0.05.

DETAILED DESCRIPTION

A protocol for determining centrosome amplification scores (CAS) in neoplastic tissue (such as cancer or benign tumor) and in treating cancer patients is provided herein. The accompanying descriptions serve to illustrate, but do not limit, the invention.

As used herein, the term "neoplastic tissue," "neoplastic cells," or "neoplasms" refers to an abnormal mass of tissue or a proliferation of cells. The growth of neoplastic cells exceeds that of normal tissue around it and it is not coordinated with that of the normal tissue around it. Neoplasms may be benign (e.g., benign tumor and atypical hyperplasia), pre-malignant (e.g., carcinoma in situ and pre-cancer) or malignant (e.g., cancer). This tissue can originate from any cell type or tissue found in a mammal, including, but not limited to hepatic, skin, breast, prostate, neural, optic, intestinal, cardiac, vasculature, lymph, spleen, renal, bladder, lung, muscle, connective, tissue, pancreatic, pituitary, endocrine, reproductive organs, bone, and blood. In some embodiments, the neoplastic tissue is a breast cancer tissue. In other embodiments, the neoplastic tissue is a breast tissue with atypical hyperplasia.

As used herein the term "cancer" refers to any of the various malignant neoplasms characterized by the proliferation of cells that have the capability to invade surrounding tissue and/or metastasize to new colonization sites, including but not limited to leukemias, lymphomas, carcinomas, melanomas, sarcomas, germ cell tumors and blastomas. Exemplary cancers include cancers of the brain, bladder, breast, cervix, colon, head and neck, kidney, lung, non-small cell lung, mesothelioma, ovary, prostate, stomach and uterus, leukemia and medulloblastoma.

The term "leukemia" refers to broadly progressive, malignant diseases of the blood-forming organs and is generally characterized by a distorted proliferation and development of leukocytes and their precursors in the blood and bone marrow. Leukemia diseases include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

The term "carcinoma" refers to a malignant new growth made up of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

The term "sarcoma" generally refers to a tumor which arises from transformed cells of mesenchymal origin. Sarcomas are malignant tumors of the connective tissue and are generally composed of closely packed cells embedded in a fibrillar or homogeneous substance. Sarcomas include, for example, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilns' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphomas (e.g., Non-Hodgkin Lymphoma), immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma subungal melanoma, and superficial spreading melanoma.

Additional cancers include, for example, Hodgkin's Disease, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, premalignant skin lesions, testicular cancer, thyroid cancer, neuroblastoma, esophageal cancer, genitourinary tract cancer, malignant hypercalcemia, cervical cancer, endometrial cancer, and adrenal cortical cancer.

I. Methods for Determining Risk Profiles in Patients With Neoplastic Tissue

Figure 1:
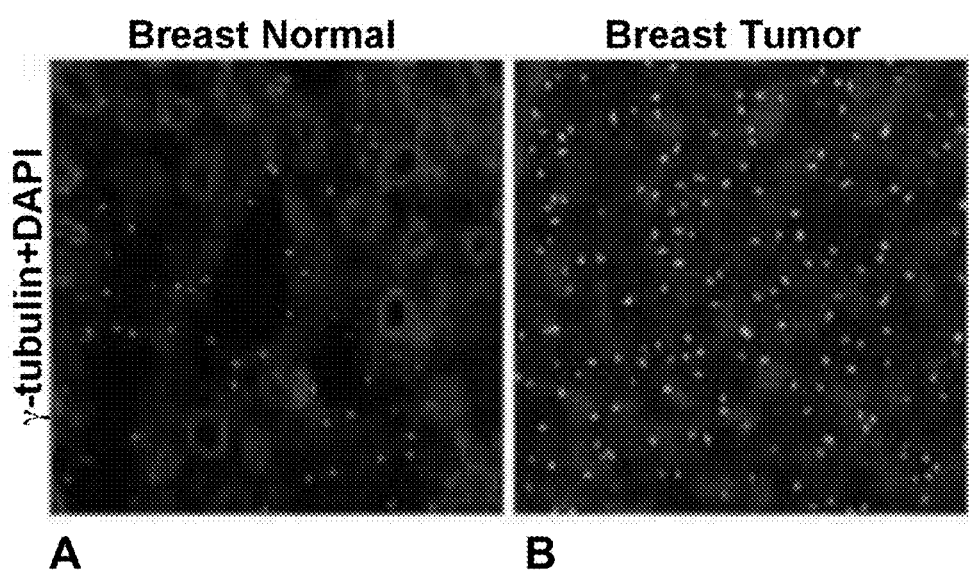
FIG. 1 is a pair of photomicrographs illustrating sections of normal breast (panel A) and breast tumor tissue (panel B) stained with an antibody against y tubulin and DAPI. From images such as these, one can select a region of interest (ROI).

FIG. 1 depicts a pair of photomicrographs illustrating sections of normal breast (Panel A) and breast cancer tissue (Panel B) stained with an antibody against the centrosomal marker γ tubulin, and the nuclear stain DAPI. The high degree of staining in the breast cancer tissue is a reflection of centrosome amplification in these cells. Centrosomes can be categorized into either of two types: individually distinguishable centrosomes (iCTRs) and megacentrosomes (mCTRs). iCTRs are centrosomes that stain positive for γ-tubulin, with centrosomes numbers and boundaries clearly distinguishable and volumes that lie within the range of centrosome volumes found in normal tissue (e.g., 0.23-0.76 cubic microns for breast tissue immunostained for γ-tubulin). mCTRs are centrosomes in a neoplastic region that stain positive for γ-tubulin and whose volume is greater than the upper limit of the centromere volume range found in corresponding normal tissue (e.g., 0.76 cubic micron for breast tissue immunostained for γ-tubulin). mCTRs could either be centrosomes with aberrantly large volumes or could represent a situation wherein multiple centrosomes are clumped together so closely that their precise numbers and boundaries cannot be discerned or resolved (see e.g., FIG. 2, Panel B).

As used herein, the term "normal centrosomes" refers to centrosomes found in normal tissue (including adjacent non-involved tissue in a tumor core biopsy or resected tumor tissue) and stain positive for γ-tubulin, with numbers and boundaries clearly distinguishable and volume not exceeding the normal range of centrosomes of the corresponding tissue or cell type. For each tissue type, the normal range of centrosome volumes is determined from a large cohort of normal tissue samples. For example, centrosome volumes (as determined by immunostaining for γ-tubulin) in normal breast tissue range from 0.23 to 076 cubic microns; in normal pancreatic cell tissues from 0.20 to 0.56 cubic microns; and in normal bladder cell tissues from 0.35 to 0.74 cubic microns.

Generally, most normal somatic tissues average between 1-2 normal centrosomes per nucleus and no mCTRs. By contrast, cancer cells may have >2 iCTRs and several mCTRs per nucleus. The present application is predicated on the discovery that three-dimensional analysis of iCTRs and mCTRs in cancer cells can provide a useful tool for determining a risk profile of cancer in a patient to facilitate a more risk-adapted and optimal course of treatment.

In one embodiment, the method includes the step of processing a sample of neoplastic tissue from the patient to facilitate three dimensional visualization and demarcation of cell nuclei, iCTRs and mCTRs in a region of interest (ROI) defined by a plurality of cell nuclei. Three dimensional image data is generated so as to provide volume rendering of the iCTRs and mCTRs. In some embodiments, the 3D image is produced by confocal imaging of immunofluorescently stained centrosomes. In other embodiments, immunohistochemical (IHC) staining methods (e.g., HRP-based detection with hemotoxylin counterstain) are used to produce 3D image of centrosomes. Imaging of the centrosomes (brown colored dots) will be done using a bright field imaging system with optical sections (i.e., z-stacks) followed by image deconvolution, to enable software-assisted 3D volume rendering. Centrosome volume range as determined in the immunohistochemically stained normal tissues will be used to determine iCTRs and mCTRs in the tumor tissues. Images could either be obtained from 10-15 microscopic fields of view for each sample or by whole-slide imaging as long as optical sections are acquired for 3D volume rendering. For slides stained immunofluorescently for centrosomes, imaging is carried out in areas determined to be "tumor areas" based on comparison with a serial section stained with hematoxylin eosin (wherein tumor areas are pre-marked). In slides stained immunohistochemically for centrosomes, only iCTRs and mCTRs in tumor areas will be analyzed for CAS determination.

From this image data, the following are determined:
(i) the number of iCTRs and mCTRs associated with each cell nucleus in the ROI,
(ii) the volume of each iCTR and mCTR associated with each cell nucleus in the ROI,
(iii) the average number of excess iCTRs (i.e., iCTRs in excess of 2) amongst cells that have >2 centrosomes; this gives a measure of the "severity" of numerical amplification present in the cells that bear numerically amplified centrosomes,
(iv) the percentage of cell nuclei that have excess iCTRs (i.e., iCTRs in excess of 2); this gives a measure of the "frequency" or "prevalence" of numerical centrosome amplification,
(v) the average volume deviation (compared to the upper limit of the volume of normal centrosomes) of mCTRs among the cells that bear mCTRs; this gives a measure of the "severity" of structural amplification present in cells that bear structurally amplified centrosomes or mCTRs,
(vi) the percentage of cell nuclei that have mCTRs associated with them; this gives a measure of the "frequency" or "prevalence" of structural amplification of centrosomes.

Based on these numerical and structural determinations, one or more CASs are determined as further described below. The scores indicate the severity of centrosome amplification, the frequency of centrosome amplification, or both, in the sample and provide a measure of the level of risk associated with the neoplastic tissue.

II. Processing of Tissue Samples and Methodology for Analysis

Cell and tissue sources: Any cell or tumor cell type can serve as a cell or tissue sample for the inventive method, including those described above. Cells can originate from many different sources, including the breast, prostrate, lung, brain, colon, bladder, kidney, cervix, testis, ovary, liver, pancreas, head and neck, anogenital tissue, adrenal gland, and blood. Typically, the cell sample is derived from tumor tissue that was surgically removed from a human patient or other mammal.

Biopsy techniques. A variety of biopsy techniques may be used to obtain a cell or tissue sample such as, but not limited to excisional (i.e., removal of an entire lesion) or incisional (i.e., where a portion or wedge of tissue is removed). In some cases, a fine-needle may be required to withdraw cellular material from a tissue mass using aspiration techniques (e.g., aspiration biopsy). Further, cell or tissue samples may be cells isolated from any cell suspension, body fluid samples, or cells dislodged from tumor by any other means.

Preparation of tissue samples. In the present methods, normal and/or cancer tissue samples can be formalin-fixed paraffin-embedded or may be fresh-frozen in an OCT compound (such compounds are well-known in the art) and sectioned or fixed with methanol or any other appropriate fixative (such fixatives, processes and types are well-known in the art). Formalin-fixed, paraffin-embedded tissue must be subjected to de-paraffinization, peroxide quenching and antigen retrieval (e.g., heating under pressure in a citrate buffer) prior to the staining steps that allow visualization of centrosomes and nuclei within the sample.

Antibodies or binding agents: Cell samples may be stained with one or more antibodies, biologically active fragments thereof, and/or binding agents directed against pericentriolar matrix components. Preferably, the primary antibody or binding agent specifically binds an antigen, protein or component of the pericentriolar matrix (PCM) that shows substantial localization to centrosomes at all stages of the cell cycle (i.e., interphase, mitosis (including prophase, metaphase, anaphase, telophase) and cytokinesis). In some embodiments, the primary antibody or binding agent is conjugated to a fluorophore or quantum dot or enzyme, etc to facilitate visualization of signal. When using quantum dots, visualization of centrosomes and quantitation of CASs may be multiplexed with (or carried out simultaneously along with) visualization of other proteins in the same sample. In other embodiments, a secondary antibody or binding agent that binds to the primary antibody or binding agent is used to facilitate visualization. By colocalizing with centrosomes, the PCM binding agents produce a detectable signal above background so as to provide reliable image acquisition and 3D volume rendering. Volume rendering creates a binary image for volume determination.

Components of the PCM that localize to the PCM throughout the cell cycle include proteins include γ-tubulin, pericentrin, centromere protein J (CPAP/Sas-4) and ninein. Accordingly, these PCM components may be targeted using e.g., anti-γ-tubulin antibodies, including e.g., T3320, T-3195, T-3559, and C7604 (Sigma-Aldrich); ab11317, ab16504, ab27074 (Abcam); and sc-7396 (Santa Cruz Biotechnology); anti-pericentrin antibodies, including e.g., A301-348A, A301-349A and IHC-00264 (Bethyl Laboratories); ABT59 (EMD Millipore); ab4448, ab28144, ab99342, ab84542, ABIN968665, ABIN253211, ABIN253210, ABIN910327 (Abcam); CPBT-42894R11, CPBT-42892RH, CPBT-42891RN (Creative BioMart); sc-28145, sc-28143, sc-28144, sc-68928 (Santa Cruz Biotechnology), HPA016820, HPA019887 (Sigma-Aldrich); NB100-61071, NBP100-61072, NBP1-87771 and NBP1-87772 and (Novus Biologicals); anti-centromere protein J antibodies, including e.g., ABIN527721, ABIN527722 and ABIN527723 (Abcam); 101-10278 (Ray-Biotech); and CABT-22656MH (Creative BioMart); and anti-ninein antibodies, including e.g., ab52473, ab4447 (Abcam); 41-3400 (Life Technologies); orb100831 (Biorbyt); HPA005939 (Atlas Antibodies); sc-376420 and sc-292089 (Santa Cruz Biotechnology).

Alternatively, or in addition, the antibodies or binding agents may target one or more of the following: the nucleus of a cell, comprised of key structural components such as the nuclear envelope, nucleoplasm, nucleoskeleton, nuclear lamina (including lamin proteins, such as LEM3), RNA molecules, chromosomes, chromatin, including euchromatin and heterochromatin, nucleolus, and other subnuclear bodies (e.g., Cajal bodies, Gemini of coiled bodies or gems, RAFA domains, polymorphic interphase karyosomal association (PIK), promyelocytic leukaemia (PML) bodies, paraspeckles, splicing speckles and perichromatin fibrils). In other embodiments, the antibody or binding agent is an antibody or binding agent that is capable of binding to any subcellular organelle that is present as one copy per cell or whose number of copies per cell is constant and well-established.

Both fluorescence (direct and indirect) and immunohistochemical (IHC) staining methods may be employed for the purpose of staining centrosomes for visualization purposes. These staining methods may employ antibodies against suitable centrosomal markers, such as γ-tubulin. With fluorescence-based methods, a variety of different secondary antibodies may be used for detecting γ-tubulin, such as Alexa Fluor 555, Alexa Fluor 488, TRITC-conjugated, FITC-conjugated etc. In certain embodiments, an anti-pericentrin antibody may be used as the primary antibody for labelling centrosomes instead of anti-γ-tubulin antibody. In other embodiments, the primary antibody itself is conjugated to a fluorophore or quantum dots or an enzyme for enabling visualization. When using quantum dots, visualization of centrosomes and quantitation of CASs may be multiplexed with (or carried out simultaneously along with) visualization of other proteins in the same sample.

In certain embodiments, as an alternative to fluorescence-based detection of centrosomes, immunohistochemical (IHC) staining may be employed for imaging centrosomes. For example, an HRP-based detection system employing hematoxylin counterstain may be used for imaging centrosomes (as brown colored dots) using a brightfield imaging system with optical sections (i.e., z-stacks) followed by image deconvolution to enable software-assisted 3D volume rendering as further described below. Centrosome volume ranges may be determined from immunohistochemically stained normal tissues to aid in analysis of iCTRs and mCTRs in tumor tissues. Alternatively, an alkaline phosphatase-based detection system (producing red color instead of brown) may be used in place of the HRP-based system for IHC. In other embodiments, there could be variation in the primary antibody used for labelling centrosomes. For example, instead of using γ-tubulin, pericentrin may be used for labelling whole centrosomes.

In other embodiments, centriolar markers are used to stain centrioles and provide 3-dimentional information about centriolar volumes and structural aberrations.

Although the invention is not so limited, when any nuclear component or nuclear membrane component is targeted, the stain may be a fluorescent protein-based marker for the nucleus. Exemplary fluorescent protein-based nuclear markers include, but are not limited to CellLight Nucleus-Green Fluorescent Protein (C 10602), CellLight®Nucleus-RFG (Red Fluorescent Protein; 10603), CellLight®Nucleus-Cyan Fluorescent Protein and Alexa Fluor 488 conjugate of Histone H1 (H13188)); nuclear counterstains for live cells and unfixed tissues, such as Hoechst 33342 dye and SYTO dyes 40 (S11351), 11 (S7573), 13 (S7575), 12 (S7574), 14 (S7576), 16 (S7578), 17 (S7579) and 59 (511341)); nucleic acid stains, including dimeric cyanine dyes, and fluorescein-1 2-dUTP (C7604); 4',6-diamindino-2-phenylindole (DAPI; D1306, D3571, D21490); Hoechst stains, such as Hoechst 33258, Hoescht 34580, Hoechst S769121 (N21485) and Hoeshst 33342 (H1399, H3570 and H21492); BOBO-1 (B3582), BOBO-3 (B3586), SYTOX (S7020), SYTOX (Si 1368), SYTOX Blue (511348, S34857), YO-PRO-1 dye (Y3603), TOTO-1 (T3600), TOTO-3 (T3604), TO-PRO-3 (T3605), YOYQ-1 (Y3601), propidium iodide (P1304MP, P3566, P21493); and other chromosome banding dyes, including 7-aminoactinomycin D (7-AAD, A1310) and 9-amino-6chloro-2-methoxyacridine (ACMA, A1324).

In the present application, the antigen retrieval step was optimized for staining with the anti-γ-tubulin antibody. For antigen retrieval, the slide may be placed in 10 mM citrate buffer (0.05% Tween20, pH 6.0) and pressure cooked at 15 psi for 10 min in buffer (after preheating). The buffer jar containing a slide or slides is then placed on ice to cool for 30 minutes before proceeding to immunostaining. A suitable primary antibody for use in these studies is the monoclonal anti gamma-tubulin antibody produced in mouse (Sigma Aldrich, Catalog. No: T6557; dilution of 1:1000). A suitable secondary antibody for use is the Alexa Fluor 488 Goat Anti-Mouse IgG (H+L) Antibody (Life Technologies; Catalog no: A-11001; Lot no: 1397999; dilution of 1:2000). In addition, nuclei can be stained using 4',6-Diamidino-2-phenylindole dihydrochloride (DAPI) from Sigma Aldrich (Catalog no: D8417; Lot no: 072M4015V) and mounted in Prolong Gold antifade reagent (Life Technologies; Catalog no: P36930; Lot no: 1298408, 1478059, 1499272).

Samples imaging method. Centrosomes and nuclei may be visualized within multiple regions of interest (ROIs) using any form of microscopy suitable for facilitating three dimensional visualization of centrosomes and nuclei. Exemplary microscopic methodologies include, but are not limited to confocal laser scanning microscopy, spinning-disk confocal microscopy, confocal X-ray fluorescence imaging, electron microscopy, electron microscope tomography, IHC, 3D-SIM and the like.

Volumes of centrosomes, including iCTRs and mCTRs in individual cells are determined through 3D volume rendering using software-assisted image analysis. Typically for each field, 9-15 optical sections of 0.45 μM thickness each are acquired. Then, for each field of view, the optical sections are stacked to produce a "maximum intensity projection image". In scientific visualization, a maximum intensity projection (MIP) is a method that projects (onto the visualization plane) the voxels with maximum intensity that fall in the way of parallel rays traced from the viewpoint to the plane of projection. Using the MIP, a region of interest (ROI) is defined as a region wherein several nuclei (generally at least 10) and centrosomes are present. In each ROI, each nucleus is assigned to a centrosome or centrosome cluster until all nuclei in the ROI are taken into account, and any centrosome or centrosomal cluster without a nucleus associated with it is omitted. Any nucleus that is not completely visible is completely excluded (along with the centrosome(s) associated with it) from the ROI. After an ROI has been defined, image segmentation is carried out to identify all "centrosomes" as "objects". Segmentation involves defining two threshold parameters: the "low threshold value" and the "high threshold value". Low threshold value is the minimum fluorescence intensity required for the software to identify an object in the image as a centrosome. In some embodiments, the "low threshold value" is set to be in the range 85-95. High threshold value is set to be 255. Optionally, visual inspection is conducted to ensure that (a) all the "objects" selected by the software are truly centrosomes and not some background noise, and (b) that all centrosomes are actually identified by the software as "objects". In the event that any of the objects selected by the software are not true centrosomes, these objects are manually deselected. In the event that the software fails to identify some centrosomes as "objects", the "low threshold value" may need to be slightly adjusted to ensure that all centrosomes are indeed picked up by the software. This step results in the creation of a binary image with several "objects" whose volumes can then be determined by processing this data via a suitable 3D volume rendering software. In some embodiments, the imaging method further includes a normalization step utilizing one or more external standards (such as beads labeled with the same secondary antibody and fluorophore as the centrosome marker).

Exemplary imaging parameters for confocal imaging may utilize a 63X oil objective with a numerical aperture of 1.4. Images may be taken at 1.5× optical zoom. These parameters may be used to achieve e.g., an optical resolution in the range of 120 to 155 nm.

The raw 3D image data may be processed using a suitable 3D volume rendering software enabling a determination of the volume of each centrosome within each ROI. The term "volume rendering" refers to transforming a 2D image stack for 3D visualization and subsequent image analysis. Any suitable volume rendering software can be used for this step. Many commercially available software applications are available and are known in the art. The Axiovision 3D module extension (Zeiss) is a suitable software application for such volume measurements. Other suitable 3D rendering software applications may include, but are not limited to BioView3D volume renderer, an open source and cross-platform application; VolView, an open-source, intuitive, interactive system for volume visualization; 3D Slicer, a free, open source software package for scientific visualization and image analysis; Ambivu 3D Workstation, a commercial medical imaging workstation that offers a range of volume rendering modes (based on OpenGL); Amira, a commercial 3D visualization and analysis software for scientists and researchers (in life sciences and biomedical); Avizo, commercial 3D visualization and analysis software for scientists and engineers; ImageVis3D, an Open Source GPU volume slicing and ray casting implementation; MeVisLab, cross-platform software for medical image processing and visualization (based on OpenGL and Open Inventor); Open Inventor, a high-level 3D API for 3D graphics software development (C++, .NET, Java); ParaView, an open-source, multi-platform data analysis and visualization application; VoluMedic commercial volume slicing and rendering software; Volocity 3D Image Analysis Software; and 3D Doctor by Able Software Corporation, an advanced 3D image visualization, rendering and measurement software package designed for microscopy and related imaging applications.

In some embodiments, rather than imaging 10-15 randomly selected fields, whole-slide scanning may be employed. Tumor tissue slides pre-marked by a pathologist could be imaged as a whole. Hamamatsu Nanozoomer 2.0HT whole slide scanner is capable of multi-level scanning as z-stacks for both brightfield and fluorescence imaging. This can provide a faster means for scanning images as compared to imaging several distinct microscopic fields. When imaging immunohistochemically stained samples, brightfield z-stacks can be processed using deconvolution software to resolve background noise before feeding the data into the 3D volume rendering software. Different 3D volume rendering softwares can be used depending on the compatibility of the raw image files.

In certain embodiments, the analytical portion of the procedure may be initiated by using a low fluorescence intensity threshold value selected on the basis of the smallest visible centrosome in normal cell samples. The same value may then be used in the tumor cell samples. Based upon (i) whether the boundaries of a given centrosome are clearly distinguishable or not, and (ii) the volume of each centrosome, all the centrosomes in the ROI are then categorized as iCTRs or mCTRs using the criteria described above. Within each ROI, the number of iCTRs and/or mCTRs associated with each individual nucleus is recorded as 1i, 2i, 3i, etc. for iCTRs and 1m, 2m, 3m, etc. for mCTRs. The volume of each iCTR and mCTR is also recorded.

The volume range for a normal centrosome in a normal cell type may be determined by analyzing the volumes of at least 1000 iCTRs from normal (adjacent uninvolved) tissues of one or more patients. The smallest and largest values for centrosomal volume provide the "normal centrosome volume range" for that tissue (e.g., breast, prostate, etc.). By way of example, in breast tissue stained to visualize γ-tubulin, the normal centrosome volume range was found to range from 0.25-0.76 cubic microns. Since normal samples do not have mCTRs, this value is not calculated.

For images of tumor samples, the volume of all iCTRs and mCTRs are determined using the same (i) volume rendering software as for normal tissue, and (ii) fluorescence intensity threshold as for the corresponding normal tissue. Using the "normal centrosome volume range" determined for normal samples, centrosomes in the cancer sample are classified into iCTRs and mCTRs. For each ROI in the cancer tissue, the number of iCTRs and mCTRs associated with each nucleus within the ROI are recorded for analysis.

Centrosome Amplification Scores (CAS)

In one embodiment, a cumulative Centrosome Amplification Score (CAS total) is computed on the basis of the formula: $CAS_{total}=CAS_i+CAS_m$, where $CAS_i$ and $CAS_m$ are further defined as set forth in the following equation (I)

$$CAS\,Total = \boxed{\dfrac{\text{No. of iCTR}}{\text{No. of nuclei}} + \dfrac{\text{Avg. vol, of iCTR}}{\text{Avg. vol, of normal CTR}}}_{CASi} + \boxed{\dfrac{\text{No. of mCTRs}}{\text{No. of nuclei}} + \dfrac{\text{Avg. vol, of mCTR}}{\text{Avg. vol, of normal CTR}}}_{CASm} \quad (I)$$

In this case, $CAS_i$ reflects frequency of iCTR occurrences in nuclei in the sample tissue along with the average volume of iCTRs relative to the average volume of CTRs in the normal tissue counterpart. Likewise, $CAS_m$ reflects the frequency of mCTR occurrences in the nuclei along with the average volume of mCTR relative to the average volume of CTRs in the normal tissue counterpart.

To calculate a cumulative $CAS_{total}$ score in accordance with the above-described equation, the centrosomes may be immunostained with anti-γ-tubulin antibody, while the nuclei are stained with Hoeschst stain. Regions containing 20-25 clearly distinguishable nuclei can be selected and defined as regions of interest (ROI) by drawing a boundary around the outer edges of the outermost nuclei as shown in the accompanying panels in FIG. 2. To calculate the CAS for 10 ROIs in a tumor tissue, the number of individually distinguishable centrosomes (iCTRs) and megacentrosomes (mCTRs) are determined within these ROIs, as well as the average volumes of the iCTRs and mCTRs within these 10 ROIs are calculated. In addition, the number and volumes of normal centrosomes in 10 low power fields are determined for 10 ROIs from uninvolved normal tissue as in the tumor tissue. FIG. 3 includes a sample calculation of $CAS_i$ $CAS_m$ and $CAS_{total}$ scores according to the above-described equation.

In another embodiment, a cumulative $CAS_{total}$ score is similarly computed on the basis of the formula (IIa):

$$CAS_{total} = CAS_i + CAS_m \quad (IIa)$$

However, whereas $CAS_i$ similarly represents an aggregate value reflecting both frequency and severity of numerical centrosome amplification, the $CAS_i$ calculation is based on an algorithm that includes a scaling factor, among other things, to ensure that $CAS_i$ and $CAS_m$ contributions are given equal weight. Likewise, $CAS_m$ is an aggregate value of both frequency and severity of structural centrosome amplification, but is scaled relative to the volume range found in normal somatic tissue. In this manner, the contribution from the numerical and structural properties of centrosomes are accorded equal weight.

Specifically, to ensure that neither of the components of the CAS score, $CAS_i$ and $CAS_m$, are contributing disproportionately to the overall score, the original data is used to estimate values for the parameters $\beta_i$ and $\beta_m$ that would ensure that $CAS_i$ and $CAS_m$ on average would contribute equally to the overall score. It should be noted here that since the magnitude of the overall score is somewhat arbitrary (for example the score could be normalized to have a maximal value of 1), the more important issue is not the absolute number for $\beta_i$ and $\beta_m$, but their ratio. For breast tumor tissue immunostained for γ-tubulin, we found that when the value of $\beta_i$ was set to be at 0.02 or 2%, similar contributions from $CAS_i$ and $CAS_m$ was achieved by setting the $\beta_m$ value at 0.2 or 20%.

In some embodiments, statistical analysis is used on larger data sets to determine the optimal values of $\beta_i$ and $\beta_m$ (or more precisely their ratio) for each individual cancer type, such that it results in equal contributions from these two components of the overall CAS score. Also, in order to make the CAS algorithm more reflective of the "real" contributions of $CAS_i$ and $CAS_m$ individually towards clinical outcome prediction, the prognostic power of $CAS_i$ and $CAS_m$ may be determined separately based on their hazard ratio, in a much larger cohort of patients. Determination of prognostic power associated with $CAS_i$ and $CAS_m$ individually will allow the determination of their respective weighted contributions in the $CAS_{total}$ algorithm. This may again lead to a change in $\beta_i$ and $\beta_m$ values.

As used herein, the term "hazard ratio" refers to an estimate of the ratio of the hazard rate in one group versus that in a second group. The hazard rate is the probability that if the event in question has not already occurred, it will occur in the next time interval, divided by the length of that interval. The time interval is made very short, so that in effect the hazard rate represents an instantaneous rate. For instance, in a clinical trial where disease resolution is the endpoint, the hazard ratio indicates the relative likelihood of disease resolution in treated versus control subjects at any given point in time (see, e.g., D. R. Cox. Journal of the Royal Statistical Society. Series B (Methodological), Vol. 34, No. 2. (1972), p. 187-220; and S. L. Spruance, et. al., Antimicrobial Agents and Chemotherapy, (2004), p. 2787-2792).

In this embodiment, $CAS_i$ represents a numerical centrosome amplification component (i-component) defined by the following formula (IIb):

$$CAS_i = \text{Average}\left(\dfrac{N_i - 2}{R_i}\right)\dfrac{\text{percentage}(N_i > 2)}{\text{scaling factor } i} == \quad (IIb)$$

$$\left(\dfrac{\sum_{j=1, N_j > 2}^{N}(N_{ij} - 2)}{\sum_{j=1, N_j > 2}^{N}(1)} \cdot \dfrac{1}{R_i}\right) \cdot \dfrac{p_i}{\beta_i} =$$

$$\left(\left(\dfrac{\sum_{j=1, N_{ij} > 2}^{N} N_j}{\sum_{j=1, N_j > 2}^{N}(1)} - 2\right) \cdot \dfrac{1}{R_i}\right) \cdot \dfrac{\sum_{j=1, N_{ij} > 2}^{N} 1}{N} \cdot \dfrac{1}{\beta_i}$$

Where:
  $p_i$ is the percentage of cells for which the number of individually distinguishable centrosomes (iCTRs) exceeds the threshold value of 2. This ensures that only cells whose centrosomal copy number exceeds the upper limit of that seen in most normal somatic cells (normal somatic cells usually have only 1 or 2 iCTRs) are included in the CAS analysis.
  $\beta_i$ is a scaling factor that may be used to ensure that both $CAS_i$ and $CAS_m$ are given equal weight in the formula for $CAS_{total}$. This value might change depending on the tissue type being evaluated (e.g., tissue derived from breast, prostate, bladder, colon, lung, etc.) and the data itself (the range observed for severity and frequency of numerical and structural CA observed in different cancer types such as in breast cancer vs. bladder cancer vs. prostate cancer, etc. . . . ). By way of a hypothetical example, in colon cancer, $CAS_i$ can range from 2-5 and $CAS_m$ from 6-12. In that case, $CAS_m$ would be preferably scaled down and $CAS_i$ scaled up so that they contribute equally to $CAS_{total}$. In another cancer type, such as prostate cancer, $CAS_i$ could range from 7-9 and $CAS_m$ from 2-5. Thus, the scaling factors may differ depending on the cancer type and the range of $CAS_i$ and $CAS_m$ values observed in this cancer type.

$R_i$ is the range for normal distribution, in this case $R_i=2-1=1$.

Ni is the number of iCTRs in a cell that contains more than 2 iCTRs.

N is the total number of cells analyzed in the sample.

The index j is an implementary term that takes the values $\{1, 2, 3, \ldots, N\}$, that is, from 1, 2 all the way up to N.

The symbol i in Ni is used to indicate taking the average over cells with numerical centrosome amplification. This means that the "severity" term of CAS, provides the average number of excess iCTRs (i.e., iCTRs in excess of 2) amongst cells that have >2 centrosomes; this therefore gives a measure of the "severity" of numerical amplification present in the cells that bear numerically amplified centrosomes (it answers the question, "Among cells with >2 centrosomes, how severe is the numerical amplification?"). Note that only cells with >2 centrosomes are taken into consideration in the formula above. The "severity" component of $$CAS_i \left(\text{i.e., Average}\left(\frac{N_i - 2}{R_i}\right)\right)$$

is based on a determination of how "severe" the numerical amplification is (i.e., the extent to which the numerical amplification exceeds the baseline value of 2 in cells that carry three or more iCTRs (i.e., Ni>2). Therefore, cancer cells with 1 and 2 iCTRs do not contribute to this component. Since cells with larger numbers of iCTRs represent a more severe numerical centrosome amplification, a linear measurement was implemented to provide a measure of the number of iCTRs (above the baseline value of 2) in a given cell by computing the score (Ni-2) for each cell. Finally, an average of all these scores is determined.

For a comprehensive measure of the numerical amplification in a tumor sample, the severity component of the $CAS_i$ value for abnormal cells may be complemented by a measure of how frequently cells with Ni>2 occur in a given sample. A suitable means for implementing this measure involves calculating the percentage of cells in which Ni>2. Preferably this value is scaled to ensure that both $CAS_i$ and $CAS_m$ are given equal weight in the formula for calculating $CAS_{total}$. Consequently the "frequency" component of the $CAS_i$ score (i.e., $p_i/\beta_i$) provides the scaled frequency of numerical centrosome amplification in the sample.

The lowest value for the severity term in $CAS_i$ is 1 (assuming that all cells demonstrating numerical centrosome amplification have only 3 iCTRs); the maximum value for the severity term can potentially be a very high value, since the number of iCTRs per cell can be very high. The lowest value of the "frequency" component of $CAS_i$ is 0 (e.g., no abnormal cells contribute to the frequency). The highest value of the "frequency" component of CAS, for breast tissue is 10 (e.g., 100% of cells contain mCTRs and contribute to the frequency).

The values of the "severity" and "frequency" terms from individual tumor samples can be readily compared to each other. For instance, if the value of the severity term of $CAS_i$ for sample A is twice that in sample B, one can conclude that the severity of numerical amplification in Sample A is twice that in sample B. Similarly, if tissue A and B have the same severity, but the frequency of cells carrying >2 iCTRs in B is half the corresponding frequency in sample A, the $CAS_i$ of A will be double that of B. Moreover, the effects of both $CAS_i$ components (severity and frequency of numerical amplification) are multiplicative, meaning that if tissue A had both double severity and frequency compared to a sample B, the $CAS_i$ value of A will be 4 times larger than $CAS_i$ value of B. Although the severity and frequency terms of $CAS_i$ are multiplied to obtain the cumulative $CAS_i$ value, the severity and frequency terms will also be recorded separately since each individual value might also have value in risk prognostication in tumor samples.

The algorithm for the second embodiment further includes a structural centrosome amplification component (m-component) defined by the following formula (IIc):

$$CAS_m = \frac{\text{Average}(N_m \cdot (V_m - V_{m-critical}))}{\sigma_{V-m}} \cdot \frac{\text{percentage}(V_m > V_{m-critical})}{\text{scaling factor } m} = \frac{\sum_{j=1, V_j>0.76}^{N}(V_j - 0.76)N_{mj}}{\sigma_{V-m}} \cdot \frac{p_m}{\beta_m}$$

where:

$p_m$ is the percentage of cells that harbor mCTRs (structurally amplified centrosomes).

$V_m$ is the volume of a megacentrosome associated with a cell nucleus; where a megacentrosome is defined as a centrosome whose volume exceeds the $V_{m\ critical}$ for that tissue.

$V_{m\ critical}$ for a given tissue is the maximum volume of a normal centrosome in that tissue (for e.g., the $V_{m\ critical}$ for breast tissue is 0.76 cubic microns which is the upper limit of the normal centrosome volume range for normal breast tissue). In this case, values less than 0.76 cubic microns may be deemed normal; therefore, they will not contribute to the average. However, values of 0.76 cubic microns or larger would be deemed to be abnormal and would contribute to the average.

$\beta_m$ is a scaling factor used to ensure that both $CAS_i$ and $CAS_m$ are given equal weight in the formula for $CAS_{total}$. This value might change depending on the tissue type being evaluated and the data itself.

The value of variability in the normal tissue (i.e., non-cancerous and non-neoplastic tissue) the standard deviation was estimated from data to be $\sigma_{v\ m}=(0.76-0.23)/4=0.132$ (this value is only applicable for breast tissue immunostained for γ-tubulin).

$N_{mj}$ is the number of megacentrosomes per nucleus.

The index j is an implementary term that takes the values $\{1, 2, 3, \ldots, N\}$, that is, from 1, 2 all the way up to N.

The symbol m in $N_{mj}$ is used to indicate taking the average over cells with structural centrosome amplification.

The severity and frequency components for $CAS_m$ may be computed in a similar fashion as the $CAS_i$ scores. For each mCTR (centrosome whose volume exceeds the upper limit of the normal centrosome volume range for that tissue), a z-score is computed based on the formula below, reflecting the extent to which the volume of that mCTR exceeds the maximal normal value (i.e., the value for $V_m - V_{m\ critical}$ is computed) relative to the baseline (achieved by dividing by the standard deviation):

$$z = \frac{V_m - V_{m\ critical}}{\sigma_{V_m}}$$

Next, this value is multiplied by the number of megacentrosomes per nucleus. Finally, all these values are averaged in order to obtain the severity score.

The frequency component of $CAS_m$ has essentially the same overall mathematical formula as the corresponding term in the $CAS_i$ component, that is, frequency divided by the scaling factor, or $p_m/\beta_m$. Whereas the scaling factor for $CAS_i$ is 0.02 or 2%, the scaling factor for $CAS_m$ is 0.2 or 20%. The high and low values, and the multiplicative behavior of these two components are the same as for the severity and frequency terms of $CAS_i$ (see explanation above).

In the present form of the algorithm, the components $CAS_i$ and $CAS_m$, contribute equally to the total CAS score; in other words, they are given equal weight. Further evaluation of experimental data may lead to a refinement of these weighting factors for computing $CAS_{total}$ score, although it is recommended that all four components ($CAS_i$ vs $CAS_m$, and their severity vs frequency measures) be retained.

An exemplary calculation of $CAS_i$ and $CAS_m$ is provided below:

| Nuclei | No. of centrosomes with normal volume |
|---|---|
| N1 | 3 |
| N2 | 2 |
| N3 | 2 |
| N4 | 4 |
| N5 | 1 |

No. of nuclei with numerical amplification=2
Total no. of nuclei=5
$CAS_i$ severity: Fold Average numerical amplification among nuclei with numerical amplification
Average=(3−2)+(4−2)/2=1.5
$CAS_i$ frequency
2/5=0.4
$CAS_i$=1.5*0.4/0.02=0.6/0.02=30

| Nuclei | No. of mega CTRs | Mega CTR1 (volume) | Mega CTR 2 (volume) |
|---|---|---|---|
| N1 | 0 | | |
| N2 | 2 | 0.84 | 0.84 |
| N3 | 1 | 0.95 | |
| N4 | 0 | | |
| N5 | 1 | 1.20 | |

No. of nuclei with structural amplification=3
No. of total nuclei=5
$CAS_m$ severity=Fold average deviation from centrosomal volume found in normal tissue
(0.84−0.76)+(0.84−0.76)=0.16
0.95−0.76=0.19
0.80−0.76=0.44
Avg=0.16+0.19+0.44/3=0.263
0.263*3/std. dev=0.23/0.132=5.98
$CAS_m$ frequency
3/5=0.6
$CAS_m$=5.98*0.6/0.2=17.95

Table 1 shows exemplary raw data from a patient with breast cancer to illustrate the way in which the variables in the above-described algorithm can be calculated and recorded in order to calculate CA scores in accordance with the algorithm in the second embodiment.

TABLE 1

| Nuclei | iCTR | mCTR | Volume of mCTR | Ni-2 | Vm | Vm-critical | Vm − Vm-critical | Nm · (Vm − Vm-critical) |
|---|---|---|---|---|---|---|---|---|
| N1 | 1i | — | | 0 | 0 | 0 | 0 | 0 |
| N2 | 1i | — | | 0 | 0 | 0 | 0 | 0 |
| N3 | 1i | — | | 0 | 0 | 0 | 0 | 0 |
| N4 | — | 1m | 0.77 | 0 | 0.77 | 0.76 | 0.01 | 0.01 |
| N5 | 1i | — | | 0 | 0 | 0 | 0 | 0 |
| N6 | 1i | — | | 0 | 0 | 0 | 0 | 0 |
| N7 | 1i | — | | 0 | 0 | 0 | 0 | 0 |
| N8 | 1i | — | | 0 | 0 | 0 | 0 | 0 |
| N9 | 1i | — | | 0 | 0 | 0 | 0 | 0 |
| N10 | 1i | — | | 0 | 0 | 0 | 0 | 0 |
| N11 | 1i | — | | 0 | 0 | 0 | 0 | 0 |
| N12 | 1i | — | | 0 | 0 | 0 | 0 | 0 |
| N13 | — | 1m | 0.89 | 0 | 0.89 | 0.76 | 0.13 | 0.13 |
| N14 | — | 1m | 1.07 | 0 | 1.07 | 0.76 | 0.31 | 0.31 |
| N15 | — | 1m | 1.1 | 0 | 1.1 | 0.76 | 0.34 | 0.34 |
| N16 | — | 1m | 1.1 | 0 | 1.1 | 0.76 | 0.34 | 0.34 |
| N17 | — | 1m | 1.16 | 0 | 1.16 | 0.76 | 0.4 | 0.4 |
| N18 | — | 1m | 0.77 | 0 | 0.77 | 0.76 | 0.01 | 0.01 |
| N19 | 2i | — | | 0 | 0 | 0 | 0 | 0 |
| N20 | 4i | — | | 2 | 0 | 0 | 0 | 0 |

TABLE 1-continued

| Nuclei | iCTR | mCTR | Volume of mCTR | Ni-2 | Vm | Vm-critical | Vm − Vm-critical | Nm · (Vm − Vm-critical) |
|---|---|---|---|---|---|---|---|---|
| N21 | 2i | — | | 0 | 0 | 0 | 0 | 0 |
| N22 | 3i | — | | 1 | 0 | 0 | 0 | 0 |
| N23 | 3i | — | | 1 | 0 | 0 | 0 | 0 |
| N24 | 2i | — | | 0 | 0 | 0 | 0 | 0 |
| N25 | 2i | — | | 0 | 0 | 0 | 0 | 0 |
| N26 | — | 1m | 0.77 | 0 | 0.77 | 0.76 | 0.01 | 0.01 |
| N27 | — | 1m | 0.84 | 0 | 0.84 | 0.76 | 0.08 | 0.08 |
| N28 | — | 1m | 0.85 | 0 | 0.85 | 0.76 | 0.09 | 0.09 |
| N29 | — | 1m | 1.3 | 0 | 1.3 | 0.76 | 0.54 | 0.54 |
| N30 | — | 1m | 1.65 | 0 | 1.65 | 0.76 | 0.89 | 0.89 |
| N31 | — | 1m | 1.69 | 0 | 1.69 | 0.76 | 0.93 | 0.93 |
| N32 | — | 1m | 1.7 | 0 | 1.7 | 0.76 | 0.94 | 0.94 |
| N33 | — | 1m | 1.85 | 0 | 1.85 | 0.76 | 1.09 | 1.09 |
| N34 | — | 1m | 2.43 | 0 | 2.43 | 0.76 | 1.67 | 1.67 |
| N35 | 4i | — | | 2 | 0 | 0 | 0 | 0 |
| N36 | 2i | — | | 0 | 0 | 0 | 0 | 0 |
| N37 | 2i | — | | 0 | 0 | 0 | 0 | 0 |
| N38 | 1i | — | | 0 | 0 | 0 | 0 | 0 |
| N39 | 2i | — | | 0 | 0 | 0 | 0 | 0 |
| N40 | 6i | — | | 4 | 0 | 0 | 0 | 0 |
| N41 | 4i | — | | 2 | 0 | 0 | 0 | 0 |
| N42 | 2i | — | | 0 | 0 | 0 | 0 | 0 |
| N43 | 2i | — | | 0 | 0 | 0 | 0 | 0 |
| N44 | 2i | — | | 0 | 0 | 0 | 0 | 0 |
| N45 | 1i | — | | 0 | 0 | 0 | 0 | 0 |
| N46 | 1i | — | | 0 | 0 | 0 | 0 | 0 |
| N47 | 1i | — | | 0 | 0 | 0 | 0 | 0 |
| N48 | 1i | — | | 0 | 0 | 0 | 0 | 0 |
| N49 | — | 1m | 0.8 | 0 | 0.8 | 0.76 | 0.04 | 0.04 |
| N50 | — | 1m | 0.93 | 0 | 0.93 | 0.76 | 0.17 | 0.17 |
| N51 | — | 1m | 1.07 | 0 | 1.07 | 0.76 | 0.31 | 0.31 |
| N52 | — | 1m | 1.27 | 0 | 1.27 | 0.76 | 0.51 | 0.51 |
| N53 | — | 1m | 1.69 | 0 | 1.69 | 0.76 | 0.93 | 0.93 |
| N54 | — | 1m | 2.05 | 0 | 2.05 | 0.76 | 1.29 | 1.29 |
| N55 | 7i | — | | 5 | 0 | 0 | 0 | 0 |
| N56 | 2i | — | | 0 | 0 | 0 | 0 | 0 |
| N57 | 1i | — | | 0 | 0 | 0 | 0 | 0 |
| N58 | 2i | — | | 0 | 0 | 0 | 0 | 0 |
| N59 | 2i | — | | 0 | 0 | 0 | 0 | 0 |
| N60 | 2i | — | | 0 | 0 | 0 | 0 | 0 |
| N61 | 2i | — | | 0 | 0 | 0 | 0 | 0 |
| N62 | 2i | — | | 0 | 0 | 0 | 0 | 0 |
| N63 | 2i | — | | 0 | 0 | 0 | 0 | 0 |
| N64 | 2i | — | | 0 | 0 | 0 | 0 | 0 |
| N65 | 3i | — | | 1 | 0 | 0 | 0 | 0 |
| N66 | 2i | — | | 0 | 0 | 0 | 0 | 0 |
| N67 | — | 1m | 1.2 | 0 | 1.2 | 0.76 | 0.44 | 0.44 |
| N68 | — | 1m | 1.39 | 0 | 1.39 | 0.76 | 0.63 | 0.63 |
| N69 | — | 1m | 2.43 | 0 | 2.43 | 0.76 | 1.67 | 1.67 |
| N70 | 2i | — | | 0 | 0 | 0 | 0 | 0 |
| N71 | 2i | — | | 0 | 0 | 0 | 0 | 0 |
| N72 | 2i | — | | 0 | 0 | 0 | 0 | 0 |
| N73 | 2i | — | | 0 | 0 | 0 | 0 | 0 |
| N74 | 1i | — | | 0 | 0 | 0 | 0 | 0 |
| N75 | 1i | — | | 0 | 0 | 0 | 0 | 0 |
| N76 | — | 1m | 0.91 | 0 | 0.91 | 0.76 | 0.15 | 0.15 |
| N77 | — | 1m | 1.16 | 0 | 1.16 | 0.76 | 0.4 | 0.4 |
| N78 | — | 1m | 1.5 | 0 | 1.5 | 0.76 | 0.74 | 0.74 |
| N79 | — | 1m | 1.59 | 0 | 1.59 | 0.76 | 0.83 | 0.83 |
| N80 | 4i | — | | 2 | 0 | 0 | 0 | 0 |
| N81 | 2i | — | | 0 | 0 | 0 | 0 | 0 |
| N82 | 2i | — | | 0 | 0 | 0 | 0 | 0 |
| N83 | 2i | 1m | 1.51 | 0 | 1.51 | 0.76 | 0.75 | 0.75 |
| N84 | 1i | 1m | 2.13 | 0 | 2.13 | 0.76 | 1.37 | 1.37 |
| N85 | 5i | — | | 3 | 0 | 0 | 0 | 0 |
| N86 | 1i | — | | 0 | 0 | 0 | 0 | 0 |
| N87 | — | 1m | 1.17 | 0 | 1.17 | 0.76 | 0.41 | 0.41 |
| N88 | — | 1m | 1.54 | 0 | 1.54 | 0.76 | 0.78 | 0.78 |
| N89 | — | 1m | 1.66 | 0 | 1.66 | 0.76 | 0.9 | 0.9 |
| N90 | — | 1m | 1.69 | 0 | 1.69 | 0.76 | 0.93 | 0.93 |
| N91 | 2i | — | | 0 | 0 | 0 | 0 | 0 |
| N92 | — | 1m | 1.4 | 0 | 1.4 | 0.76 | 0.64 | 0.64 |
| N93 | 2i | — | | 0 | 0 | 0 | 0 | 0 |
| N94 | 1i | — | | 0 | 0 | 0 | 0 | 0 |
| N95 | 2i | — | | 0 | 0 | 0 | 0 | 0 |
| N96 | 2i | — | | 0 | 0 | 0 | 0 | 0 |

TABLE 1-continued

| Nuclei | iCTR | mCTR | Volume of mCTR | Ni-2 | Vm | Vm-critical | Vm − Vm-critical | Nm · (Vm − Vm-critical) |
|---|---|---|---|---|---|---|---|---|
| N97 | 2i | — | | 0 | 0 | 0 | 0 | 0 |
| N98 | 2i | — | | 0 | 0 | 0 | 0 | 0 |
| N99 | 1i | — | | 0 | 0 | 0 | 0 | 0 |
| N100 | 3i | — | | 1 | 0 | 0 | 0 | 0 |
| N101 | 2i | — | | 0 | 0 | 0 | 0 | 0 |
| N102 | 2i | — | | 0 | 0 | 0 | 0 | 0 |
| N103 | 1i | — | | 0 | 0 | 0 | 0 | 0 |
| N104 | — | 1m | 0.94 | 0 | 0.94 | 0.76 | 0.18 | 0.18 |
| N105 | — | 1m | 1.03 | 0 | 1.03 | 0.76 | 0.27 | 0.27 |
| N106 | — | 1m | 1.12 | 0 | 1.12 | 0.76 | 0.36 | 0.36 |
| N107 | — | 1m | 1.36 | 0 | 1.36 | 0.76 | 0.6 | 0.6 |
| N108 | — | 1m | 1.86 | 0 | 1.86 | 0.76 | 1.1 | 1.1 |
| N109 | — | 1m | 1.87 | 0 | 1.87 | 0.76 | 1.11 | 1.11 |
| N110 | 1i | — | | 0 | 0 | 0 | 0 | 0 |
| N111 | 3i | — | | 1 | 0 | 0 | 0 | 0 |
| N112 | 1i | | | 0 | 0 | 0 | 0 | 0 |
| N113 | — | 1m | 0.82 | 0 | 0.82 | 0.76 | 0.06 | 0.06 |
| N114 | — | 1m | 1.01 | 0 | 1.01 | 0.76 | 0.25 | 0.25 |
| N115 | — | 1m | 1.02 | 0 | 1.02 | 0.76 | 0.26 | 0.26 |
| N116 | — | 1m | 1.3 | 0 | 1.3 | 0.76 | 0.54 | 0.54 |
| N117 | — | 1m | 1.71 | 0 | 1.71 | 0.76 | 0.95 | 0.95 |
| N118 | — | 1m | 1.91 | 0 | 1.91 | 0.76 | 1.15 | 1.15 |
| N119 | — | 1m | 1.99 | 0 | 1.99 | 0.76 | 1.23 | 1.23 |
| N120 | 3i | — | | 1 | 0 | 0 | 0 | 0 |
| N121 | — | 1m | 1.65 | 0 | 1.65 | 0.76 | 0.89 | 0.89 |
| N122 | — | 1m | 1.67 | 0 | 1.67 | 0.76 | 0.91 | 0.91 |
| N123 | — | 1m | 2.32 | 0 | 2.32 | 0.76 | 1.56 | 1.56 |
| N124 | — | 1m | 2.97 | 0 | 2.97 | 0.76 | 2.21 | 2.21 |
| N125 | — | 1m | 3.45 | 0 | 3.45 | 0.76 | 2.69 | 2.69 |
| N126 | 2i | — | | 0 | 0 | 0 | 0 | 0 |
| N127 | 2i | — | | 0 | 0 | 0 | 0 | 0 |
| N128 | 2i | — | | 0 | 0 | 0 | 0 | 0 |
| N129 | 2i | — | | 0 | 0 | 0 | 0 | 0 |
| N130 | 1i | — | | 0 | 0 | 0 | 0 | 0 |
| N131 | | 1m | 0.91 | 0 | 0.91 | 0.76 | 0.15 | 0.15 |
| N132 | | 1m | 1.27 | 0 | 1.27 | 0.76 | 0.51 | 0.51 |
| N133 | | 1m | 1.47 | 0 | 1.47 | 0.76 | 0.71 | 0.71 |
| N134 | 1i | — | | 0 | 0 | 0 | 0 | 0 |
| N135 | 1i | — | | 0 | 0 | 0 | 0 | 0 |
| N136 | 1i | 1m | 1.68 | 0 | 1.68 | 0.76 | 0.92 | 0.92 |
| N137 | — | 1m | 0.81 | 0 | 0.81 | 0.76 | 0.05 | 0.05 |
| N138 | — | 1m | 0.93 | 0 | 0.93 | 0.76 | 0.17 | 0.17 |
| N139 | — | 1m | 1.03 | 0 | 1.03 | 0.76 | 0.27 | 0.27 |
| N140 | — | 1m | 1.32 | 0 | 1.32 | 0.76 | 0.56 | 0.56 |
| N141 | — | 1m | 1.48 | 0 | 1.48 | 0.76 | 0.72 | 0.72 |
| N142 | — | 1m | 2.8 | 0 | 2.8 | 0.76 | 2.04 | 2.04 |
| N143 | 3i | — | | 1 | 0 | 0 | 0 | 0 |
| N144 | 1i | — | | 0 | 0 | 0 | 0 | 0 |
| N145 | 2i | — | | 0 | 0 | 0 | 0 | 0 |
| N146 | 2i | — | | 0 | 0 | 0 | 0 | 0 |
| N147 | | 1m | 0.92 | 0 | 0.92 | 0.76 | 0.16 | 0.16 |
| N148 | | 1m | 0.97 | 0 | 0.97 | 0.76 | 0.21 | 0.21 |
| N149 | | 1m | 1.86 | 0 | 1.86 | 0.76 | 1.1 | 1.1 |
| N150 | 2i | — | | 0 | 0 | 0 | 0 | 0 |
| N151 | 2i | — | | 0 | 0 | 0 | 0 | 0 |
| N152 | 2i | — | | 0 | 0 | 0 | 0 | 0 |
| N153 | 1i | — | | 0 | 0 | 0 | 0 | 0 |
| N154 | 1i | — | | 0 | 0 | 0 | 0 | 0 |
| N155 | 1i | — | | 0 | 0 | 0 | 0 | 0 |
| N156 | 1i | — | | 0 | 0 | 0 | 0 | 0 |
| N157 | 2i | — | | 0 | 0 | 0 | 0 | 0 |
| N158 | 2i | — | | 0 | 0 | 0 | 0 | 0 |
| N159 | 2i | — | | 0 | 0 | 0 | 0 | 0 |
| N160 | 2i | — | | 0 | 0 | 0 | 0 | 0 |
| N161 | 2i | — | | 0 | 0 | 0 | 0 | 0 |
| N162 | 2i | — | | 0 | 0 | 0 | 0 | 0 |
| N163 | 2i | — | | 0 | 0 | 0 | 0 | 0 |
| N164 | 2i | — | | 0 | 0 | 0 | 0 | 0 |
| N165 | — | 1m | 0.99 | 0 | 0.99 | 0.76 | 0.23 | 0.23 |
| N166 | 3i | — | | 1 | 0 | 0 | 0 | 0 |
| N167 | 3i | — | | 1 | 0 | 0 | 0 | 0 |

The $CAS_i$, $CAS_m$ and $CAS_{total}$ scores based on the data in Table 1 may be determined using the steps described below based on formula IIa-IIc.

Figure 4:
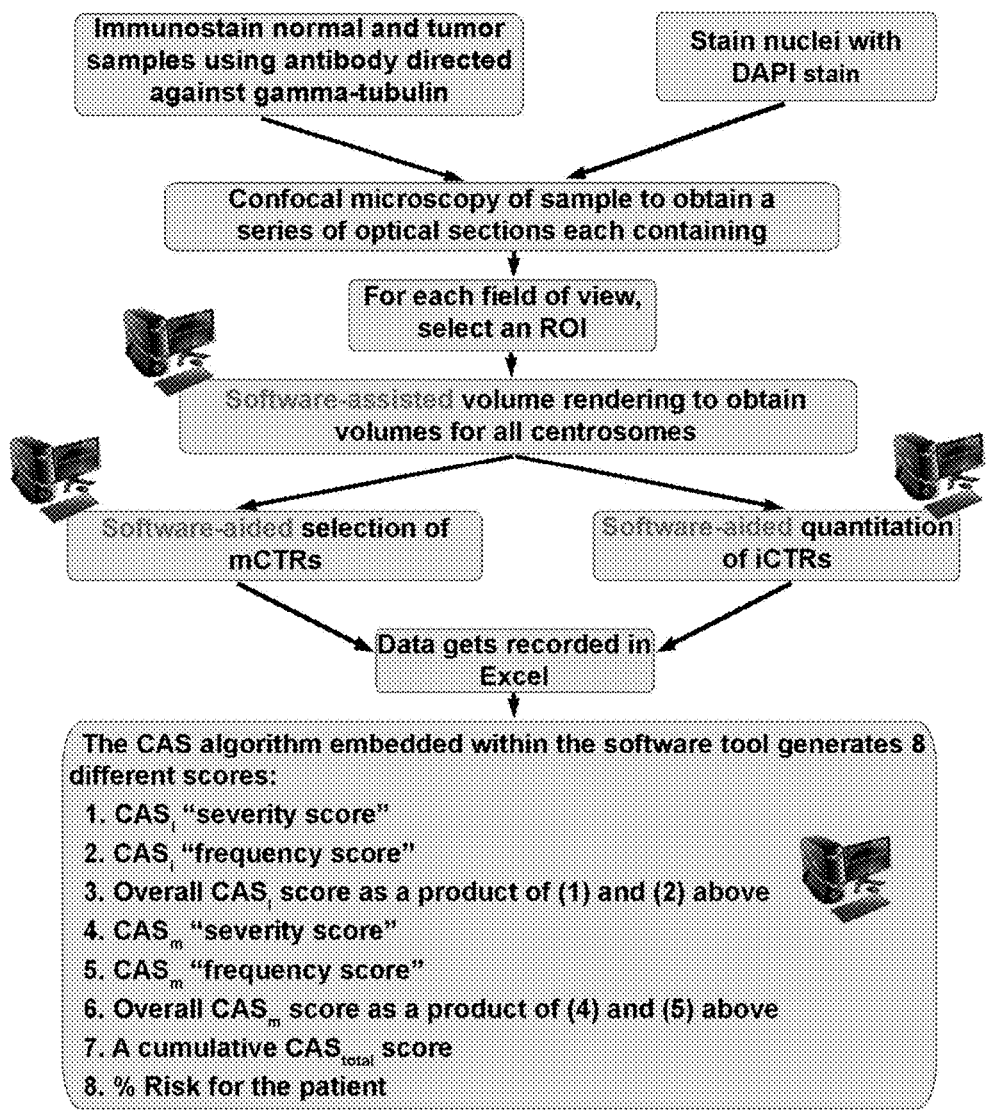
FIG. 4 shows another method for calculating $CAS_{total}$ scores.

For $CAS_i$:
1. Find $N_i$, i>2=series shown in excel
2. Calculate $\Sigma N_{ij}$-2=series shown in excel
3. Find n with i>2=16
4. Calculate Average $(N_i-2)=\Sigma N_{ij}/n=1.8125=CAS_i$-Severity
5. Calculate percentage, p=n/N=16/167=0.095808
6. Scaling factor, $\beta_i=0.02$
7. Calculate $p/\beta_i=4.79=CAS_i$-Frequency
   $CAS_i=1.8125*0.95808=8.6826$ For $CAS_m$
1. Find $N_m=68$
2. Calculate $\Sigma V_{mj}-V_{m\ critical}$=series shown in excel
3. Calculate $N_m*\Sigma_{mj}-V_{m\ critical}$=series shown in excel
4. Calculate Average $((N_m*(Vm-V_{m\ critical}))=0.6733823$
5. $\sigma\_(V-m)=\frac{1}{4}(0.76-0.23)=0.53*\frac{1}{4}=0.132$, for breast cancer
6. $0.6733823/0.132=5.10138=CAS_m$-Severity
7. Calculate percentage, $p=N_m/N=68/167=0.40718$
8. Scaling factor, $\beta hd\ m=0.2$
9. Calculate $p/\beta_m=2.0359$
10. $CAS_m=5.10138*2.0359=10.3858$ $CAS_{total}=CAS_i+CAS_m=8.6826+10.3858=19.0684$ FIG. 4 shows how CA scores may be calculated with the aid of software. Thus, in one embodiment, the present application provides a computer readable storage medium comprising software facilitating a number of functions associated with determination and analysis of CAS scores, including but not limited to: (a) supporting the entry of data, including numbers of iCTRs and mCTRs associated with each cell nucleus in an ROI; (b) generating three dimensional image data sufficient for volume rendering of the iCTRs and mCTRs in the ROI, (c) determining the average number of excess iCTRs (i.e., iCTRs in excess of 2) amongst cells that have >2 centrosomes; this gives a measure of the "severity" of numerical amplification present in the cells that bear numerically amplified centrosomes, (d) determining the percentage of cell nuclei that have excess iCTRs (i.e., iCTRs in excess of 2); this gives a measure of the "frequency" or "prevalence" of numerical centrosome amplification, (e) determining the average volume deviation (compared to the upper limit of the volume of normal centrosomes) of mCTRs among the cells that bear mCTRs; this gives a measure of the "severity" of structural amplification present in cells that bear structurally amplified centrosomes or mCTRs, (f) determining the percentage of cell nuclei that have mCTRs associated with them; this gives a measure of the "frequency" or "prevalence" of structural amplification of centrosomes, and (g) calculating one of more centrosome amplification scores based on the steps (b) to (f), where scores indicate the severity of centrosome amplification, the frequency of centrosome amplification, or both; and provide a measure of the level of risk associated with the neoplastic tissue.

Once CAS values are obtained for a large cohort of cancer specimens, one can either:
(1) use linear discriminant analyses or pair classification to separate $CAS_{total}$, CAS, and $CAS_m$ values into "high-risk" and "low-risk" categories based on detailed statistical analyses of the correlations between $CAS_{total}$, $CAS_i$ and $CAS_m$ values and clinical outcomes (including progression-free survival (PFS)/overall survival (OS)/metastasis-free survival (MFS)); or (2) stratify CAS values into discrete classes (for example, into low-, medium- and high-risk categories) and use it as a dependent variable in a multiple-group logistic regression analysis where clinical outcomes (PFS/OS/MFS) will be used as an independent variable. The stratified CAS class values are used as reference values for prognosis or diagnosis.

In addition, an ROC curve (Receiver Operating Characteristic, non-parametric) may be used to evaluate the cut-off $CAS_{total}$, $CAS_i$ and $CAS_m$ values based upon PFS/OS/MFS. Finally, the percent risk can be assigned to each CAS interval (i.e., each stratified CAS class) thereby establishing CAS as an independent measure of risk.

High CAS scores and/or high expression level(s) of CA-associated gene products indicate a poor prognosis and poor overall survival. In some embodiments, the prognosis is described as percentage or probability of survival in 6 month, 1 year, 2 years, 3 years, 4 years or 5 years. Once CAS scores are obtained for a large cohort of tumor specimens, this information can be correlated with survival information from the corresponding patients to determine cutoff values for CAS that define prognostic subgroups. In one approach, CAS values may be stratified into discrete prognostic risk classes and utilized as a dependent variable in a multiple-group logistic regression analysis where progression-free survival (PFS)/overall survival (OS) will be an independent variable. An ROC curve (Receiver Operating Characteristic, non-parametric) may be developed to evaluate the cut-off CAS values based upon PFS/OS. Alternatively, continuous, non-stratified CAS values may be employed in the ROC analysis, for determining cut-off values providing the largest degree of agreement with the clinical diagnosis.

A percentage risk may be assigned to each CAS interval, thereby establishing CAS as an independent indicator of metastasis risk irrespective of grade and receptor type. In one embodiment, when new patients arrive, high-risk and low-risk groups are assigned based on their respective CAS values. In other embodiments, any number of risk groups can be assigned to new patients based on their respective CAS values. In yet other embodiments, patients are given a "percentage risk" based on their respective CAS values.

In addition to calculating and analyzing CAS scores for risk assessment, the present methods may additionally include a step of determining whether the cells upregulate products (e.g., proteins or RNAs) associated with CA. Exemplary products for evaluation include major structural centrosomal proteins, both centriolar (centrin) and pericentriolar (pericentrin and γ-tubulin) and genes whose dysregulation is implicated in CA (polo-like kinase 4 and cyclin E). We could calculate a cumulative gene expression-based centrosome amplification index (CAI) by adding log transformed, normalized gene expression for CETN2 (centrin-2), TUBG1 (γ-tubulin), PCNT2 (pericentrin), PLK4 (polo-like kinase 4) and CCNE1 (cyclin E) genes. Any other combination of these markers may be evaluated to determine whether their expression levels are elevated relative to normal tissue controls and to quantitate the extent of this elevation in expression level.

Expression levels, including percent increases in expression level over controls, may be determined at the protein level (e.g., by immunohistochemistry, Western blot, antibody microarray, ELISA, etc.) or at the mRNA level (e.g., by RT-PCR, QT-PCR, oligonucleotide array, etc.). Preferred methodologies for determining protein expression levels (and ratios therefrom) include the use of immunohistochemistry, ELISAs, antibody microarrays and combinations thereof. Preferred methodologies for determining mRNA expression levels (and ratios therefrom) include quantitative reverse transcriptase PCR (QT-PCR), quantitative real-time RT-PCR, oligonucleotide microarrays and combinations thereof.

Elevated expression levels of proteins or mRNAs may represent increase(s) of 10%, 20%, 30%, 40%, 50%, 60%, 70%, 80%, 90% or 100% relative to normal tissue controls. In other embodiments, elevated expression levels may represent increase(s) of 2-fold, 3-fold, 5-fold, 10-fold, 20-fold, 50-fold or 100-fold increases relative to normal tissue controls. Similarly, increased Cdk1 activity and/or increased levels of phosphorylated histone-H3 may represent increase(s) of 10%, 20%, 30%, 40%, 50%, 60%, 70%, 80%, 90%, 100% (activity or phosphorylation) relative to normal tissue controls or may represent increase(s) of 2-fold, 3-fold, 5-fold, 10-fold, 20-fold, 50-fold or 100-fold increases relative to normal breast tissue controls.

The CAS may be combined with other factors to determine the risk profile of a patient. In some embodiments, the method further comprises the step of performing assay(s) from the patient's tumor cells to determine whether the tumor cells express an elevated level of nuclear HSET, Prc1, FoxM1, plk1, KPNA2 and/or Aurora A, wherein an elevated level of nuclear HSET, Prc1, FoxM1, plk1, KPNA2 and/or Aurora A indicates a high risk for the patient. In some embodiments, the tumor cells express elevated levels of nuclear HSET and nuclear Prc1, FoxM1, plk1, KPNA2 and/or Aurora A indicates a poorer prognosis. Prc1 is a non-motor-microtubule-associated protein that appears to be co-regulated and co-localized with HSET.

The CASs can be employed in risk models in combination with nuclear HSET weighted index (as described in U.S. patent application Ser. No. 14/559,593, which is incorporated herein in its entirety be reference) and other traditionally-used clinicopathologic parameters, predictive biomarkers and prognosticators (for example: age, gender, ancestry, histological grade, stage, hormone status, Ki67 score, BRCA1/2 status, tumor infiltrating lymphocytes, etc. for breast cancer; and serum biomarkers for other cancer types) from a given patient to (1) provide measures of cumulative risk (risk of progression to malignancy, risk of metastasis, risk of recurrence, risk of poor outcomes) or (2) predict responses to certain therapies. In these risk models, CASs and the other parameters may be given appropriate weights and combined mathematically in ways that are demonstrated to yield best patient stratification and/or best concordance with clinical outcomes. CASs can also be employed as a surrogate or measure of chromosomal instability.

III. Administration of Therapeutic Agents

Antimitotic drugs targeting mitosis, including Aurora kinase and Plk4 inhibitors, have largely failed in recent clinical trials as reflected in a 1.6% response rate compared to placebo. This failure of antimitotics reflects a longstanding problem of tumors having been thought of as being comprised of briskly proliferating cells. In reality, tumor cells divide infrequently, such that the median doubling time for breast tumors is almost 188 days. Accordingly, there is a need for identifying and exploiting other differences between normal and malignant cells when considering improved therapeutic regimens.

One such stark difference lies in the numbers of centrosomes in cancer cells. In particular, about 80% of breast cancers exhibit centrosome amplification, a feature that is a potential indicator of cancer aggressiveness. For example, unlike normal mammary epithelial cells that possess only one or two centrosome in interphase, breast cancer cells harbor extra centrosomes which typically cluster to generate a "super-centrosome". "Huddling" of supernumerary centrosomes is a cancer cell-specific phenomenon and can be exploited for diagnostic and therapeutic gains.

Based on a sample's CAS value, it can be determined if the patient belongs to a high risk group. If so, the patient would be a suitable candidate for centrosome-targeting therapies or microtubule-targeting therapies, inasmuch as supernumerary centrosomes are known to nucleate a higher number of microtubules. Several small-molecules, such as griseofulvin (tubulin-binding antifungal drug), brominated noscapines (microtubule-modulating agents), and PJ34 (phenanthrene-derived PARP inhibitor) extensively disperse "supercentrosomal clusters" to generate cells with highly aberrant multipolar spindles that signify a "point of no return" and consign cells to death. Centrosome-disrupting agents can induce cell death during mitosis and are attractive drug candidates owing to their cancer-cell specificity.

More particularly, high CAS scores and/or high expression level(s) of CA-associated gene products indicate a poor prognosis and poor overall survival, particularly without appropriate and aggressive treatment. Accordingly, where tumor cells from a cancer patient are found to have high CAS scores and/or high expression level(s) of CA-associated gene products, the patient may be further treated with one or more therapeutic agents, particularly tubulin targeting drugs. In some embodiments, a patient who has a benign tumor or atypical hyperplasia may be classified as "high-risk" for developing malignancy based on CAS analysis and such patient may also need to go on a chemopreventive regimen.

For the purpose of prognosis, once a CAS is obtained for a large cohort of tumor specimens, the probability of poor prognosis is estimated by determining cutoff values for CAS that define prognostic subgroups using the following approaches: (1) stratifying CAS values into discrete prognostic risk classes and using it as a dependent variable in a multiple-group logistic regression analysis where progression-free survival (PFS)/overall survival (OS) will be an independent variable; (2) using the ROC curve (Receiver Operating Characteristic, non-parametric) to evaluate cut-off CAS values based upon PFS/OS. Alternatively, the continuous, non-stratified, CAS values can be used in the ROC analysis to determine at which cut-off values the largest degree of agreement with the clinical diagnosis may be obtained; and (3) assigning a percentage risk to each CAS interval thereby establishing CAS as an independent indicator of metastasis risk irrespective of grade and receptor type. Thus, when new patients arrive, they can be assigned to different groups (such as high-risk, medium-risk and/or low-risk groups) based on their respective CAS values. For the purpose of treatment, patients belonging to high risk group based on the patients' CAS values could be suitable candidates for centrosome-targeting therapies or microtubule-targeting therapies (since it is well known that supernumerary centrosomes nucleate a higher number of microtubules).

In some embodiments, CAS are used to identify which patients should be chosen for clinical trials involving experimental centrosome-targeting drugs or microtubule-targeting drugs in order to increase the likelihood of success of such trials.

In other embodiments, CAS scores are used to monitor a patient's response to a cancer therapy (e.g., chemotherapy). A patients' tumor can be assessed after treatment with an anticancer therapeutic agent and the centrosomes of the cells monitored for reversal of one or more defects. Cancer cells can be analyzed using the methods of the subject invention to determine if treatment with a particular therapeutic agent (e.g., MLN8054, an Aurora kinase inhibitor, see Huck et al. (2010); Manfredi et al. (2007)) reverses or ameliorates mitotic spindle and segregation defects and chromosomal instability that are typically observed in centrosome amplification of cancer and tumor cells. If the particular treatment appears to have activity in reversing or ameliorating centrosomal defects of the cancer or tumor cells, or other defects that are caused by amplified centrosomes, then the clinician can predict that the tested treatment would be useful in treating the patient and the patient can be administered the particular treatment in a manner deemed most clinically appropriate. Similarly, if a particular treatment does not appear to have activity in reversing or ameliorating centrosomal defects of the cancer or tumor cells, then the clinician might predict that the tested treatment would not be useful in treating the patient and may decide not to administer the particular treatment to the patient and may determine that an alternate or modified treatment would be more likely to have a clinically beneficial effect for the patient.

For the purpose of predicting risk of progressing to malignant disease, a large cohort of pre-cancerous tissue samples (e.g., atypical ductal hyperplasia in case of breast cancer) with long follow-up data available (10-25 years) may be employed to carry out a retrospective study wherein (a) CAS values for those samples will be determined, and (b) CAS cut-offs will be determined after statistical analyses of CAS data and clinical outcome data; steps (a) and (b) would allow determination of cutoffs values of CASs to define various risk groups or a percentage risk of progressing to malignant disease.

In one embodiment, the patient is administered one or more centrosome declustering agents, including but not limited to griseofulvin; noscapine, noscapine derivatives, such as brominated noscapine (e.g., 9-bromonoscapine), reduced bromonoscapine (RBN), N-(3-brormobenzyl) noscapine, aminonoscapine and water-soluble derivatives thereof; CW069; the phenanthridene-derived poly(ADP-ribose) polymerase inhibitor, PJ-34; N2-(3-pyridylmethyl)-5-nitro-2-furamide, N2-(2-thienylmethyl)-5-nitro-2-furamide, N2-benzyl-5-nitro-2-furamide, an anthracine compound as described in U.S. Patent Application Publication 2008/0051463; a 5-nitrofuran-2-carboxamide derivative as described in U.S. Provisional Application 61/619,780; and derivatives and analogs therefrom.

In another embodiment, the patient is administered an inhibitor of HSET, a key mediator of centrosome clustering. The inhibitor of HSET can be a small molecule drug or a nucleic acid-based therapeutic, such as an siRNA, an shRNA-encoded expression vector or an antisense oligonucleotide, whereby the inhibitor inhibits the activity and/or expression of HSET in the targeted cell. Alternatively, or in addition, the patient may be administered an inhibitor of a protein that is upregulated with HSET or inhibitors of other proteins implicated in centrosome clustering. HSET co-regulated product targets include, but are not limited to Npap60L, CAS, Prc1, Ki67, survivin, phospho-survivin, Hif1α, aurora kinase B, p-Bcl2, Mad1, Plk1, FoxM1, KPNA2, Aurora A and combinations thereof. In other embodiments, the patient is administered one or more agents that block the nuclear accumulation of HSET during interphase.

siRNAs are double-stranded RNAs that can be engineered to induce sequence-specific post-transcriptional gene silencing of mRNAs. Synthetically produced siRNAs structurally mimic the types of siRNAs normally processed in cells by the enzyme Dicer. siRNAs may be administered directly in their double-stranded form or they may be expressed from an expression vector is engineered to transcribe a short double-stranded hairpin-like RNA (shRNA) that is processed into a targeted siRNA inside the cell. Suitable expression vectors include viral vectors, plasmid vectors and the like and may be delivered to cells using two primary delivery schemes: viral-based delivery systems using viral vectors and non-viral based delivery systems using, for example, plasmid vectors. Exemplary viral vectors may include or be derived from an adenovirus, adeno-associated virus, herpesvirus, retrovirus, vaccinia virus, poliovirus, poxvirus, HIV virus, lentivirus, retrovirus, Sindbis and other RNA viruses and the like.

As used herein, the term "oligonucleotide" refers to a single stranded nucleic acid containing between about 15 to about 100 nucleotides. An antisense oligonucleotide comprises comprise a DNA backbone, RNA backbone, or chemical derivative thereof, which is designed to bind via complementary binding to an mRNA sense strand of a target gene (such as HSET) so as to promote RNase H activity, thereby leading to degradation of the mRNA. Preferably, the antisense oligonucleotide is chemically or structurally modified to promote nuclease stability and/or increased binding. The single stranded antisense oligonucleotide may be synthetically produced or it may be expressed from a suitable expression vector. In addition, the antisense oligonucleotide may be modified with nonconventional chemical or backbone additions or substitutions, including but not limited to peptide nucleic acids (PNAs), locked nucleic acids (LNAs), morpholino backboned nucleic acids, methylphosphonates, duplex stabilizing stilbene or pyrenyl caps, phosphorothioates, phosphoroamidates, phosphotriesters, and the like.

In certain embodiments, the small molecule drug targets the motor domain of HSET and/or specifically binds to the HSET/microtubule binary complex so as to inhibit HSET's microtubule-stimulated and/or microtubule-independent ATPase activities. In a specific embodiment, the small molecule drug is AZ82 or CW069 or a therapeutically effective derivative, salt, enantiomer, or analog thereof.

AZ82 binds specifically to the KIFC1/microtubule (MT) binary complex and inhibits the MT-stimulated KIFC1 enzymatic activity in an ATP-competitive and MT-noncompetitive manner with a Ki of 0.043 µM. Treatment with AZ82 causes centrosome declustering in BT-549 breast cancer cells with amplified centrosomes.

Alternatively, or in addition, the patient may be administered a poly(ADP-ribose) polymerase (PARP) inhibitor, an inhibitor of the Ras/MAPK pathway, an inhibitor of the PI3K/AKT/mTOR pathway, an inhibitor of FoxM1, Hif1α, surviving, Aurora, Plk1 or a combination thereof. Exemplary PARP inhibitors include, but are not limited to olaparib, iniparib, velaparib, BMN-673, BSI-201, AG014699, ABT-888, GPI21016, MK4827, INO-1001, CEP-9722, PJ-34, Tiq-A, Phen, PF-01367338 and combinations thereof. Exemplary Ras/MAPK pathway agents include, but are not limited to MAP/ERK kinase (MEK) inhibitors, such as trametinib, selumetinib, cobimetinib, CI-1040, PD0325901, AS703026, RO4987655, RO5068760, AZD6244, GSK1120212, TAK-733, U0126, MEK162, GDC-0973 and combinations thereof. Exemplary PI3K/AKT/mTOR pathway inhibitors include, but are not limited to everolimus, temsirolimus, GSK2126458, BEZ235, PIK90, PI103 and combinations thereof.

Other Prescribed Therapies

Alternatively, or in addition to administering centrosome declustering drugs, HSET-targeted drugs, or others described above, a patient exhibiting high CA scores may be additionally treated with adjuvant chemotherapeutic agents to further reduce the risk of adverse events, such as metastasis, disease relapse, and poor survival. Adjuvant chemotherapies may include administration of cyclophosphamide, taxanes, such as docetaxel and paclitaxel; anthracyclines, such as epirubicin and doxorubicin; gemcitabine, cisplatin, fluorouracil, ixabepilone, capecitabine, epidermal growth factor receptor-targeting agents, and combinations thereof.

The appropriate dosage ("therapeutically effective amount") of the therapeutic agent(s) will depend, for example, on the severity and course of the breast cancer, the mode of administration, the bioavailability of the therapeutic agent(s), previous therap(ies), the age and weight of the patient, the patient's clinical history and response to the therapeutic agent(s), the type of the therapeutic agent used, discretion of the attending physician, etc. The therapeutic agent(s) are suitably administered to the patent at one time or over a series of treatments and may be administered to the patient at any time from diagnosis onwards. The therapeutic agent(s) may be administered as the sole treatment or in combination with other drugs or therapies useful in treating the breast cancer. When used with other drugs, the therapeutic agent(s) may be used at a lower dose to reduce toxicities and/or side effects.

The therapeutic agent(s) may be administered to the patient with known methods, such as intravenous administration as a bolus or by continuous infusion over a period of time, by intramuscular, intraperitoneal, intracerebrospinal, subcutaneous, intra-articular, intrasynovial, intrathecal, oral, topical and/or inhalation routes. As a general proposition, the therapeutically effective amount(s) of the above described therapeutic agent(s) will be in the range of about 1 ng/kg body weight/day to about 100 mg/kg body weight/day whether by one or more administrations. In a particular embodiments, each therapeutic agent is administered in the range of from about 1 ng/kg body weight/day to about 10 mg/kg body weight/day, about 1 ng/kg body weight/day to about 1 mg/kg body weight/day, about 1 ng/kg body weight/day to about 100 µg/kg body weight/day, about 1 ng/kg body weight/day to about 10 µg/kg body weight/day, about 1 ng/kg body weight/day to about 1 µg/kg body weight/day, about 1 ng/kg body weight/day to about 100 ng/kg body weight/day, about 1 ng/kg body weight/day to about 10 ng/kg body weight/day, about 10 ng/kg body weight/day to about 100 mg/kg body weight/day, about 10 ng/kg body weight/day to about 10 mg/kg body weight/day, about 10 ng/kg body weight/day to about 1 mg/kg body weight/day, about 10 ng/kg body weight/day to about 100 µg/kg body weight/day, about 10 ng/kg body weight/day to about 10 µg/kg body weight/day, about 10 ng/kg body weight/day to about 1 µg/kg body weight/day, 10 ng/kg body weight/day to about 100 ng/kg body weight/day, about 100 ng/kg body weight/day to about 100 mg/kg body weight/day, about 100 ng/kg body weight/day to about 10 mg/kg body weight/day, about 100 ng/kg body weight/day to about 1 mg/kg body weight/day, about 100 ng/kg body weight/day to about 100 µg/kg body weight/day, about 100 ng/kg body weight/day to about 10 µg/kg body weight/day, about 100 ng/kg body weight/day to about 1 µg/kg body weight/day, about 1 µg/kg body weight/day to about 100 mg/kg body weight/day, about 1 µg/kg body weight/day to about 10 mg/kg body weight/day, about 1µg/kg body weight/day to about 1 mg/kg body weight/day, about 1µg/kg body weight/day to about 100 µg/kg body weight/day, about 1µg/kg body weight/day to about 10 µg/kg body weight/day, about 10 µg/kg body weight/day to about 100 mg/kg body weight/day, about 10 µg/kg body weight/day to about 10 mg/kg body weight/day, about 10 µg/kg body weight/day to about 1 mg/kg body weight/day, about 10 µg/kg body weight/day to about 100 µg/kg body weight/day, about 100 µg/kg body weight/day to about 100 mg/kg body weight/day, about 100 µg/kg body weight/day to about 10 mg/kg body weight/day, about 100 µg/kg body weight/day to about 1 mg/kg body weight/day, about 1 mg/kg body weight/day to about 100 mg/kg body weight/day, about 1 mg/kg body weight/day to about 10 mg/kg body weight/day, about 10 mg/kg body weight/day to about 100 mg/kg body weight/day.

In certain embodiments, the therapeutic agent(s) are administered at a dose of 500 µg to 20 g every three days, or 10 µg to 400 mg/kg body weight every three days. In other embodiments, each therapeutic agent is administered in the range of about 10 ng to about 100 ng per individual administration, about 10 ng to about 1µg per individual administration, about 10 ng to about 10 µg per individual administration, about 10 ng to about 100 µg per individual administration, about 10 ng to about 1 mg per individual administration, about 10 ng to about 10 mg per individual administration, about 10 ng to about 100 mg per individual administration, about 10 ng to about 1000 mg per injection, about 10 ng to about 10,000 mg per individual administration, about 100 ng to about 1µg per individual administration, about 100 ng to about 10 µg per individual administration, about 100 ng to about 100 µg per individual administration, about 100 ng to about 1 mg per individual administration, about 100 ng to about 10 mg per individual administration, about 100 ng to about 100 mg per individual administration, about 100 ng to about 1000 mg per injection, about 100 ng to about 10,000 mg per individual administration, about 1 µg to about 10 µg per individual administration, about 1 µg to about 100 µg per individual administration, about 1 µg to about 1 mg per individual administration, about 1 µg to about 10 mg per individual administration, about 1 µg to about 100 mg per individual administration, about 1 µg to about 1000 mg per injection, about 1 µg to about 10,000 mg per individual administration, about 10 µg to about 100 µg per individual administration, about 10 µg to about 1 mg per individual administration, about 10 µg to about 10 mg per individual administration, about 10 µg to about 100 mg per individual administration, about 10 µg to about 1000 mg per injection, about 10 µg to about 10,000 mg per individual administration, about 100 µg to about 1 mg per individual administration, about 100 µg to about 10 mg per individual administration, about 100 µg to about 100 mg per individual administration, about 100 µg to about 1000 mg per injection, about 100 µg to about 10,000 mg per individual administration, about 1 mg to about 10 mg per individual administration, about 1 mg to about 100 mg per individual administration, about 1 mg to about 1000 mg per injection, about 1 mg to about 10,000 mg per individual administration, about 10 mg to about 100 mg per individual administration, about 10 mg to about 1000 mg per injection, about 10 mg to about 10,000 mg per individual administration, about 100 mg to about 1000 mg per injection, about 100 mg to about 10,000 mg per individual administration and about 1000 mg to about 10,000 mg per individual administration. The therapeutic agent(s) may be administered daily, or every 2, 3, 4, 5, 6 and 7 days, or every 1, 2, 3 or 4 weeks.

In other particular embodiments, the therapeutic agent(s) are administered at a dose of about 0.0006 mg/day, 0.001 mg/day, 0.003 mg/day, 0.006 mg/day, 0.01 mg/day, 0.03 mg/day, 0.06 mg/day, 0.1 mg/day, 0.3 mg/day, 0.6 mg/day, 1 mg/day, 3 mg/day, 6 mg/day, 10 mg/day, 30 mg/day, 60 mg/day, 100 mg/day, 300 mg/day, 600 mg/day, 1000 mg/day, 2000 mg/day, 5000 mg/day or 10,000 mg/day. As expected, the dosage(s) will be dependent on the condition, size, age and condition of the patient.

Another aspect of the present application relates to a method for treating a cancer patient with high CAS score(s) and/or high expression level(s) of CA-associated gene products by administering an effective amount of an agent that increases the Npap60L-to-Npap60S ratio in or around the cancer tissue(s) of the patient.

Another aspect of the present application relates to a method for treating a cancer patient with high CAS score(s) and/or high expression level(s) of CA-associated gene products by administering an effective amount of an agent that inhibits the expression or activity of Prc1 in or around the cancer tissue(s) of the patient.

Another aspect of the present application relates to a method for treating a cancer patient with high CAS score(s) and/or high expression level(s) of CA-associated gene products by administering an effective amount of an agent that inhibits the expression or activity of FoxM1 and/or Plk1 in or around the cancer tissue(s) of the patient Another aspect of the present application relates to a method for treating a cancer patient with high CAS score(s) and/or high expression level(s) of CA-associated gene products by administering an effective amount of an agent that inhibits the expression or activity of Aurora A and/or KPNA2 in or around the cancer tissue(s) of the patient.

Another aspect of the present application relates to a kit for determining CAS scores in a patient. In one embodiment, the kit includes one or more reagents for immunohistochemistry, such as reagents for staining nuclei and centrosomes, as well as software for calculating CAS scores. In some embodiments, the kit may further include primary binding agents specifically binding to one or more gene product(s) upregulated in connection with CA (as described above), and secondary detection agents binding to the primary binding agents. In certain preferred embodiments, the primary and/or secondary binding agents are antibodies.

The present invention is further illustrated by the following examples which should not be construed as limiting. The contents of all references, patents and published patent applications cited throughout this application, as well as the Figures and Tables are incorporated herein by reference.

EXAMPLES

Example 1

Quantitative Comparison of Centrosomal Aberrations in Grade-Matched Breast, Bladder and Pancreatic Carcinomas Tissue microarrays (TMAs) constructed from formalin-fixed, paraffin-embedded grade-matched biopsies/resections of breast (n=35), bladder (n=33) and pancreatic (n=20) carcinomas were immunostained using an antibody against the centrosomal component gamma-tubulin for centrosomes, and co-stained with DAPI nuclear stain. Immunofluorescence confocal imaging was then used to stack optical sections of tumor tissue and capture all centrosomes and nuclei within 15 ROIs per sample. Centrosomes were categorized as (i) individually-distinguishable centrosomes (iCTRS) or (ii) as megacentrosomes (mCTRs) constituting several tightly clustered centrosomes whose precise number could not be determined. For each ROI, the number of nuclei as well as the numbers and volumes of all iCTRs and mCTRs were determined. A cumulative CAS was obtained for each ROI using formula I.

The results showed that nonneoplastic tissue did not exhibit CA and had CAS values well within the predicted range of 2-3. In contrast, the average CAS values for tumors were significantly higher, with breast tumors exhibiting higher CAS values (CAS range 4-47) than bladder (CAS 5-18) and pancreatic cancers (CAS 5-16). All tumors (n=88) exhibited significantly higher CAS values than their adjacent nonneoplastic counterparts (p<0.01).

These findings indicate that the extent and severity of numeric as well as structural centrosomal aberrations can be quantitatively determined in tumor samples using the present methods. Accordingly, this method may be used directly for evaluating archival clinical samples whose clinical outcomes are known.

Example 2

Quantifying Centrosomal Amplification in Multiple Tumor Samples

A quantitative comparison of centrosomal aberrations in grade-matched breast, bladder and pancreatic carcinomas was performed. Tissue Microarrays (TMAs) constructed from formalin-fixed, paraffin-embedded grade-matched biopsies/resections of breast (n=35), bladder (n=33) and pancreatic (n=20) carcinomas were immunostained for centrosomes, and co-stained with DAPI nuclear stain. Immunofluorescence confocal imaging was then used to stack optical sections of tumor tissue and capture all centrosomes and nuclei within 15 regions of interest (ROIs) per sample. Centrosomes were categorized as (i) individually-distinguishable centrosomes (iCTRS) or (ii) as megacentrosomes (mCTRs) comprised of several tightly clustered centrosomes whose precise number could not be determined. For each ROI, the number of nuclei as well as the numbers and volumes of all iCTRs and mCTRs were determined. A cumulative Centrosome Amplification Score (CAS) was obtained for each ROI using the following the Formula I.

This analysis showed that nonneoplastic tissue did not exhibit CA, and had CAS values well within the predicted range of 2-3. In contrast, the average CAS values for tumors were significantly higher, with breast tumors exhibiting higher CAS values (CAS range 4-47) than bladder (CAS 5-18) and pancreatic cancers (CAS 5-16). All tumors (n=88) exhibited significantly higher CAS values than their adjacent nonneoplastic counterpart (p<0.01). Quantification of CAS in tumor samples establishes CA as a "quantifiable cell biological property" enabling a determination of the extent and severity of numeric as well as structural centrosomal aberrations.

Example 3

CAS Scores Provide a Risk-Predictive Biomarker for Breast Cancer

Breast tumors harbor extensive intratumoral heterogeneity (ITH), both within primary and metastatic lesions. The generation of this genetic diversity relies on chromosomal instability (CIN), a dynamic and complex multilayered phenotype. CIN comprises of an increased propensity to missegregate chromosomes during mitosis and ostensibly can be regarded as a survival state adapted to aneuploidy, frequent aberrant mitosis and a sustained reshuffling of the genome. Centrosome amplification (CA) is known to compromise mitotic fidelity resulting in CIN. Essentially, CA assists cancer cells in concocting an array of diverse clones that drives tumor evolution by providing basic infrastructure for ITH. To investigate the impact of CA in driving ITH associated with tumor progression, CAS scores were determined based on Formula II to evaluate the extent to which CA affects the progression of a well-differentiated to a poorly-differentiated tumor.

Tissue specimens from 200 breast tumors were immunostained for centrosomes and nuclei. Employing confocal imaging, a stack of optical sections was acquired within 10 regions of interest (ROIs) per sample. Centrosomes were categorized as (i) individually-distinguishable centrosomes (iCTRs) or (ii) megacentrosomes (mCTRs) comprised of several tightly clustered centrosomes. For each ROI, the number of nuclei as well as the numbers and volumes of iCTRs and mCTRs were determined and a cumulative Centrosome Amplification Score (CAS) was obtained as $CAS_{total}=CAS_m$.

Low-grade (n=75) tumors were found to exhibit significantly higher $CAS_i$ (3.9 vs 2.3), $CAS_m$ (9.5 vs 5.4) and $CAS_{total}$ (12.8 vs 8.05) values than high-grade (Grade II and III, n=125) tumors, disproving the previously held notion that CA increases during disease progression. This postulation is supported by the observation that low-grade tumors exhibiting lymph node infiltration and metastasis (n=30) had higher $CAS_m$ (7.1 vs 9.8) and $CAS_{total}$ (9.5 vs 11.5) (reverse these numbers) values as compared to non-invasive low-grade tumors (n=50) These results establish CA as a "quantifiable cell-biological property" that can potentially predict the risk of a low-grade tumor being or becoming an aggressive and invasive one.

Example 4

Interphase and Mitotic Cells in High-Grade Clinical Cancers Display Robust Centrosome Amplification and Clustering Compared to Cells Cultured In Vitro A comparison of the frequency of CA and the spatial distribution of supernumerary centrosomes in interphase and mitotic cells within several clinical tumor types was compared with similar tumor cells cultured in vitro.

Centrosomes and microtubules were visualized by immunostaining for γ-tubulin (green) and α-tubulin (red), respectively. DNA was stained with DAPI (blue). Colonic (n=12), cervical (n=13), bladder (n=33), breast (n=50) and pancreatic (n=45) carcinoma tissues were evaluated to determine the frequency of CA and organization of amplified centrosomes in both interphase and mitosis. Percentages were calculated from 10 random fields in each sample. By comparison, various cancer cell lines including HT-29 (colon), HeLa (cervix), T24 (bladder), MDA-MB-231 (breast) and MiaPaCa (pancreas) were similarly evaluated for CA status in random cell populations and counted 1000 tumor cells in each case.

Centrosome amplification was observed in 60-85% cells in all the above tumor tissues (p<0.001). The majority of amplified centrosomes in tumors were clustered both in interphase (~90%) and mitotic (80-90%) cells. By comparison, in cultured cell lines only 5-20% of cells exhibited amplified centrosomes (p<0.001), indicating that cell lines had significantly lower frequencies of CA than those observed in patient tumors. Multiple centrosomes occurred either as a cluster in interphase cells (~80%) or as two clusters at the two poles of pseudobipolar mitotic spindles (60-80%).

Thus, in contrast to tumor cells lines, an overwhelming majority of patient tumor cells in high-grade cancers are in interphase and bear aberrant, amplified centrosomes commonly segregated into daughter cells as two clusters via pseudobipolar mitoses. These supernumerary centrosomes remain "huddled" together in a clustered configuration through interphase.

Example 5

Increased CAS Scores Correlate With Lower Survival Rates in African-Americans (AA) With Breast Cancer Compared to Grade-Matched Caucasians With Breast Cancer Paraffin-embedded receptor-matched Grade 1 breast cancer tissue samples from AA (n=65) and Caucasian (n=55) women and normal breast tissue samples (n=15) in a tissue microarray (TMA) were evaluated to quantify the extent and severity of CA in each sample (numeral and structural). Each sample was immunofluorescently stained using an antibody against γ-tubulin (centrosomal marker, green) and stained nuclei using DAPI (blue). Numbers of iCTRs and mCTRs were determined and the number of nuclei by examining 10 high power fields (HPFs, 63× magnification, NA=1.4). Three dimensional volumes of iCTRs and mCTRs were determined using Axiovision software and CAS values were calculated for the samples using Formula I.

Figure 5:
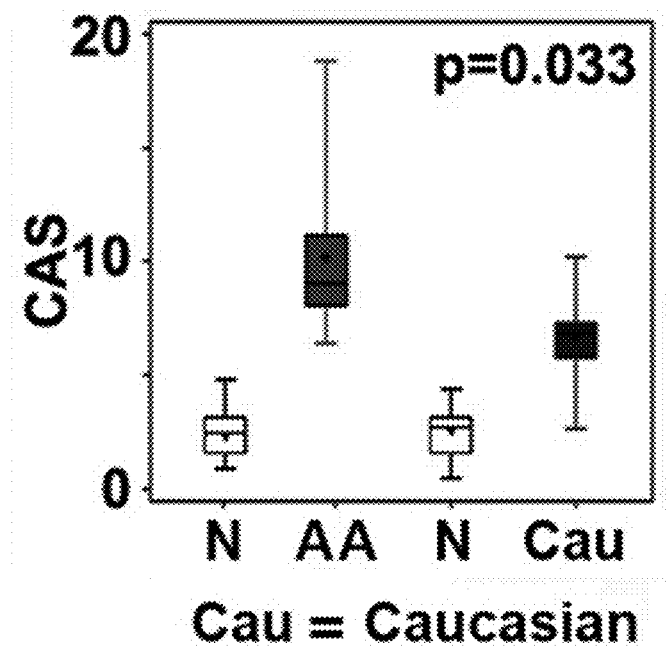
FIGS. 5-7 depict the centrosomal disparity between African American (AA) and Caucasian women with breast cancer.
Figure 6:
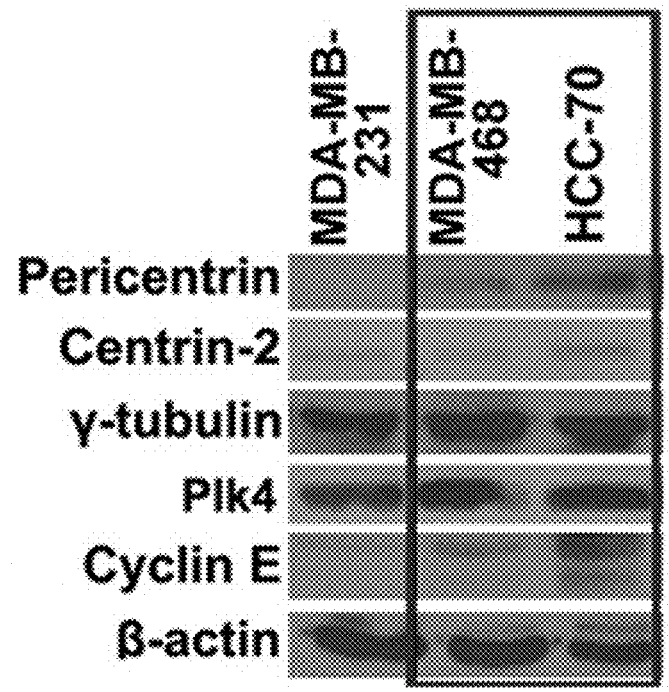

Representative immunomicrographs show that breast cancer samples from AA women show a significantly higher extent of CA than those from Caucasian women that were receptor- and grade-matched (data not shown). FIG. 5 shows that CAS was significantly higher in breast tumors derived from AA (mean=8.6) compared to those derived from receptor-matched Caucasian women (mean=6.4) (p<0.033). No differences in CAS of normal adjacent tissue from AA and Caucasian women were found. In addition, breast cancer cell lines derived from AA women (MDA-MB-468, HCC70) show elevated expression of centrosomal (pericentrin, γ-tubulin) and centrosome amplification (cyclin E) markers compared to Caucasian-derived (MDA-MB-231) lines (FIG. 6).

Figure 7:
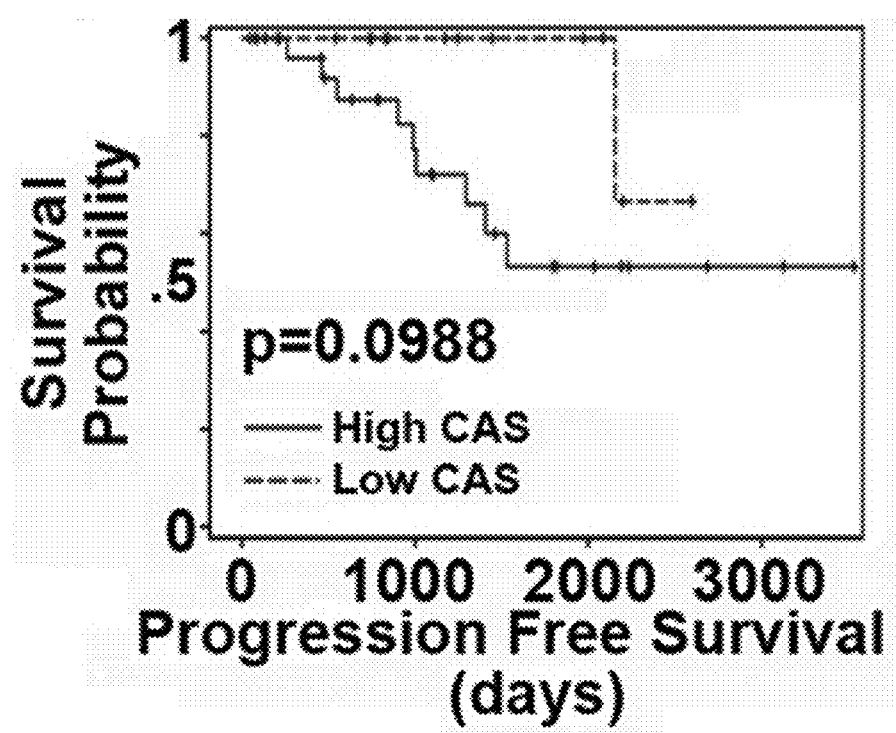

To correlate the relationship of higher centrosome aberrations (as assessed by CAS) with PFS in breast cancer patients, PFS was calculated as the number of days from diagnosis to the first local recurrence or metastasis (if one occurred), or the last follow-up if the patient did not progress. Irrespective of receptor status (n=60), patients with more centrosomal aberrations (i.e., "high CAS", above-median values) had shorter PFS (p<0.0988) than patients with lesser centrosome aberrations (i.e., "low CAS", below-median values) (FIG. 7). In this case, a majority (>85%) of the high CAS (high-risk) group was AA, while low CAS (low-risk) group was mostly Caucasian (>80%).

Example 6

Figure 8:
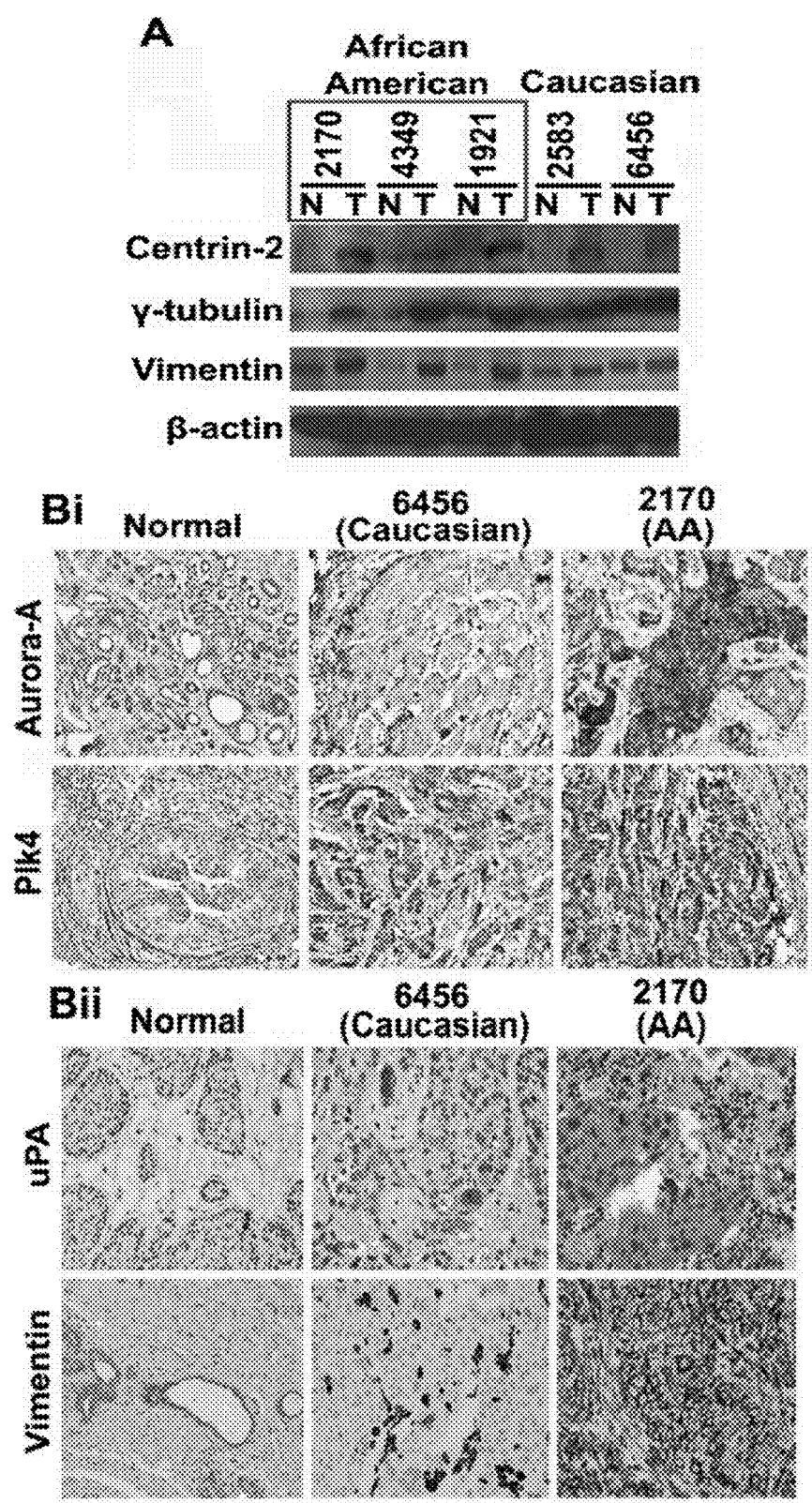
FIG. 8 illustrates that breast tumors in AA women show higher expression of centrosomal and aggressiveness markers, and proteins whose overexpression is implicated in centrosome amplification (Aurora A and Plk4), compared to Caucasian women. Panel A depicts immunoblots for 5 paired breast tumor (T) and normal adjacent (N) tissues (fresh-frozen) from grade-and receptor-matched AA and Caucasian women, showing expression levels of centrosomal and metastasis markers. Panel Bi depicts micrographs showing Aurora A and Plk4 expression in normal and cancer tissue from grade- and receptor-matched AA and Caucasian women. Panel Bii depicts micrographs showing vimentin and uPA expression in normal and cancer tissue from grade- and receptor-matched AA and Caucasian women.

Centrosome Amplification is Positively Correlated With Aggressiveness Markers Associated with Breast Cancer Metastasis Expression levels of centrosomal proteins in fresh-frozen tumor and uninvolved "normal" adjacent tissue in 10 pairs of grade- and receptor-matched samples from AA and Caucasian women were determined. Immunoblotting of cell lysates showed higher expression of two centrosomal proteins (centrin-2 and γ-tubulin) in AA than in Caucasian samples. Further, higher levels of vimentin were observed in samples that exhibited higher centrosomal protein levels (FIG. 8, panel A).

The urokinase-type plasminogen activator (uPA) along with matrix metalloproteinases (MMPs) are primarily responsible for ECM degradation in vivo and are closely linked with invasive and metastatic phenotypes in breast cancer cells. Therefore, immunohistochemical staining was employed to examine a possible correlation between centrosome amplification (Aurora A and Plk4 overexpression) and markers of breast cancer metastasis (vimentin10 and uPA overexpression) in a representative subset of two breast tumor samples. Representative micrographs show that the trends in Aurora A and Plk4 expression correlated with those of vimentin and uPA in both tumor and normal breast tissue (FIG. 8, panels Bi and Bii). Moreover, the expression levels of uPA and vimentin were significantly higher in the AA sample [2170 (T)] than in the Caucasian sample [6456 (T)] (FIG. 8, panel Bii).

Example 7

Increased CA Scores Correlate With a Lower Survival Rates in African Americans (AA) With Urothelial Carcinoma of Bladder (UCB) Compared to Grade-Matched Caucasians Urothelial carcinoma of bladder (UCB) in African-Americans (AA) presents as a more advanced disease at diagnosis and has lower, 5-year survival rate compared to Caucasians. Therefore, CA profiles of AA and Caucasians with UCB were compared by calculating their corresponding CAS scores.

Formalin-fixed, paraffin-embedded low and high-grade UCB samples AA (n=32) and Caucasian (n=22) patients were compared. Centrosomes were immunostained with anti-gamma-tubulin antibodies and DAPI nuclear stain. Confocal imaging was used to stack optical sections of tumor tissue and capture all centrosomes and nuclei within 15 regions of interest per sample. Centrosomes were categorized as (i) individually-distinguishable centrosomes (iCTRS) or (ii) large structurally aberrant megacentrosomes (mCTRs) and quantitatively analyzed for both numeral ($CAS_i$) and structural ($CAS_m$) centrosome abnormalities and the cumulative $CAS_{total}$.

The results showed that the $CAS_{total}$ was significantly higher in AA (7.2) than in grade-matched Caucasian (6.3) patients (p<0.001). Although CAS, in Caucasians was comparable to that in AA (2.4), $CAS_m$ was significantly higher in AA (5.2) as compared to Caucasians (4.1) (p<0.01) suggesting a racial disparity at the organellar level.

These findings demonstrate that AA patients had higher centrosome amplification, in particular, structural centrosomal aberrations ($CAS_m$) compared to Caucasians. Since centrosomes nucleate microtubular arrays are required for polarization and directional migration, megacentrosomes (high $CAS_m$) may confer aggressiveness and indicate the propensity of a tumor to become metastatic. Interestingly, numerical aberrations, which perhaps directly drive karyotypic heterogeneity, are maintained at significant levels in both ethnicities.

Example 8

Increased CA Scores in African-Americans (AA) With Pancreatic Adenocarcinoma Correlate With Lower Survival Rates Compared to Grade-Matched Caucasians with Pancreatic Adenocarcinoma Mortality from pancreatic cancer is higher in African-Americans (AA) compared to European Americans (EA). Although recent studies have focused on identification of gene expression signatures in whole tumors with variable metastatic potential, a disparity at the organelle-level between tumors of differing aggressiveness and metastatic potential has remained unexplored. Given the long-standing association between centrosome amplification (CA) and aggressiveness, it was hypothesized that AAs have a higher incidence and severity of CA in pancreatic adenocarcinomas as compared to EA. To test this hypothesis, Centrosome Amplification Scores (CAS) were calculated based on Formula II to quantitate the degree of CA (both numeral and structural) within tumor samples.

Tissue specimens from 39 EA and 29 AA pancreatic adenocarcinomas were immunostained for centrosomes (γ-tubulin) and nuclei (Hoechst). Immunofluorescence confocal imaging was then used to stack/take optical sections of tumor tissue and capture all centrosomes and nuclei within 10 regions of interest (ROIs) per sample. Centrosomes were categorized as (i) individually-distinguishable centrosomes (iCTRs) or (ii) as mega centrosomes (mCTRs) comprised of several tightly clustered centrosomes whose precise number could not be determined. For each ROI, the number of nuclei as well as the numbers and volumes of iCTRs and mCTRs were determined. The cumulative centrosome amplification score (CAS) was obtained for each ROI as CAS total=$CAS_i$+$CAS_m$ (CAS, for iCTRs and $CAS_m$ for mCTRs).

Based on an analysis of the resulting scores, AA tumors (n=22) were found to exhibit higher mean CAS, (16.75 vs 13.6) and $CAS_{total}$ (26.09 vs 22.48) scores than grade-matched EA (n=26) tumors, suggesting racial disparity at the organellar level (p<0.05). Further, Grade 2 tumors were found to exhibit higher mean $CAS_{total}$ scores (18.9 vs 11.1) compared to Grade 3 regardless of race (p<0.05).

These results suggest that an aggressive disease course in AA can be attributed to a higher degree and severity of CA (in particular numerical amplification) as compared to EA patients and suggest that AA patient may be more sensitive to centrosome targeting/declustering drugs. This data shows the usefulness of CAS in enabling patient stratification to channel patients into optimal treatment regimens with an overall goal of eliminating ethnic disparities in pancreatic cancer outcomes.

Example 9

HSET is Overexpressed in A Variety of Human Cancers

Figure 9:
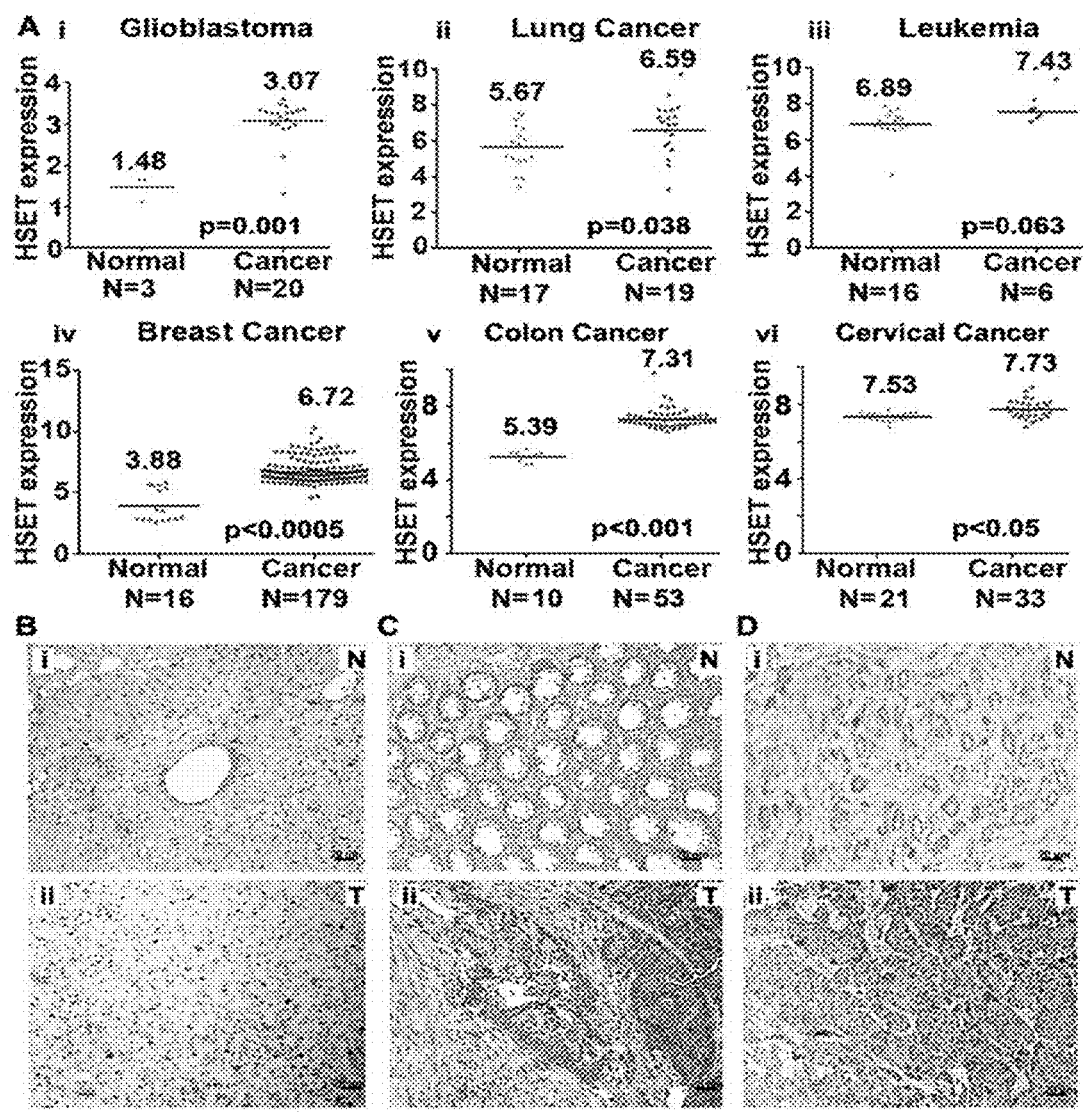
FIG. 9 shows scatter plots depicting HSET gene expression in normal versus tumor tissues in glioblastoma (Panel Ai), lung carcinoma (Panel Aii), leukemia (Panel Aiii), breast carcinoma (Panel Aiv), colon carcinoma (Panel Av) and cervical carcinoma (Panel Avi). Data were obtained from one-channel microarrays available from the GEO database. Robust multiarray normalization was performed to obtain the differences depicted in the plots. Panels B-D are immunohistographs showing HSET expression in glioblastoma tissue where a representative tumor tissue (T) (Panel Bii) is compared to normal tissue (N) (Panel Bi); in colon tumor (Panel Cii) versus adjacent normal tissue (Panel Ci); and in cervical tumor (Panel Dii) versus adjacent normal (Panel Di) tissue.

Given the crucial requirement of centrosome clustering mechanisms for the viability of cancer cells with extra centrosomes, the abundance of the clustering protein HSET in various cancers harboring extra centrosomes was investigated. Upregulating HSET expression may provide a means to permit clustering of extra centrosomes and may facilitate maintenance of low-grade aneuploidy so as to foster cell viability and allow malignant transformation and tumor evolution to proceed. An in silico gene expression analysis using publically available microarray data was employed to determine the expression level of HSET in various cancer tissue types. One-channel microarray data for glioblastoma, leukemia, lung and breast cancer patients with their normal sample pairs were collected from Gene Expression Omnibus (GEO) database. Each of these samples was then Robust Multiarray (RMA) normalized, and their logarithm to base 2-transformed HSET gene expression values were plotted to determine the difference as shown in FIG. 9, panels Ai-Avi. Differences in HSET gene expression for cancer and normal sample groups were determined using a two-tailed hypothesis test. The statistical results indicated higher HSET gene expression in glioblastoma, leukemia, lung, breast, colon and cervical tumor samples as compared to their corresponding normal tissues. The average HSET expression for glioblastoma (n=20) and colon cancer (n=53) patients was found to be ~3-fold higher than normal samples (n=3 and 10, respectively) (p<0.005), followed by breast cancer patients (n=179) with more than 5-fold higher expression in tumors than in normal samples (n=16) (p<0.001). The in silico results were consistent with observations from a previous study wherein HSET mRNA expression was significantly elevated in a broad panel of primary tumor tissue compared to corresponding normal tissue. The in silk( )data corroborates immunohistochemical analysis suggesting significantly higher HSET expression in glioblastoma, colon and cervical tumors (FIG. 9. panels Bii, Cii and Dii) as compared with their respective adjacent normal tissue samples (FIG. 9, panels Bi, Ci and Di). These data suggest HSET OE is a general feature of cancers exhibiting significant centrosome amplification.

Example 10

Characterization of Mitotic Arrest (MA) Induced by Centrosome Declustering Drugs To evaluate the impact of putative declustering drugs on cell cycle progression and hypodiploidy (<2N DNA content, which may indicate apoptotic cells), MDA-MB-231 (231), PC3, and HeLa cells were treated with different concentrations of declustering drugs, stained with propidium iodide, labeled with anti-MPM2 antibody, and then assessed by flow cytometry at multiple time points over 48 hr. The chosen cell lines displayed different levels of endogenous centrosome amplification (CA). 231 cells (mutant p53) exhibit high levels of CA (~20-45%) compared with PC3 (p53 null) and HeLa (wild-type but E6-inactivated p53), which have low basal levels of CA. Consistent with previous reports, the data showed that all drugs induced sustained MA (at least 2× mitotic cells compared with untreated control cultures) at the concentrations indicated. The duration, highest degree, and rapidity of onset of MA varied between drugs, drug concentrations, and cell lines (data not shown). In general, the maximum MA achieved was less pronounced in Nos- and PJ-treated cells. Drug-induced onset of MA was corroborated by substantial increases in cyclin B1 levels in all cell lines. For most cases, prolonged MA (~24 hr in duration) was followed by a substantial increase in the subG1 population fraction. In all cases, significant increases in cleaved caspase-3 over controls was observed, suggesting apoptosis. Instances where the subG1 fraction was elevated without cleaved caspase-3 may either represent caspase-independent cell death or the presence of hypodiploid cells whose fate is unclear. In general, no consistent associations between the extent, duration, or timing of MA within drugs or across cell lines was found.

Figure 10:
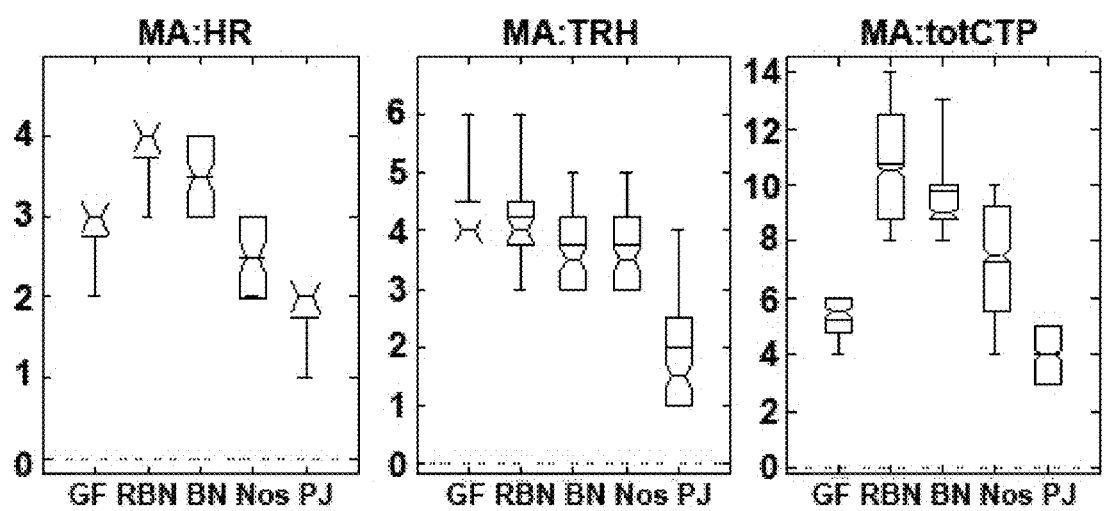
FIG. 10 depicts mitotic arrest metrics across cell lines for each declustering drug. For the box-and-whisker plots, the notch shows the median, box shows inter-quartile range, horizontal line shows mean, whiskers show min-max range. A lack of box in the plot occurs when the median is very close (or equal) to the inter-quartile range limits, in which case notch is shown with a default height and starting point of whisker line extension indicates 25% or 75% position. Because the coarse-grained data are integers and the size of the data sets are small (n<8), in some cases the median, lower or upper inter-quartile range values, or the max or min values, may coincide in some combination. This figure broadly visualizes clustering and correlation in the coarse-grained data. For instance, non-integer values have no intrinsic meaning but, for instance, a median value of 4.4 indicates a concentration of categories recorded in categories 4 or 5. Similarly, a positive R value above 0.5 suggests a possible positive correlation between the metrics versus a value near 0 or negative that would strongly suggest no correlation is likely. TRH="time reach highest" value; CTP="consecutive time points," MA_totCTP=sum (MA_SnCTP for n=2 . . . 5).

In order to discern trends in the metrics of the MA induced by declustering drugs across all cell lines, a more exhaustive evaluation of the impact of peak MA (or "highest reached," HR), onset of peak (or "time reached highest," TRH), and duration (sum or total of consecutive time points, CTP, maintaining MA) on subG1 fraction, categories were created for these metrics. Across cell lines, PJ was the fastest-acting in terms of induction of peak MA, as its mean peak onset (MA:TRH) occurred sooner (around "2", representing 12 hr) than those of the other drugs; however, the highest reached MA (MA:HR) was generally smaller than those of the other drugs (FIG. 10). For the other drugs across cell lines, the mean time to peak MA was around "4", indicating 18 hr. RBN generally induced the greatest peak MA (near "4," representing ≥30% of cells in MA) and also induced the greatest metrics for MA:totCTP (the sum of consecutive time points [CTP] with a certain level of MA, thus serving as a measure of both strength and duration of MA). BN measures of MA:HR and MA:totCTP were similar to those for RBN, although somewhat smaller (FIG. 10).

Example 11

Declustering Drugs Induce CA in Cancer Cell Lines

Figure 11:
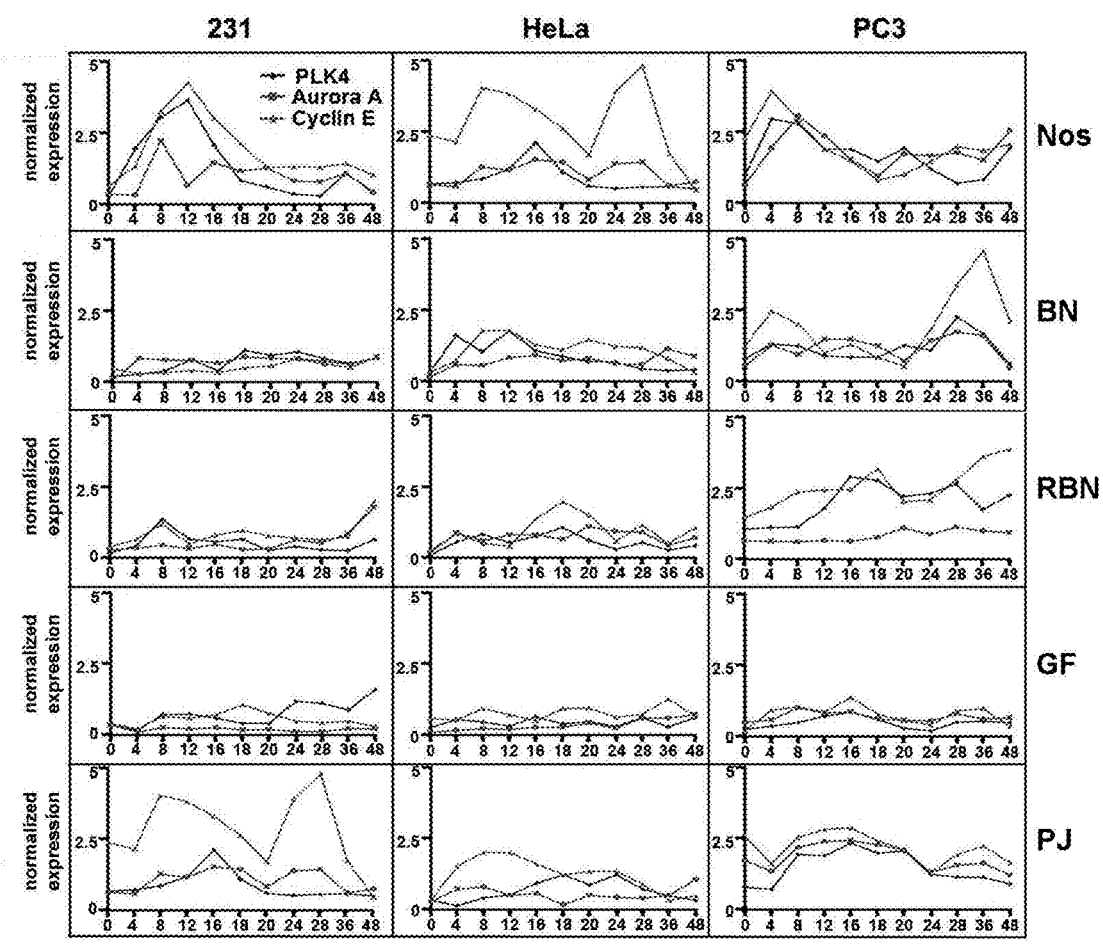
FIG. 11 shows centrosome declustering drug-induced changes in expression levels of markers of centrosome amplification. To evaluate the levels of CA markers upon treatment with declustering drugs at a concentration of 25 µM, the levels of PLK4, Cyclin E, and Aurora A were assessed by western blotting, revealing eventual increases over untreated controls across cell lines. Increases in expression levels of PLK4 and Aurora A were generally rapid, often appearing by 4 h. Levels tended to vary thereafter depending on the drug and cell line. Densitometry was performed to quantitate the changes in levels of CA markers relative to ft-actin over time, and the changes in actin-normalized expression levels over the time-course of the experiment are depicted graphically beneath each sets of blots. As the Cyclin E blots revealed two closely placed bands (49 and 43 kDa) corresponding to the two spliced forms, the Cyclin E band intensity was generated as a sum of the two band intensities.

Given that brominated noscapine (RBN) increases the expression of Plk4, a mediator of CA, other declustering drugs were investigated to determine their effect on expression of PLK4 along with two other mediators of CA, Cyclin E and Aurora A. All of the drugs studied were found to increase expression of PLK4, Cyclin E and Aurora A compared with untreated cultures (FIG. 11). Consequently, CA was assessed in cultures treated with different concentrations of declustering drugs for 6, 12, 18, or 24 h and untreated controls via microscopy. Centrosomes were identified by γ-tubulin and centrin-2 colocalization at discrete foci.

Figure 12:
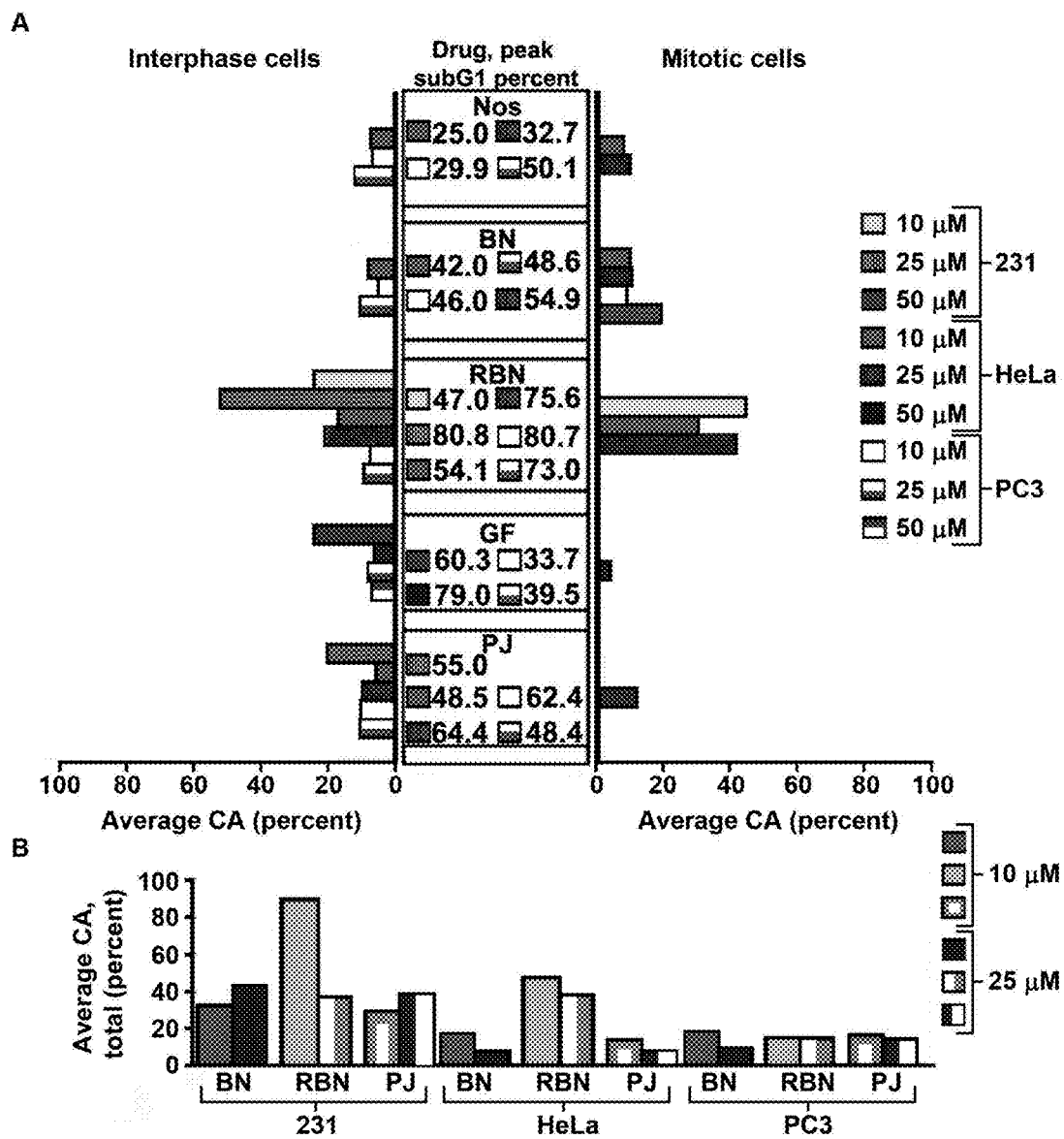
FIG. 12 shows average CA observed over 24 h and its relationship with peak subG1 for each drug treatment regimen. Panel A displays only statistically significant ($P<0.05$)

Interestingly, all drugs tested induced CA in a statistically significant manner in at least one cell type and drug concentration (10 or 25 μM for all drugs except GF, which was used at 25 and 50 μM). The average percentages of CA over 24 h and the associated fold increases over controls are shown in FIG. 12. The peak percent CA detected over 24 h is shown in FIG. 13 (only statistically significant (P<0.05) increases over control values are represented in the Figures).

When analyzing correlations between the upregulation of key molecular markers of CA and the extents of drug-induced CA, no significant correlations between the degree of CA (FIG. 12, panel A) and the expression levels of PLK4, Cyclin E and Aurora A (FIG. 11) were found. For example, even though 25 μM Nos caused a surge in the expression levels of Cyclin E and PLK4 in 231 cells (FIG. 11), it failed to induce significant CA in these cells (FIG. 12, panels A and B). Similarly, 25 μM RBN increased Cyclin E and PLK4 expression in PC3 cells but much smaller increases in the expression levels of these proteins in 231 and HeLa cells; nevertheless, RBN induced CA in all three cell lines (FIG. 12, panels A and B).

To better understand the "potency" of drug-induced CA with time, the average fold change in CA over controls over 24 h was assessed (FIG. 12, panel A), whereby the extent of CA across time points (i.e., 6, 12, 18, and 24 hr) was averaged and then divided by the extent of CA in control (i.e., 0 hr). All of the drugs at least doubled the peak extent of CA in all cell lines tested (FIG. 12, panel A), although the final extent of CA could be small or large in magnitude depending on the initial centrosomal burden as shown in FIG. 11. For instance, although 25 μM PJ treatment resulted in an almost 20-fold increase in peak CA extent in interphase HeLa cells (FIG. 12, panel A), the final extent of CA in this case was rather low at <20% (FIG. 13, panel A). On the other hand, 25 μM RBN only slightly more than doubled the peak CA extent in 231 cells (FIG. 12, panel A) although the final extent of CA was very high (around 90%, see FIG. 13, panel A). These data show that induction of CA is an activity common to all the declustering drugs studied, although the extent of the peak CA induced and its fold difference vary between drugs and cell lines (FIG. 12, panel A, FIG. 13, panel A). Analysis of the CA phenotypes induced by the various declustering drugs showed that RBN stood apart in its ability to potently upregulate centrosome number, which was especially evident in mitotic cells but also present in interphase cells. For example, in 231 cells treatment with 10 and 25 µM RBN resulted in a maximum extent of CA of 56% and 96% in mitotic cells, respectively (FIG. 12, panel A, FIG. 13, panel A), corresponding to ~2.5- and 2.0-fold increases over controls (FIG. 12, panel A). The extent of CA was less in interphase cells, with maximum values of 31% and 87% for 10 and 25 µM RBN (FIG. 13, panel A). In a similar but more pronounced fashion, 10 and 25 µM RBN also markedly upregulated centrosome numbers in mitotic HeLa cells, with 78% and 42% of cells having CA, representing approximately 40- and 20-fold increases, respectively (FIG. 12, panel A, FIG. 13, panel A). The peak extent in interphase HeLa cells was somewhat less at 30.7% and 48.1% for 10 and 25 µM RBN, respectively (FIG. 13, panel A). For Nos and BN, there was no major difference in CA levels in interphase versus mitotic cells. Since both of these drugs cause mitotic catastrophe in cancer cells, it appears that a comparable level of cell death also occurs in interphase resulting in similar levels of interphase and mitotic cells with CA. For GF and PJ, there was generally more CA in interphase than mitotic cells, which suggests selective elimination of mitotic cells with CA.

Notably, average fold-increases in CA were generally more frequent in interphase cells when compared to mitotic cells (FIG. 12, panel A). The only exception occurred with BN, which demonstrated higher average fold-increases in CA in mitotic cells (FIG. 12, panel A). It is likely that cases where average fold-increases in interphase are substantially greater than in mitosis reflect expeditious elimination of cells with amplified centrosomes via mitotic catastrophe. Similarly, regimens that resulted in a lower average-fold increase in interphase CA compared to mitotic CA may reflect precipitous death of interphase cells with CA. In sum, these data lay the foundation for studying the mechanisms by which declustering drugs induce CA and cell death by providing valuable clues about (i) potencies of CA-inducing activities of these drugs and (ii) the cell cycle phases wherein most cell death induced by these drugs may be occurring. Further, these data show that all the centrosome declustering drugs in the present study are also centrosome amplifying drugs, depending on the cell line and concentration.

As shown in Table 2, compared to HeLa and PC3 cells, 231 cells (which exhibit the greatest endogenous CA among controls, approximately 20-30% on average) were most susceptible to declustering drugs in general:

This is corroborated by the fact that 231 cells exhibited the greatest peak subG1 fraction across cell lines and drugs (25× control after treatment of 231 cells with 25 µM RBN, vs. 9× for HeLa and 8× for PC3, both treated with 10 µM RBN). Within drugs and across cell lines, BN was most effective in 231 cells, (the maximum subG1 fraction was 9.3× control, vs. 4.4× for HeLa and 9.2× for PC3, all treated with 25 µM BN), as was PJ (the maximum subG1 fraction was 10.4× control after treatment with 25 µM PJ, vs. 7.9× control in PC3 cells treated with 25 PJ and 4.8× control in HeLa cells treated with 10 µM PJ) (Table 2). GF was most effective in PC3 cells (the maximum subG1 fraction 16.3× control after treatment with 50 µM GF, vs. 6.4× for 231 cells treated with 25 µM GF and 4.3× for HeLa cells treated with 50 µM GF, although these cells do not have substantial endogenous CA (approximately 3% interphase and 4% mitotic CA on average. Altogether, it appears that certain declustering drugs (namely, RBN, BN, and PJ) may be more effective against cancer cell lines with endogenous CA, whereas the efficacy of other agents (namely, GF and Nos) may depend less on endogenous CA.

The above data indicate that RBN, BN and PJ appear to be most effective in 231 cells. To test whether higher susceptibility of 231 cells to these three drugs is related to the extent of drug-induced CA in these cell lines, the average fold-increase in CA (compared to untreated controls) induced by RBN, BN and PJ in 231 cells was evaluated and compared to the average fold-increases in CA induced by these drugs in PC3 and HeLa cells (FIG. 12, panel B). Interestingly, the average fold-increase in CA (compared to untreated controls) in 231 cells is not greater than the average fold-increase in CA induced by these 3 drugs in PC3 and HeLa (in fact, it is significantly lower in 231 compared to PC3 and HeLa) (FIG. 12, panel B). Therefore, it was concluded that the average fold-increase in CA is not responsible for the higher vulnerability of 231 cells to RBN, BN and PJ than PC3 and HeLa cells.

Upon treatment with RBN, BN, and PJ, the final total centrosomal burden (the percent of cells with CA, regardless of cell cycle stage) is much higher in 231 cells as compared to HeLa and PC3 cells (FIG. 12, panel B). This may be attributed to the fact that 231 cells start off with higher centrosome numbers than PC3 or HeLa cells. Since little is known about the biological threshold for total centrosomal load that may overcome the cell's coping mechanisms and tip the cell's fate into apoptosis, one cannot rule out the possibility that the total cellular centrosomal load (resulting from endogenous plus drug-induced CA) may be a key contributor making 231 cells more vulnerable to these drugs than PC3 and HeLa. Taken together, these observations suggest that high levels of endogenous CA in 231 cells may render them more susceptible to RBN, BN, and PJ. By

TABLE 2

Peak subG1 percents over 48 h for each cancer and non-malignant cell line by drug and concentration

| Cell Line | Concentration (µM) Drug | | | | | | | | | |
|---|---|---|---|---|---|---|---|---|---|---|
| | 10 Nos | 25 Nos | 10 BN | 25 BN | 10 RBN | 25 RBN | 25 GF | 50 GF | 10 PJ | 25 PJ |
| 231 | 26.3 | 43.9 | 32.5 | 65.2 | 47.0 | 80.8 | 62.0 | 60.0 | 37.0 | 65.0 |
| HeLa | 25.0 | 50.1 | 42.0 | 54.9 | 54.1 | 75.6 | 59.5 | 79.0 | 48.5 | 64.4 |
| PC3 | 29.9 | 32.7 | 46.0 | 42.8 | 80.7 | 73.0 | 33.7 | 39.5 | 62.4 | 48.4 |
| HDF | 14.8 | 11.2 | 16.5 | 20.4 | 35.9 | 39.9 | 32.9 | 38.3 | 13.6 | 28.2 |
| MCF10A | 4.1 | 4.2 | 3.5 | 3.0 | 36.4 | 44.0 | 22.7 | 35.1 | 6.9 | 9.1 | contrast, PC3 and HeLa cells, which lack substantial endogenous CA, are more vulnerable to treatment with GF and Nos.

Example 12

Centrosome Amplification in Non-Malignant Cell Lines

To determine whether the CA-inducing activity of declustering drugs is restricted to cancer cells, two non-malignant cell lines, mammary fibrocystic (MCF10A) cells and adult human dermal fibroblasts (HDFs) were treated with these drugs. Specifically, an analysis of the CA phenotypes produced by declustering drug treatment of MCF10A and HDFs showed that neither concentrations of Nos or BN significantly increased CA over control levels in interphase or mitotic MCF10A cells at any time point assessed over 24 h. However, both concentrations of RBN significantly increased the peak extent of CA in interphase and mitotic MCF10A cells ($p<0.001$ for all, FIG. 13, panel B, which only represents trials that resulted in statistically significant increases in peak CA over controls). 25 μM PJ also increased the peak extent of CA in interphase and mitotic cells ($p<0.001$ and $p=0.002$, respectively), while 10 μM PJ induced only a slight increase in the peak extent of CA in interphase cells (8% of cells, $p=0.029$) (FIG. 13, panel B). 25 and 50 μM GF both increased peak interphase CA (13-16%, $p<0.001$ for both) although no increase was observed in mitotic cells. Similar to MCF10As, HDFs exhibited only low levels of CA in both interphase and mitotic cells (both approximately 4%). As in MCF10As, Nos and BN did not significantly increase the extent of CA over controls at any of the concentrations or time points assessed. PJ also had no significant impact on CA in HDFs, in contrast to its effect on MFC10A cells. In comparison, 10 and 25 82 M RBN increased peak CA over controls in interphase cells ($p<0.001$ and $p=0.001$, respectively), with the lower concentration dramatically augmenting peak CA to 56% of cells versus 15% for the higher dose (FIG. 13, panel B). Only 10 but not 25 μM RBN increased the extent of CA in mitotic cells, and this upregulation was only slight (10%, $p=0.041$). 25 and 50 μM GF also increased peak CA in interphase cells only and to similar extents (14-15%, $p<0.001$ for both concentrations, FIG. 13, panel B).

Importantly, a therapeutic window exists for several of these agents at the concentrations and in the cell lines tested compared to cancer cells. Nos, BN, and PJ did not cause a significant increase in peak subG1 percent compared to controls (Table 2). RBN and GF did increase peak SubG1 in MCF10A cells compared to controls ($p<0.01$ for all). However, 10 μM RBN induced a smaller peak subG1 in MCF10A cells as compared to 231 cells ($p<0.001$), although the same was not true for PC3 and HeLa cells (Table 2). By contrast, increasing the dose of RBN to 25 which caused slightly increased toxicity to MCF10A cells, resulted in much greater increases in toxicity to 231 and PC3 cells ($p<0.001$). These data suggest that for RBN, even in in vitro cell cultures, a therapeutic window exists and can be exploited to selectively target cancer cell lines. Interestingly, previous work has demonstrated cancer selectivity of RBN in nude mice carrying human ovarian cancer xenografts. In those previous experiments, RBN inhibited tumor progression by inducing apoptosis in tumor cells, but toxicity was not detected in normal tissues. All cancer cell lines were found to be more susceptible to 25 μM GF than MCF10A cells ($p<0.001$). When the concentration was increased to 50 μM, however, MCF10A and PC3 cells were equally susceptible to the GF, although 231 and HeLa cells remained more susceptible ($p<0.001$).

In HDFs, all the drugs tested increased peak subG1 over controls in a significant fashion ($p<0.01$ for all) (Table 2). Nevertheless, for Nos and PJ, both concentrations caused more death in all cancer cell lines vs. HDFs ($p<0.001$ for all). For BN, the same was true for 231 and PC3 cells ($p<0.05$ for all) but not HeLa cells, in which there was no significant difference. For GF, both concentrations caused more death in 231 and HeLa cells ($p<0.001$ for all) but not PC3 cells, in which there was no significant difference. For RBN, both concentrations caused more death in 231 cells and 25 μM RBN caused more death in PC3 cells as compared to HDFs, ($p<0.001$ for all), but the same was not true for both concentrations in HeLa or 10 μM RBN. Thus, it appears that there may be clinically relevant therapeutic windows for these drugs depending on the type of cancer and the drug dosage.

Example 13

Cells With Amplified Centrosomes Show Higher Migration Velocity and Net Displacement Compared to Cells With Normal Centrosome Complement To evaluate if extra centrosomes are associated with cell migration, a traditional cell migration assay was performed where migration of MDA-MB 231 cells (stably transfected with GFP-tagged centriolar component, centrin) harboring 1 centrosome or >2 centrosomes was observed using time-lapse imaging (data not shown). Quantitation of merged time-lapse sequences (10 min apart, collected over 18h) showed higher average net displacement (78%), displacement rate (55%) and velocity (~2 fold enhancement) of cells with >2 centrosomes compared to cells with 1 centrosome (FIG. 14, panels A, B and C). These data strongly suggest that overabundance of centrosomes enhances migratory abilities in an aggressive breast cancer cell line.

Next, centrosome amplification was evaluated to determine the extent to which it directly and independently impacts the migration potential of a mildly aggressive cell line, ZR-75-30. ZR-75-30 cells exhibit differentiated properties such as (a) epithelial morphology resembling that of the parental tumors; (b) presence of receptors for estrogen and progesterone; and (c) growth responsiveness to estrogen and/or progesterone. In particular, it was of interest to evaluate whether generation of extra centrosomes (by genetic and pharmacological means) impacts migration and invasion kinetics by experimentally inducing centrosome amplification in these cells by aphidicolin treatment (5 μg/ml for 24 h).

Upon treatment with aphidicolin, centrosome amplification was confirmed by immunofluorescence staining for γ-tubulin (green) (data not shown) and changes in γ-tubulin and centrin levels detectable by Western blot analysis. As shown in FIG. 14, panel D, following aphidicolin treatment, a significant increase in vimentin levels was observed, along with centrosomal proteins, γ-tubulin and centrin.

To assess the migratory capacity of aphidicolin treated cells (~60% cells harboring extra centrosomes) as compared to control cells, a a classical wound healing assay was performed. Aphidicolin-treated cells were observed to fill the scratch wound in less than half the time as control cells (18 h as compared to 40 h; data not shown). Also, an increase in invasion capacity of treated cells was observed via a Boyden chamber assay, strongly suggesting that an increase in centrosome numbers can trigger an upregulation of markers of aggressiveness and enhance directional migration and invasion in breast cancer cells (data not shown).

Example 14

Declustering of Extra Centrosomes to Form Multipolar Spindles Results in Metaphase Catastrophe-Induced Cell Death To investigate a possible role for centrosome declustering drugs (such as brominated noscapines) to induce high-grade spindle multipolarity leading to cell death during mitosis, MDA-MB-231 breast cancer cells were treated with brominated noscapine. "Scattering" of amplified centrosomes in MDA-MB-231 breast cancer cells upon treatment with brominated noscapine was observed (data not shown). While control vehicle-treated cells showed pseudo-bipolar spindles due to clustering of extra centrosomes at the two poles, 18 h drug treatment at 10 µM resulted in cells with highly aberrant multipolar spindles that succumb to cell death (data not shown). Based upon this metaphasic occurrence of cell death, this caspase-mediated cellular demise reflects a "metaphase catastrophe". Near normal breast epithelial cells, MCF-10A did not exhibit any multipolarity or cell death at the same concentration. These results indicate the tremendous promise offered by this class of drugs in terms of efficacy and selectivity in inducing cell death by "ripping apart" clusters of supernumerary centrosomes.

Example 15

ZR-75-30 Breast Cancer Cells With Extra Centrosomes Display Enhanced Sensitivity to Centrosome-Disrupting Drugs Compared to Cells With a Normal Centrosomal Complement ZR-75-30 cells exhibit a relatively low degree of centrosome amplification (<10%) and a normal centrosome complement (one centrosome/interphase cell and two/mitotic cell). Accordingly, these cells can be pharmacologically manipulated with aphidicolin to generate extra centrosomes. Treatment of ZR-75-30 cells with aphidicolin for 24 h was found to cause the cells to arrest during S-phase due to decoupling of DNA replication from centrosome duplication resulting in additional rounds of centrosome overduplication leading to extra centrosomes. Following aphidicolin washout, cells were stained using anti-centrin-2 antibodies to verify extra centrosomes by immunofluorescence confocal microscopy. About ~60% ZR-75-30 cells generated extra centrosomes (6-8 per cell) and were evaluated for their sensitivity to the three drugs, griseofulvin, bromonoscapine, and PJ34, and compared with parent ZR-75-30 cells with normal centrosomes. Flow-cytometric cell cycle data showed that ZR-75-30 cells with amplified centrosomes are highly sensitive to centrosome declustering drugs and display a much higher sub-G1 population compared to parent ZR-75-30 cells (FIG. 15, panels A and B)

Example 16

High-Grade Cancers Show Robust Centrosome Amplification and Clustering in Interphase Cells Unlike Cultured Cell Lines High-grade carcinomas of the breast, prostate and colon were evaluated to determine whether mitotic and interphase centrosome clusters were present in representative tissue samples. Contrary to the notion that high-grade cancers contain relatively large proportions of mitotic cells, <2% of the cells were found to harbor mitotic spindles in the tumor samples examined (n=8 for each tissue). To assess centrosome amplification, the number of γ-tubulin dots associated with 500 nuclei in each tumor sample were counted. In most cases, centrosomes in tumor areas appeared significantly larger than centrosomes in adjacent uninvolved tissue. Exact centrosome numbers in these enlarged centrosomal clusters were difficult to determine owing to tight centrosome clustering.

Accordingly, centrosomal volumes were determined by measuring the γ-tubulin spots using the 3D volume rendering function in Zeiss imaging software (Axiovision LE). Where the volume of a centrosome was determined to be >0.76 cubic micron (maximum volume of a centrosome observed in adjacent uninvolved tissue), centrosome amplification was inferred. All tissue specimens showed centrosome amplification in 60-85% of tumor cells (FIG. 16, panel A). In order to assess centrosome clustering in interphase, centrosomes were counted and their volumes were measured from 500 interphase nuclei. Nuclei with >2 γ-tubulin spots or at least one γ-tubulin spot with increased volume at each MTOC were considered to show centrosome clustering. More than 75% of interphase cells exhibited centrosome clustering in all the cancer types examined (FIG. 16, panel B).

In contrast, 6-18% of cancer cells in culture showed mitotic spindles (data not shown), which was significantly higher than the corresponding percentage in human tumors. Moreover, only 5-20% of cells in cultured cell lines exhibited amplified centrosomes (FIG. 16, panels C and D, a lower frequency than that observed in patient tumors (FIG. 16, panel A). Multiple centrosomes in cell lines occurred as a juxtanuclear cluster in interphase cells (data not shown). Thus, while cancer cells in culture exhibit much higher levels of mitotic activity and lower levels of centrosome amplification compared with cancer cells within patients' tumors, cancer cells in culture and in tumors display the common features of centrosome clustering in interphase as well as in mitosis.

Example 17

Centrosome-Declustering Agents Disperse Interphase Clusters and Set the Stage for a Catastrophic Mitosis Given the limited mitotic populations in human cancers, centrosome declustering during mitosis alone would fail to achieve sufficient elimination of cancer cells. On the other hand, interphase declustering may not only prime the cell for catastrophic mitosis but also ensure disruption of interphase-specific cellular processes that undergird migration. To investigate how declustering agents affect centrosome clustering during interphase, three declustering drugs (RedBr-Nos, Griseofulvin and PJ-34) were tested and compared with Paclitaxel, a tubulin-polymerizing drug. Whereas RedBr-Nos, Griseofulvin and Paclitaxel are known to bind tubulin, PJ-34 is a poly-ADP-ribose polymerase inhibitor with no known tubulin-binding property. However, they share common phenotypes, such as mitotic arrest and multipolar mitoses.

N1E-115 cells were found to be more sensitive to these drugs compared with other cancer cell lines (for instance, MDA-MB-231, HeLa) with $IC_{50}$ values ranging between 0.05 µM for Paclitaxel and 25 µM for Griseofulvin (data not shown). To evaluate their effect on interphase clustering, N1E-115 cells were treated with these drugs at their respective $IC_{50}$ concentrations for 0, 3, 6 and 9 h and co-immunostained for γ-tubulin and α-tubulin to evaluate centrosomal spread and microtubule nucleation status, respectively. RedBr-Nos and Griseofulvin were found to inflict the most severe interphase declustering compared with PJ-34 and Paclitaxel.

Cell cycle phases were further evaluated via lamin A/C immunostaining to distinguish interphase declustering events from prophase centrosomal spread. To quantitate the spread of the interphase centrosomal cluster, a 3D reconstruction of z-stack images of 25 randomly-selected interphase cells from the 6-h treatment group of each drug were generated. By defining an ROI (region of interest) around the interphase centrosomal cluster, the volume of the cluster spread was calculated using Volocity software. Likewise, defining an ROI using the cell periphery provided the cell volume. FIG. 17 shows an interphase declustering index (DI) for each drug as the ratio of the average volume of clusters to the average volume of the corresponding cell. Quantitative evaluation of DI revealed RedBr-Nos as the strongest declustering agent (DI=0.36), followed by Griseofulvin (DI=0.28) and PJ-34 (0.14). Paclitaxel showed the least declustering effect with a DI of 0.08 as compared with 0.02 in control cells. Dispersal of the interphase centrosome cluster was found to precipitate multipolar mitoses in the treated cells (data not shown). Again, the proportion of multipolar cells was higher in RedBr-Nos- and Griseofulvin-treated cells as compared with cells treated with PJ-34 and Paclitaxel, which mirrored the trend in interphase declustering. These observations suggest that interphase declustering of centrosomes compels cells into catastrophic multipolar mitoses.

Example 18

Centrosome Declustering in Interphase Disrupts Golgi Coalescence and Inhibits Migration The Golgi, which is primarily responsible for posttranslational modification and protein sorting, also functions as a microtubule-organizing center (MTOC). It has been hypothesized that supernumerary centrosomes may better organize the Golgi to enhance directional cell migration. To investigate what happens to the Golgi upon declustering drug-induced dispersal of the interphase centrosomal cluster, drug-treated N1E-115 cells were co-immunostained with GM130 (a cis-Golgi matrix protein crucial for maintaining its structure) and γ-tubulin. Following treatment with RedBr-Nos, Griseofulvin, PJ-34 and Paclitaxel, the interphase Golgi complex fragmented, and the distribution of Golgi fragments closely mimicked scattering of the centrosomal cluster, with the most robust effect seen with RedBr-Nos and Griseofulvin (data not shown).

It has been suggested that Golgi-derived microtubules are not sufficient to preserve cell polarization; instead, they need to act in concert with the centrosome to establish and maintain cell polarization. In cancer cells harboring a supercentrosomal cluster, it is predicted that disrupting the cytoskeletal and organellar framework organized by a strongly polarizing supercentrosomal cluster will present a setback to the mechanical thrust that such a cluster can empower a migrating cell to produce impaired directional migration. As a surrogate for the polarization underlying such a directional migration, the process of neuritogenesis was further examined.

Neuritogenesis is a process in nerve cells involving the extension of polarized, elongated neurites. N1E-115 cells usually extend only one major neurite per cell, which can vary in length from 5 to 500 µm. The growth cones of the neurites serve as primary focal points of motility. The effect of declustering agents on cell motility was evaluated by assessing the length and frequency of neurites formed in a serum-free medium on a laminin-coated surface. Neurite growth under these conditions is linear for up to 24 h, reaching a maximum around 36-48 h after plating. Phase-contrast imaging showed the presence of several elongated (10-200 µm long) neurites upon 48 h of serum starvation (FIG. 18, panel A). Upon treatment with RedBr-Nos and Griseofulvin, 70-80% inhibition of neurite extension was observed, whereas moderate inhibition neurite extension was observed following treatment with PJ-34 and Paclitaxel (FIG. 18, panel B). Confocal imaging confirmed that inhibition of neurite formation was accompanied by dispersal of the interphase centrosome cluster, which is normally situated near the base of the tubulin-rich neurite shaft (data not shown).

In order to establish whether Golgi-dependent vesicular trafficking lies downstream of interphase centrosome clustering during cell polarization and neuritogenesis in N1E-115 cells, the effect of centrosome-declustering-independent Golgi scattering on neuritogenesis was evaluated. This was accomplished using CLASP1 siRNA to disrupt the Golgi-nucleated microtubules so as to disarray the directionality of post-Golgi vesicular trafficking, while leaving the centrosome cluster intact, and then evaluating whether these cells can generate neurites. In this case, ~50% Golgi scattering was observed following CLASP1 knockdown (FIG. 18, panel C). Cells with CLASP1 siRNA were found to form significantly fewer neurites compared with control cells (data not shown). This observation suggests that (i) disruption of Golgi network impedes Golgi polarization-dependent neuritogenesis, and (ii) Golgi complex integrity and polarized post-Golgi trafficking lie downstream of interphase centrosome clustering.

The spatio-temporal arrangement of Golgi apparatus serves as a geometrical regulator of cell migration as well as neurite extension. Thus, it was of interest to determine whether Golgi disruption following CLASP1 knockdown affects cell shape and cell adhesion, the modulation of which is crucial for cell migration as a precursory step for neurite extension in N1E-115 cells. A significant shift in the morphology of cells from majorly mesenchymal-like cell shape in cells transfected with control vector to largely amoeboid-like and more 'rounded' cell shape in CLASP1 knockdown cells was observed (data not shown). This shift in cell morphology indicates changes in cell-substrate adhesion properties as a result of Golgi dispersal, which was confirmed by a reduction in vinculin localization at distinct adhesion focal points in CLASP1 siRNA cells (data not shown).

Vinculin stabilizes cell-substrate contacts in neuronal cells undergoing neuritogenesis, while activation by actin-binding proteins mobilizes vinculin to focal adhesions. To determine the localization of vinculin in the neurite extensions and the effect of declustering agents on its localization, N1E-115 cells were immunostained cells for vinculin and stained F-actin using rhodamine-phalloidin. Cells in serum-supplemented medium showed vinculin localization at focal adhesions with very little internalized vinculin; following serum starvation for 48 h, most of the vinculin was localized to the neurite growth cones (data not shown). However, upon treatment of serum-starved (SS) cells with RedBr-Nos and Griseofulvin, complete internalization of vinculin and complete loss of focal adhesion points was observed. The observed effect was less severe with PJ-34 and Paclitaxel (data not shown). Centrosome-declustering drugs thus impair cell polarization and neurite formation and the localization of vinculin, a key player in the establishment of cell-substrate contacts.

Declustering agents were comparatively less affective in disrupting neuritogenesis of mouse neuroblastoma cells, Neuro-2a (harboring much lesser degree of centrosome amplification) (data not shown). This is consistent with the notion that the dispersion of centrosomal clusters in interphase is directly responsible for anti-migratory effects of these drugs and are not merely side effects of the drugs. Together, these observations underscore the immense clinical potential of centrosome declustering as a selective therapy for cancer cells harboring excess centrosomes, without affecting cells with normal centrosome content.

Example 19

Inhibition of Migration Results in Interphase Cell Death or Pushes Cells Into Catastrophic Mitosis Several studies suggest an intrinsic, inverse relationship between cell migration and cell proliferation. This concept that cells exist in mutually exclusive cellular states that either permit motility or mitotic activity is evidenced by numerous in vitro and in vivo studies and is referred to as "Go-or-Grow". Accordingly, the effects of declustering drug treatment of SS N1E-115 cells on migration inhibition via proliferation (indicated by Ki67 nuclear immunostaining) or induction of apoptosis (indicated by cleaved caspase-3 immunostaining) were examined.

Upon treatment with the three declustering drugs, RedBr-Nos, Griseofulvin and PJ-34, a high proportion of Ki67-positive cells was found (FIG. 19). In contrast, negligible numbers of Ki67-positive SS N1E-115 cells were found, which should predominantly be in the G0 phase of the cell cycle (data not shown). These data suggest that declustering drugs cause more cells to enter the cell cycle under the conditions of serum starvation.

To see whether apoptosis is induced by interphase declustering and whether any induced cell death depends on the cells' passage through mitosis, cleaved caspase-3 staining in N1E-115 cells was examined upon treatment with the three drugs for 9 h (a time point at which the vast majority of cells were in interphase; data not shown). This analysis revealed a higher proportion of caspase-3 positive interphase cells in the drug-treated cultures compared with untreated controls, indicating significant induction of cell death during interphase (data not shown). Interphase-specific cell death was confirmed with a cell-clock assay (data not shown). These observations suggest that disrupting the supercentrosomal cluster during interphase in N1E-115 cells (a) induces interphase catastrophe, and (b) pushes cells into a proliferative mode leading to a catastrophic mitosis. These data show that centrosome-declustering drugs launch a two-pronged attack on supercentrosomal cells.

Determining Cancer Risk of Atypical Hyperplasia

More than 1 million of the breast biopsies that are performed annually in the United States are found to be benign. On the basis of the histologic findings, it is possible to stratify women with benign biopsy findings into groups with significantly different risks of later breast cancer. Atypical hyperplasia is a high-risk benign lesion that is found in approximately 10% of biopsies with benign findings. There are two types of atypical hyperplasia, as classified on the basis of microscopic appearance: Atypical ductal hyperplasia and atypical lobular hyperplasia; these occur with equal frequency and confer similar risks of later breast cancer. Atypical ductal hyperplasia is characterized by filling and distention of the involved ducts by monotonous epithelial cells forming architecturally complex patterns, including cribriform-like secondary lumens or micropapillary formations. In atypical lobular hyperplasia, the acini of a lobular unit are expanded and filled with small, monotonous, round or polygonal cells with a lack of cohesion and a loss of acinar lumens.

Atypical hyperplasia is a well-established risk factor for subsequent breast cancer. Multiple studies corroborate an approximately four-fold increased risk of breast cancer in women undergoing surgical biopsy with a finding of atypia. Despite good concordance on the estimated relative risk (RR) with atypia, estimates of absolute risk with long-term follow-up are not well established. Reliable breast cancer risk estimates for women with atypia are crucial for risk-benefit analysis and decision making regarding risk-reduction strategies. Having reliable breast cancer risk estimates for women with atypical hyperplasia is imperative in order to tailor their care appropriately.

In some embodiments, CAS scores are generated from biopsy samples of breast atypical hyperplastic lesions for determination of risk of breast cancer associated with these lesions.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A method of determining the risk profile of a neoplastic tissue in a patient, the method comprising:
   (a) processing a sample of tumor tissue or cancer cells from the patient in a form suitable for visualization and demarcation of cell nuclei, individually distinguishable centrosomes (iCTRs) and megacentrosomes (mCTRs) in a region of interest (ROI) defined by a plurality of cell nuclei;
   (b) labeling cell nuclei, iCTRs and mCTRs by fluorescence staining and/or immunohistochemical staining;
   (c) imaging the iCTRs and/or mCTRs three dimensionally and determining the numbers of iCTRs and/or mCTRs, and the number of cell nuclei in the ROI;
   (d) determining the volume of each iCTR and/or mCTR in the ROI; and
   (e) calculating one or more centrosome amplification scores (CASs) values for the sample based on steps (c) and (d),
   wherein the one or more CASs indicate the severity of centrosome amplification, the frequency of centrosome amplification, or both, and wherein the one or more scores provide a measure of a level of risk and/or a prognosis associated with the neoplastic tissue.

2. The method of claim 1, wherein the sample in step (a) is fresh-frozen in an optimal cutting temperature (OCT) compound.

3. The method of claim 1, wherein the ROI comprises a whole slide of fixed cells.

4. The method of claim 1, wherein the iCTRs and mCTRs are labeled by immunofluorescence staining and three dimensional (3D) imaging of the iCTRs and mCTRS in the centrosomes is carried out by confocal imaging of immunofluorescently stained centrosomes.

5. The method of claim 1, wherein the iCTRs and mCTRs are labeled by immunohistochemical staining and 3D imaging of the iCTRs and mCTRS is carried out using a bright field imaging system with optical section followed by image deconvulation to enable software-assisted 3D volume rendering.

6. The method of claim 1, wherein step (c) further comprises the substep of determining a number of iCTRs per cell nucleus among cell nuclei associated with more than two centrosomes and determining a percentage of cell nuclei associated with more than two centrosomes among all demarcated nuclei in the ROI.

7. The method of claim 1, wherein step (d) comprises the substep of determining a volume deviation of mCTRs among cell nuclei associated with mCTRs and a percentage of cell nuclei associated with mCTRs among all demarcated nuclei in the ROI.

8. The method of claim 1, wherein the neoplastic tissue is cancer tissue.

9. The method of claim 8, wherein the cancer tissue is breast cancer tissue.

10. The method of claim 8, wherein the cancer tissue is bladder cancer tissue.

11. The method of claim 8, wherein the cancer tissue is pancreatic cancer tissue.

12. The method of claim 8, wherein the cancer tissue is prostate cancer tissue.

13. The method of claim 1, wherein the cell nuclei are labeled with DAPI and the centrosomes are labeled with an antibody to a component of pericentriolar matrix.

14. The method of claim 1, wherein the steps (b)-(d) are performed with the aid of software selected from the group consisting of:
software adapted to support the entry of data, including numbers of iCTRs and mCTRs associated with each cell nucleus in an ROI;
software adapted to generate three dimensional image data sufficient for volume rendering of iCTRs and mCTRs in the ROI;
software adapted to determine the volume of each iCTR and mCTR in the ROI;
software adapted to calculate one of more centrosome amplification scores (CASs) based on the number of iCTRs associated with each cell nucleus, number and percentage of cell nuclei associated with iCTRs, number and percentage of cell nuclei associated with mCTRs, number of mCTRs associated with each cell nucleus and the volume of each iCTR and mCTR;
software adapted to determine numbers of iCTRs and mCTRs per nucleus in the ROI;
software adapted to determine a number of iCTRs per cell nucleus among cell nuclei associated with more than two centrosomes and to determine a percentage of cell nuclei associated with more than two centrosomes among all demarcated nuclei in the ROI;
software adapted to determine a volume deviation of mCTRs among cell nuclei associated with mCTRs and to determine a percentage of cell nuclei associated with mCTRs among all demarcated nuclei in the ROI; and/or
software adapted to compare one of more centrosome amplification scores (CASs) to corresponding reference CASs or CAS ranges and providing an estimated risk or prognosis of the cancer.

15. The method of claim 1, further comprising:
administering to a patient, who is determined to have a high risk or poor prognosis based on the one or more scores determined in step (d), an effective amount of a centrosome declustering agent or a microtubule targeting drug.

16. The method of claim 1, wherein the one or more CASs for the sample comprise a CAS for iCTRs ($CAS_i$), a CAS for mCTRs ($CAS_m$), and a total CAS ($CAS_{total}$), wherein $$CAS_{total} = CAS_i + CAS_m.$$

17. The method of claim 16, further comprising:
comparing the one or more CASs of the sample to corresponding reference CASs or CAS ranges to determine a risk level or prognosis of the cancer.

18. A method for determining chromosomal instability in a subject, comprising
(a) processing a sample of tumor tissue or cancer cells from the subject in a form suitable for visualization and demarcation of cell nuclei, individually distinguishable centrosomes (iCTRs) and megacentrosomes (mCTRs) in a region of interest (ROI) defined by a plurality of cell nuclei;
(b) labeling cell nuclei, iCTRs and mCTRs by fluorescence staining and/or immunohistochemical staining;
(c) imaging the iCTRs and/or mCTRs three dimensionally and determining the numbers of iCTRs and/or mCTRs, and the number of cell nuclei in the ROI;
(d) determining the volume of each iCTR and/or mCTR in the ROI; and
(e) calculating one or more centrosome amplification scores (CASs) values for the sample based on steps (c) and (d),
wherein the one or more CASs indicate the severity of chromosomal instability.

* * * * *